(12) United States Patent
Apostolou et al.

(10) Patent No.: US 9,023,997 B2
(45) Date of Patent: May 5, 2015

(54) ANTI-ILT5 ANTIBODIES AND ILT5-BINDING ANTIBODY FRAGMENTS

(75) Inventors: Irina Apostolou, Roslindale, MA (US); Paul Ponath, San Francisco, CA (US); Joe Ponte, Weymouth, MA (US); Michael Rosenzweig, Boston, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 335 days.

(21) Appl. No.: 13/574,307

(22) PCT Filed: Jan. 20, 2011

(86) PCT No.: PCT/US2011/021939
§ 371 (c)(1),
(2), (4) Date: Oct. 9, 2012

(87) PCT Pub. No.: WO2011/091177
PCT Pub. Date: Jul. 28, 2011

(65) Prior Publication Data
US 2013/0030156 A1    Jan. 31, 2013

Related U.S. Application Data

(60) Provisional application No. 61/296,791, filed on Jan. 20, 2010.

(51) Int. Cl.
*C07K 16/00* (2006.01)
*C12P 21/08* (2006.01)
*C07K 16/28* (2006.01)
*C07K 1/00* (2006.01)
*A61K 39/00* (2006.01)

(52) U.S. Cl.
CPC ....... *C07K 16/2803* (2013.01); *A61K 2039/505* (2013.01); *A61K 2039/55516* (2013.01); *C07K 2317/74* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 2002/0012909 A1 | 1/2002 | Plaksin | |
| 2007/0037217 A1 | 2/2007 | Luo et al. | |
| 2008/0286269 A1 | 11/2008 | Violette et al. | |
| 2009/0098109 A1 | 4/2009 | Shatz et al. | |
| 2009/0136516 A1 | 5/2009 | Tedder et al. | |
| 2009/0175860 A1 | 7/2009 | Stover et al. | |
| 2009/0215165 A1 | 8/2009 | Rance et al. | |
| 2010/0285037 A1 | 11/2010 | Abo et al. | |
| 2011/0217305 A1* | 9/2011 | Pedersen et al. | 424/138.1 |
| 2011/0243963 A1 | 10/2011 | Abo et al. | |

FOREIGN PATENT DOCUMENTS

| WO | WO2009051974 A1 | 4/2009 |
|---|---|---|
| WO | WO2009064944 A3 | 1/2010 |

OTHER PUBLICATIONS

Rudikoff et al. PNAS 1982 vol. 79 p. 1979-1983.*
William E. Paul. Fundamental Immunology, 3rd ed. 1993, p. 242.*
Portolano et al., Journal of Immunology, 1993 150:880-887.*
Casset et al. (BBRC(2003) 307, 198-205.*
Janeway et al., Immunology Third Edition, Garland Publishing Inc. 1997, Chapter 3, Structure of the Antibody Molecule and Immunoglobulin Genes, pp. 3:1-3:11.*
Pfisterhammer et al. Allogeneic disparities in immunoglobulin-like transcript 5 induce potent 1,3-10,21,23-26 antibody responses in hematopoietic stem cell transplant recipients. Blood Sep. 10, 2009, 114( 11 ):2323-2332.

* cited by examiner

*Primary Examiner* — Chun Dahle
(74) *Attorney, Agent, or Firm* — Gloria Fuentes; Immac Thampoe

(57) ABSTRACT

Disclosed herein are antibodies and ILT5-binding fragments thereof that specifically bind to ILT5, e.g., human ILT5 (hILT5), and pharmaceutical compositions comprising such ILT5-binding antibodies and ILT5-binding fragments thereof.

22 Claims, 14 Drawing Sheets

SEQUENCE LISTING

<160> NUMBER OF SEQ ID NOS: 32

<210> SEQ ID NO 1
<211> LENGTH: 107
<212> TYPE: PRT
<213> ORGANISM: Mus musculus

<400> SEQUENCE: 1

Asp Ile Gln Met Thr Gln Ser Pro Ala Ser Leu Ser Val Ser Val Gly
 1               5                  10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Val Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Phe Ser Leu Lys Ile Asn Ser Leu Gln Ser
65                  70                  75                  80

Glu Asp Phe Gly Asn Tyr Phe Cys Gln His Phe Trp Arg Ile Pro Trp
                85                  90                  95

Thr Phe Gly Gly Gly Thr Lys Leu Glu Ile Lys
            100                 105

<210> SEQ ID NO 2
<211> LENGTH: 124
<212> TYPE: PRT
<213> ORGANISM: Mus musculus

<400> SEQUENCE: 2

Asp Val Gln Leu Gln Glu Ser Gly Pro Gly Leu Val Lys Pro Ser Gln
 1               5                  10                  15

Ser Leu Phe Leu Thr Cys Ser Val Thr Gly Tyr Ser Ile Ser Ser Ser
            20                  25                  30

Tyr Tyr Trp Asn Trp Ile Arg Gln Phe Pro Gly Asn Lys Leu Glu Trp
        35                  40                  45

Met Gly Tyr Ile Ser Phe Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Glu Lys Glu Asn Tyr Tyr Gly Ser Ser Phe Tyr Tyr Phe Asp
            100                 105                 110

Tyr Trp Gly Leu Gly Thr Ser Leu Thr Val Ser Ser
        115                 120

<210> SEQ ID NO 3
<211> LENGTH: 124
<212> TYPE: PRT
<213> ORGANISM: Mus musculus

<400> SEQUENCE: 3

Glu Val Gln Leu Gln Glu Ser Gly Pro Gly Leu Val Lys Pro Ser Gln
 1               5                  10                  15

Ser Leu Phe Leu Thr Cys Ser Val Thr Gly Tyr Ser Ile Ser Ser Ser
            20                  25                  30

Tyr Tyr Trp Asn Trp Ile Arg Gln Phe Pro Gly Asn Lys Leu Glu Trp
        35                  40                  45

```
Met Gly Tyr Ile Ser Phe Asp Gly Ser Asn Asn Tyr Asn Pro Ser Leu
        50                  55                  60

Lys Asn Arg Ile Ser Ile Thr Arg Asp Thr Ser Lys Asn Gln Phe Phe
 65                  70                  75                  80

Leu Lys Leu Asn Ser Val Thr Thr Glu Asp Thr Ala Thr Tyr Tyr Cys
                85                  90                  95

Ala Arg Glu Lys Glu Asn Tyr Tyr Gly Ser Ser Phe Tyr Tyr Phe Asp
            100                 105                 110

Tyr Trp Gly Leu Gly Thr Ser Leu Thr Val Ser Ser
            115                 120
```

<210> SEQ ID NO 4
<211> LENGTH: 6
<212> TYPE: PRT
<213> ORGANISM: Mus musculus

<400> SEQUENCE: 4

```
Ser Ser Tyr Tyr Trp Asn
 1               5
```

<210> SEQ ID NO 5
<211> LENGTH: 16
<212> TYPE: PRT
<213> ORGANISM: Mus musculus

<400> SEQUENCE: 5

```
Tyr Ile Ser Phe Asp Gly Ser Asn Asn Tyr Asn Pro Ser Leu Lys Asn
 1               5                  10                  15
```

<210> SEQ ID NO 6
<211> LENGTH: 15
<212> TYPE: PRT
<213> ORGANISM: Mus musculus

<400> SEQUENCE: 6

```
Glu Lys Glu Asn Tyr Tyr Gly Ser Ser Phe Tyr Tyr Phe Asp Tyr
 1               5                  10                  15
```

<210> SEQ ID NO 7
<211> LENGTH: 11
<212> TYPE: PRT
<213> ORGANISM: Mus musculus

<400> SEQUENCE: 7

```
Arg Ala Ser Glu Asn Ile Tyr Ser Asn Leu Ala
 1               5                  10
```

<210> SEQ ID NO 8
<211> LENGTH: 7
<212> TYPE: PRT
<213> ORGANISM: Mus musculus

<400> SEQUENCE: 8

```
Ala Ala Thr Asn Leu Ala Asp
 1               5
```

<210> SEQ ID NO 9
<211> LENGTH: 9
<212> TYPE: PRT
<213> ORGANISM: Mus musculus

<400> SEQUENCE: 9

```
Gln His Phe Trp Arg Ile Pro Trp Thr
  1               5
```

```
<210> SEQ ID NO 10
<211> LENGTH: 124
<212> TYPE: PRT
<213> ORGANISM: Homo sapiens

<400> SEQUENCE: 10
```

```
Gln Val Gln Leu Gln Glu Ser Gly Pro Gly Leu Val Lys Pro Pro Gly
  1               5                  10                  15

Thr Leu Ser Leu Thr Cys Ala Val Ser Gly Gly Ser Ile Ser Ser Ser
             20                  25                  30

Tyr Tyr Trp Asn Trp Val Arg Gln Pro Pro Gly Lys Gly Leu Glu Trp
         35                  40                  45

Ile Gly Tyr Ile Ser Phe Asp Gly Ser Asn Asn Tyr Asn Pro Ser Leu
     50                  55                  60

Lys Asn Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Cys Cys
                 85                  90                  95

Ala Arg Glu Lys Glu Asn Tyr Tyr Gly Ser Ser Phe Tyr Tyr Phe Asp
                100                 105                 110

Tyr Trp Gly Gln Gly Thr Leu Val Thr Val Ser Ser
            115                 120
```

```
<210> SEQ ID NO 11
<211> LENGTH: 124
<212> TYPE: PRT
<213> ORGANISM: Homo sapiens

<400> SEQUENCE: 11
```

```
Gln Val Gln Leu Gln Glu Ser Gly Pro Gly Leu Val Lys Pro Ser Gly
  1               5                  10                  15

Thr Leu Ser Leu Thr Cys Ala Val Ser Gly Gly Ser Ile Ser Ser Ser
             20                  25                  30

Tyr Tyr Trp Asn Trp Val Arg Gln Pro Pro Gly Lys Gly Leu Glu Trp
         35                  40                  45

Ile Gly Tyr Ile Ser Phe Asp Gly Ser Asn Asn Tyr Asn Pro Ser Leu
     50                  55                  60

Lys Asn Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Cys Cys
                 85                  90                  95

Ala Arg Glu Lys Glu Asn Tyr Tyr Gly Ser Ser Phe Tyr Tyr Phe Asp
                100                 105                 110

Tyr Trp Gly Gln Gly Thr Leu Val Thr Val Ser Ser
            115                 120
```

```
<210> SEQ ID NO 12
<211> LENGTH: 124
<212> TYPE: PRT
<213> ORGANISM: Homo sapiens

<400> SEQUENCE: 12
```

```
Gln Val Gln Leu Gln Glu Ser Gly Pro Gly Leu Val Lys Pro Pro Gly
  1               5                  10                  15

Thr Leu Ser Leu Thr Cys Ala Val Ser Gly Gly Ser Ile Ser Ser Ser
```

```
            20                  25                  30
Tyr Tyr Trp Asn Trp Val Arg Gln Pro Pro Gly Lys Gly Leu Glu Trp
        35                  40                  45

Ile Gly Tyr Ile Ser Phe Asp Gly Ser Asn Asn Tyr Asn Pro Ser Leu
    50                  55                  60

Lys Asn Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Lys Glu Asn Tyr Tyr Gly Ser Ser Phe Tyr Tyr Phe Asp
            100                 105                 110

Tyr Trp Gly Gln Gly Thr Leu Val Thr Val Ser Ser
            115                 120

<210> SEQ ID NO 13
<211> LENGTH: 124
<212> TYPE: PRT
<213> ORGANISM: Homo sapiens

<400> SEQUENCE: 13

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Ser
            20                  25                  30

Tyr Tyr Trp Asn Trp Ile Arg Gln Pro Pro Gly Lys Gly Leu Glu Trp
        35                  40                  45

Ile Gly Tyr Ile Ser Phe Asp Gly Ser Asn Asn Tyr Asn Pro Ser Leu
    50                  55                  60

Lys Asn Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Glu Lys Glu Asn Tyr Tyr Gly Ser Ser Phe Tyr Tyr Phe Asp
            100                 105                 110

Tyr Trp Gly Gln Gly Thr Leu Val Thr Val Ser Ser
            115                 120

<210> SEQ ID NO 14
<211> LENGTH: 124
<212> TYPE: PRT
<213> ORGANISM: Homo sapiens

<400> SEQUENCE: 14

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Tyr Tyr Trp Asn Trp Ile Arg Gln Pro Pro Gly Lys Gly Leu Glu Trp
        35                  40                  45

Ile Gly Tyr Ile Ser Phe Asp Gly Ser Asn Asn Tyr Asn Pro Ser Leu
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Lys Glu Asn Tyr Tyr Gly Ser Ser Phe Tyr Tyr Phe Asp
```

```
                  100                 105                 110
Tyr Trp Gly Gln Gly Thr Leu Val Thr Val Ser Ser
        115                 120

<210> SEQ ID NO 15
<211> LENGTH: 124
<212> TYPE: PRT
<213> ORGANISM: Homo sapiens

<400> SEQUENCE: 15

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Ser
            20                  25                  30

Tyr Tyr Trp Asn Trp Ile Arg Gln Pro Pro Gly Lys Gly Leu Glu Trp
            35                  40                  45

Ile Gly Tyr Ile Ser Phe Asp Gly Ser Asn Asn Tyr Asn Pro Ser Leu
        50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Lys Glu Asn Tyr Tyr Gly Ser Ser Phe Tyr Tyr Phe Asp
            100                 105                 110

Tyr Trp Gly Gln Gly Thr Leu Val Thr Val Ser Ser
        115                 120

<210> SEQ ID NO 16
<211> LENGTH: 124
<212> TYPE: PRT
<213> ORGANISM: Homo sapiens

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Ser
            20                  25                  30

Tyr Tyr Trp Asn Trp Ile Arg Gln Pro Pro Gly Lys Gly Leu Glu Trp
            35                  40                  45

Ile Gly Tyr Ile Ser Phe Asp Gly Ser Asn Asn Tyr Asn Pro Ser Leu
        50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Lys Glu Asn Tyr Tyr Gly Ser Ser Phe Tyr Tyr Phe Asp
            100                 105                 110

Tyr Trp Gly Gln Gly Thr Leu Val Thr Val Ser Ser
        115                 120

<210> SEQ ID NO 17
<211> LENGTH: 124
<212> TYPE: PRT
<213> ORGANISM: Homo sapiens

<400> SEQUENCE: 17

Gln Val Gln Leu Gln Glu Ser Gly Pro Gly Leu Val Lys Pro Ser Glu
1               5                   10                  15
```

```
Thr Leu Ser Leu Thr Cys Ala Val Ser Gly Tyr Ser Ile Ser Ser
            20                  25                  30

Tyr Tyr Trp Asn Trp Ile Arg Gln Pro Pro Gly Lys Gly Leu Glu Trp
            35                  40                  45

Ile Gly Tyr Ile Ser Phe Asp Gly Ser Asn Asn Tyr Asn Pro Ser Leu
        50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Lys Glu Asn Tyr Tyr Gly Ser Ser Phe Tyr Tyr Phe Asp
            100                 105                 110

Tyr Trp Gly Gln Gly Thr Leu Val Thr Val Ser Ser
        115                 120
```

<210> SEQ ID NO 18
<211> LENGTH: 112
<212> TYPE: PRT
<213> ORGANISM: Homo sapiens

<400> SEQUENCE: 18

```
Ala Ile Arg Met Thr Gln Ser Pro Ser Ser Phe Ser Ala Ser Thr Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Phe Ala Thr Tyr Tyr Cys Gln His Phe
                85                  90                  95

Trp Arg Ile Pro Trp Thr Phe Gly Gln Gly Thr Lys Val Glu Ile Lys
            100                 105                 110
```

<210> SEQ ID NO 19
<211> LENGTH: 107
<212> TYPE: PRT
<213> ORGANISM: Homo sapiens

<400> SEQUENCE: 19

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln His Phe Trp Arg Ile Pro Trp
                85                  90                  95

Thr Phe Gly Gln Gly Thr Lys Val Glu Ile Lys
            100                 105
```

<210> SEQ ID NO 20
<211> LENGTH: 107
<212> TYPE: PRT
<213> ORGANISM: Homo sapiens

<400> SEQUENCE: 20

```
Asp Ile Gln Met Thr Gln Ser Pro Ser Ser Val Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Arg Ile Pro Trp
                85                  90                  95

Thr Phe Gly Gln Gly Thr Lys Val Glu Ile Lys
            100                 105
```

<210> SEQ ID NO 21
<211> LENGTH: 107
<212> TYPE: PRT
<213> ORGANISM: Homo sapiens

<400> SEQUENCE: 21

```
Asp Ile Gln Met Thr Gln Ser Pro Ser Ser Val Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Arg Ile Pro Trp
                85                  90                  95

Thr Phe Gly Gln Gly Thr Lys Val Glu Ile Lys
            100                 105
```

<210> SEQ ID NO 22
<211> LENGTH: 107
<212> TYPE: PRT
<213> ORGANISM: Homo sapiens

<400> SEQUENCE: 22

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Asp Gly Val Pro Ser Arg Phe Ser Gly
50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Arg Ile Pro Trp
                85                  90                  95

Thr Phe Gly Gln Gly Thr Lys Val Glu Ile Lys
            100                 105

<210> SEQ ID NO 23
<211> LENGTH: 107
<212> TYPE: PRT
<213> ORGANISM: Homo sapiens

<400> SEQUENCE: 23

Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Arg Ile Pro Trp
                85                  90                  95

Thr Phe Gly Gln Gly Thr Lys Val Glu Ile Lys
            100                 105

<210> SEQ ID NO 24
<211> LENGTH: 107
<212> TYPE: PRT
<213> ORGANISM: Homo sapiens

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Glu Lys Ala Pro Lys Ser Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Trp Arg Ile Pro Trp
                85                  90                  95

Thr Phe Gly Gln Gly Thr Lys Val Glu Ile Lys
            100                 105

<210> SEQ ID NO 25
<211> LENGTH: 330
<212> TYPE: PRT
<213> ORGANISM: Homo sapiens

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
```

```
            20                  25                  30
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 26
<211> LENGTH: 330
<212> TYPE: PRT
<213> ORGANISM: Homo sapiens

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 27
<211> LENGTH: 106
<212> TYPE: PRT
<213> ORGANISM: Homo sapiens

<400> SEQUENCE: 27

Arg Thr Val Ala Ala Pro Ser Val Phe Ile Phe Pro Ser Asp Glu Gln
  1               5                  10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
        50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105
```

-continued

```
<210> SEQ ID NO 28
<211> LENGTH: 214
<212> TYPE: PRT
<213> ORGANISM: Artificial Sequence
<220> FEATURE:
<223> OTHER INFORMATION: recombinantly produced

<400> SEQUENCE: 28

Asp Ile Gln Met Thr Gln Ser Pro Ala Ser Leu Ser Val Ser Val Gly
  1               5                  10                  15

Glu Thr Val Thr Ile Thr Cys Arg Ala Ser Glu Asn Ile Tyr Ser Asn
             20                  25                  30

Leu Ala Trp Tyr Gln Gln Lys Gln Gly Lys Ser Pro Gln Val Leu Val
         35                  40                  45

Tyr Ala Ala Thr Asn Leu Ala Asp Gly Val Pro Ser Arg Phe Ser Gly
     50                  55                  60

Ser Gly Ser Gly Thr Gln Phe Ser Leu Lys Ile Asn Ser Leu Gln Ser
 65                  70                  75                  80

Glu Asp Phe Gly Asn Tyr Phe Cys Gln His Phe Trp Arg Ile Pro Trp
                 85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 29
<211> LENGTH: 454
<212> TYPE: PRT
<213> ORGANISM: Artificial Sequence
<220> FEATURE:
<223> OTHER INFORMATION: recombinantly produced

<400> SEQUENCE: 29

Asp Val Gln Leu Gln Glu Ser Gly Pro Gly Leu Val Lys Pro Ser Gln
  1               5                  10                  15

Ser Leu Phe Leu Thr Cys Ser Val Thr Gly Tyr Ser Ile Ser Ser Ser
             20                  25                  30

Tyr Tyr Trp Asn Trp Ile Arg Gln Phe Pro Gly Asn Lys Leu Glu Trp
         35                  40                  45

Met Gly Tyr Ile Ser Phe Asp Gly Ser Asn Asn Tyr Asn Pro Ser Leu
     50                  55                  60

Lys Asn Arg Ile Ser Ile Thr Arg Asp Thr Ser Lys Asn Gln Phe Phe
 65                  70                  75                  80

Leu Lys Leu Asn Ser Val Thr Thr Glu Asp Thr Ala Thr Tyr Tyr Cys
```

```
                    85                  90                  95
Ala Arg Glu Lys Glu Asn Tyr Tyr Gly Ser Ser Phe Tyr Tyr Phe Asp
                100                 105                 110

Tyr Trp Gly Ala Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 30
<211> LENGTH: 454
<212> TYPE: PRT
<213> ORGANISM: Artificial Sequence
<220> FEATURE:
<223> OTHER INFORMATION: recombinantly produced
```

<400> SEQUENCE: 30

| | | | | | | | | | | | | | | |
|---|---|---|---|---|---|---|---|---|---|---|---|---|---|---|
| Glu | Val | Gln | Leu | Gln | Glu | Ser | Gly | Pro | Gly | Leu | Val | Lys | Pro | Ser | Gln |
| 1 | | | | 5 | | | | | 10 | | | | | 15 |
| Ser | Leu | Phe | Leu | Thr | Cys | Ser | Val | Thr | Gly | Tyr | Ser | Ile | Ser | Ser | Ser |
| | | | 20 | | | | | 25 | | | | | 30 | | |
| Tyr | Tyr | Trp | Asn | Trp | Ile | Arg | Gln | Phe | Pro | Gly | Asn | Lys | Leu | Glu | Trp |
| | | | 35 | | | | | 40 | | | | | 45 | | |
| Met | Gly | Tyr | Ile | Ser | Phe | Asp | Gly | Ser | Asn | Asn | Tyr | Asn | Pro | Ser | Leu |
| | 50 | | | | | 55 | | | | | 60 | | | | |
| Lys | Asn | Arg | Ile | Ser | Ile | Thr | Arg | Asp | Thr | Ser | Lys | Asn | Gln | Phe | Phe |
| 65 | | | | | 70 | | | | | 75 | | | | | 80 |
| Leu | Lys | Leu | Asn | Ser | Val | Thr | Thr | Glu | Asp | Thr | Ala | Thr | Tyr | Tyr | Cys |
| | | | | 85 | | | | | 90 | | | | | 95 | |
| Ala | Arg | Glu | Lys | Glu | Asn | Tyr | Tyr | Gly | Ser | Ser | Phe | Tyr | Tyr | Phe | Asp |
| | | | 100 | | | | | 105 | | | | | 110 | | |
| Tyr | Trp | Gly | Ala | Gly | Thr | Leu | Val | Thr | Val | Ser | Ser | Ala | Ser | Thr | Lys |
| | | | 115 | | | | | 120 | | | | | 125 | | |
| Gly | Pro | Ser | Val | Phe | Pro | Leu | Ala | Pro | Ser | Ser | Lys | Ser | Thr | Ser | Gly |
| | 130 | | | | | 135 | | | | | 140 | | | | |
| Gly | Thr | Ala | Ala | Leu | Gly | Cys | Leu | Val | Lys | Asp | Tyr | Phe | Pro | Glu | Pro |
| 145 | | | | | 150 | | | | | 155 | | | | | 160 |
| Val | Thr | Val | Ser | Trp | Asn | Ser | Gly | Ala | Leu | Thr | Ser | Gly | Val | His | Thr |
| | | | | 165 | | | | | 170 | | | | | 175 | |
| Phe | Pro | Ala | Val | Leu | Gln | Ser | Ser | Gly | Leu | Tyr | Ser | Leu | Ser | Ser | Val |
| | | | 180 | | | | | 185 | | | | | 190 | | |
| Val | Thr | Val | Pro | Ser | Ser | Ser | Leu | Gly | Thr | Gln | Thr | Tyr | Ile | Cys | Asn |
| | | | 195 | | | | | 200 | | | | | 205 | | |
| Val | Asn | His | Lys | Pro | Ser | Asn | Thr | Lys | Val | Asp | Lys | Lys | Val | Glu | Pro |
| | 210 | | | | | 215 | | | | | 220 | | | | |
| Lys | Ser | Cys | Asp | Lys | Thr | His | Thr | Cys | Pro | Pro | Cys | Pro | Ala | Pro | Glu |
| 225 | | | | | 230 | | | | | 235 | | | | | 240 |
| Leu | Leu | Gly | Gly | Pro | Ser | Val | Phe | Leu | Phe | Pro | Pro | Lys | Pro | Lys | Asp |
| | | | | 245 | | | | | 250 | | | | | 255 | |
| Thr | Leu | Met | Ile | Ser | Arg | Thr | Pro | Glu | Val | Thr | Cys | Val | Val | Val | Asp |
| | | | 260 | | | | | 265 | | | | | 270 | | |
| Val | Ser | His | Glu | Asp | Pro | Glu | Val | Lys | Phe | Asn | Trp | Tyr | Val | Asp | Gly |
| | | | 275 | | | | | 280 | | | | | 285 | | |
| Val | Glu | Val | His | Asn | Ala | Lys | Thr | Lys | Pro | Arg | Glu | Glu | Gln | Tyr | Asn |
| | 290 | | | | | 295 | | | | | 300 | | | | |
| Ser | Thr | Tyr | Arg | Val | Val | Ser | Val | Leu | Thr | Val | Leu | His | Gln | Asp | Trp |
| 305 | | | | | 310 | | | | | 315 | | | | | 320 |
| Leu | Asn | Gly | Lys | Glu | Tyr | Lys | Cys | Lys | Val | Ser | Asn | Lys | Ala | Leu | Pro |
| | | | | 325 | | | | | 330 | | | | | 335 | |
| Ala | Pro | Ile | Glu | Lys | Thr | Ile | Ser | Lys | Ala | Lys | Gly | Gln | Pro | Arg | Glu |
| | | | 340 | | | | | 345 | | | | | 350 | | |
| Pro | Gln | Val | Tyr | Thr | Leu | Pro | Pro | Ser | Arg | Asp | Glu | Leu | Thr | Lys | Asn |
| | | | 355 | | | | | 360 | | | | | 365 | | |
| Gln | Val | Ser | Leu | Thr | Cys | Leu | Val | Lys | Gly | Phe | Tyr | Pro | Ser | Asp | Ile |
| | 370 | | | | | 375 | | | | | 380 | | | | |
| Ala | Val | Glu | Trp | Glu | Ser | Asn | Gly | Gln | Pro | Glu | Asn | Asn | Tyr | Lys | Thr |
| 385 | | | | | 390 | | | | | 395 | | | | | 400 |
| Thr | Pro | Pro | Val | Leu | Asp | Ser | Asp | Gly | Ser | Phe | Phe | Leu | Tyr | Ser | Lys |
| | | | | 405 | | | | | 410 | | | | | 415 | |

```
Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
        450

<210> SEQ ID NO 31
<211> LENGTH: 454
<212> TYPE: PRT
<213> ORGANISM: Artificial Sequence
<220> FEATURE:
<223> OTHER INFORMATION: recombinantly produced

<400> SEQUENCE: 31

Asp Val Gln Leu Gln Glu Ser Gly Pro Gly Leu Val Lys Pro Ser Gln
  1               5                  10                  15

Ser Leu Phe Leu Thr Cys Ser Val Thr Gly Tyr Ser Ile Ser Ser Ser
             20                  25                  30

Tyr Tyr Trp Asn Trp Ile Arg Gln Phe Pro Gly Asn Lys Leu Glu Trp
         35                  40                  45

Met Gly Tyr Ile Ser Phe Asp Gly Ser Asn Asn Tyr Asn Pro Ser Leu
     50                  55                  60

Lys Asn Arg Ile Ser Ile Thr Arg Asp Thr Ser Lys Asn Gln Phe Phe
 65                  70                  75                  80

Leu Lys Leu Asn Ser Val Thr Thr Glu Asp Thr Ala Thr Tyr Tyr Cys
                 85                  90                  95

Ala Arg Glu Lys Glu Asn Tyr Tyr Gly Ser Ser Phe Tyr Tyr Phe Asp
            100                 105                 110

Tyr Trp Gly Ala Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
        210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Ala
        290                 295                 300

Ser Thr Tyr Arg Val Val Ser Val Leu Thr Val Leu His Gln Asp Trp
305                 310                 315                 320
```

```
Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
        340                 345                 350

Pro Gln Val Tyr Thr Leu Pro Pro Ser Arg Asp Glu Leu Thr Lys Asn
    355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 32
<211> LENGTH: 454
<212> TYPE: PRT
<213> ORGANISM: Artificial Sequence
<220> FEATURE:
<223> OTHER INFORMATION: recombinantly produced

<400> SEQUENCE: 32

Glu Val Gln Leu Gln Glu Ser Gly Pro Gly Leu Val Lys Pro Ser Gln
 1               5                  10                  15

Ser Leu Phe Leu Thr Cys Ser Val Thr Gly Tyr Ser Ile Ser Ser Ser
            20                  25                  30

Tyr Tyr Trp Asn Trp Ile Arg Gln Phe Pro Gly Asn Lys Leu Glu Trp
        35                  40                  45

Met Gly Tyr Ile Ser Phe Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Glu Lys Glu Asn Tyr Tyr Gly Ser Ser Phe Tyr Tyr Phe Asp
            100                 105                 110

Tyr Trp Gly Ala Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220
```

-continued

```
Lys Ser Cys Asp Lys Thr His Thr Cys Pro Pro Cys Pro Ala Pro Glu
225             230                 235             240

Leu Leu Gly Gly Pro Ser Val Phe Leu Phe Pro Pro Lys Pro Lys Asp
            245             250             255

Thr Leu Met Ile Ser Arg Thr Pro Glu Val Thr Cys Val Val Val Asp
            260             265             270

Val Ser His Glu Asp Pro Glu Val Lys Phe Asn Trp Tyr Val Asp Gly
        275             280             285

Val Glu Val His Asn Ala Lys Thr Lys Pro Arg Glu Glu Gln Tyr Ala
    290             295             300

Ser Thr Tyr Arg Val Val Ser Val Leu Thr Val Leu His Gln Asp Trp
305             310             315             320

Leu Asn Gly Lys Glu Tyr Lys Cys Lys Val Ser Asn Lys Ala Leu Pro
            325             330             335

Ala Pro Ile Glu Lys Thr Ile Ser Lys Ala Lys Gly Gln Pro Arg Glu
            340             345             350

Pro Gln Val Tyr Thr Leu Pro Pro Ser Arg Asp Glu Leu Thr Lys Asn
        355             360             365

Gln Val Ser Leu Thr Cys Leu Val Lys Gly Phe Tyr Pro Ser Asp Ile
    370             375             380

Ala Val Glu Trp Glu Ser Asn Gly Gln Pro Glu Asn Asn Tyr Lys Thr
385             390             395             400

Thr Pro Pro Val Leu Asp Ser Asp Gly Ser Phe Phe Leu Tyr Ser Lys
            405             410             415

Leu Thr Val Asp Lys Ser Arg Trp Gln Gln Gly Asn Val Phe Ser Cys
            420             425             430

Ser Val Met His Glu Ala Leu His Asn His Tyr Thr Gln Lys Ser Leu
            435             440             445

Ser Leu Ser Pro Gly Lys
    450
```

US 9,023,997 B2

ANTI-ILT5 ANTIBODIES AND ILT5-BINDING ANTIBODY FRAGMENTS

CROSS REFERENCE TO PRIOR APPLICATIONS

This is a U.S. National Phase application under 35 U.S.C. §371 of International Patent Application No. PCT/US2011/021939, filed Jan. 20, 2011, and claims the benefit of U.S. Provisional Patent Application No. 61/296,791, filed Jan. 20, 2010, both of which are incorporated by reference herein in their entirety. The International Application published in English on Jul. 28, 2011 as WO 2011/091177 under PCT Article 21(2).

BACKGROUND

The immune system has evolved multiple mechanisms to preserve immune homeostasis and protective immunity while sparing "self" from autoimmune destruction. The initiation of immunity is a tightly controlled process that relies in part on interplay between inhibitory and activating receptors. Immunoglobulin-like transcripts (ILTs), which encompass both types of receptors, are encoded by rapidly evolving genes found in human and non-human primates. Immunoglobulin-like transcript 5 ("ILT5") is a cell surface molecule that is a member of the immunoglobulin superfamily and is highly expressed on antigen-presenting cells (APCs), such as immature dendritic cells and monocytes.

SUMMARY

Disclosed herein are antibodies and ILT5-binding fragments thereof that specifically bind to ILT5, e.g., human ILT5 (hILT5), on antigen presenting cells (APCs), such as for example, monocytes, macrophages and certain dendritic cells (DC), e.g., myeloid dendritic cells. Also disclosed are pharmaceutical compositions comprising ILT5-binding antibodies and ILT5-binding fragments thereof.

In certain embodiments, compositions provided herein comprise an isolated antibody that binds ILT5 or an ILT5-binding fragment of the antibody, comprising a heavy chain complementarity determining region 1 (VH CDR1) comprising or consisting of the amino acid sequence of SEQ ID NO: 4, a heavy chain complementarity determining region 2 (VH CDR2) comprising or consisting of the amino acid sequence of SEQ ID NO: 5, and a heavy chain complementarity determining region 3 (VH CDR3) comprising or consisting of the amino acid sequence of SEQ ID NO: 6. In certain embodiments, compositions provided herein comprise an isolated antibody that binds ILT5 or an ILT5-binding fragment of the antibody, or consisting of a light chain complementarity determining region 1 (VL CDR1) comprising or consisting of the amino acid sequence of SEQ ID NO: 7, a light chain complementarity determining region 2 (VL CDR2) comprising or consisting of the amino acid sequence of SEQ ID NO: 8, and a light chain complementarity determining region 3 (VL CDR3) comprising or consisting of the amino acid sequence of SEQ ID NO: 9.

In certain embodiments, compositions provided herein comprise an isolated antibody that binds ILT5 or an ILT5-binding fragment of the antibody, comprising a heavy chain complementarity determining region 1 (VH CDR1) consisting of the amino acid sequence of SEQ ID NO: 4, a heavy chain complementarity determining region 2 (VH CDR2) consisting of the amino acid sequence of SEQ ID NO: 5, a heavy chain complementarity determining region 3 (VH CDR3) consisting of the amino acid sequence of SEQ ID NO: 6, a light chain complementarity determining region 1 (VL CDR1) consisting of the amino acid sequence of SEQ ID NO: 7, a light chain complementarity determining region 2 (VL CDR2) consisting of the amino acid sequence of SEQ ID NO: 8, and a light chain complementarity determining region 3 (VL CDR3) consisting of the amino acid sequence of SEQ ID NO: 9.

In certain embodiments, an isolated antibody that binds ILT5 or an ILT5-binding fragment of the antibody comprises at least one human framework region. For example, the anti-ILT5 antibody or ILT5-binding fragment can comprise one or more human heavy chain framework regions such as, without limitation, one or more human heavy chain framework regions from a heavy chain variable region comprising an amino acid sequence selected from the group consisting of the amino acid sequence of SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17. Additionally or alternatively, the anti-ILT5 antibody or ILT5-binding fragment can comprise or more human light chain framework regions such as, without limitation, one or more human light chain framework regions from a light chain variable region comprising an amino acid sequence selected from the group consisting of the amino acid sequence of SEQ ID NO: 18, SEQ ID NO: 19, SEQ ID NO: 20, SEQ ID NO: 21, SEQ ID NO: 22, SEQ ID NO: 23, and SEQ ID NO: 24.

In certain embodiments, an isolated antibody that binds ILT5 or an ILT5-binding fragment of the antibody comprises a heavy chain constant region, e.g., an IgG1 constant region, an IgG2 constant region, an IgG3 constant region, an IgG4 constant region, an IgA constant region, an IgE constant region, an IgM constant region, or an IgD constant region. In certain embodiments, an isolated antibody that binds ILT5 or an ILT5-binding fragment of the antibody comprises a heavy chain constant region comprising the amino acid sequence of SEQ ID NO: 25 or SEQ ID NO: 26.

In certain embodiments, an isolated antibody that binds ILT5 or an ILT5-binding fragment of the antibody comprises a light chain constant region, e.g., kappa light chain constant region or a lambda light chain constant region. In certain embodiments, an isolated antibody that binds ILT5 or an ILT5-binding fragment of the antibody comprises a light chain constant region comprising the amino acid sequence of SEQ ID NO: 27.

In certain embodiments, an isolated antibody that binds ILT5 or an ILT5-binding fragment of the antibody comprises a light chain comprising the amino acid sequence of SEQ ID NO: 28. In certain embodiments, an isolated antibody that binds ILT5 or an ILT5-binding fragment of the antibody comprises a heavy chain comprising the amino acid sequence of SEQ ID NO: 29, SEQ ID NO: 30, SEQ ID NO: 31, or SEQ ID NO: 32. In certain embodiments, an isolated antibody that binds ILT5 or an ILT5-binding fragment of the antibody comprises a light chain comprising the amino acid sequence of SEQ ID NO: 28, and further comprises a heavy chain comprising the amino acid sequence of SEQ ID NO: 29, SEQ ID NO: 30, SEQ ID NO: 31, or SEQ ID NO: 32.

In certain embodiments, an isolated antibody that binds ILT5 or an ILT5-binding fragment of the antibody comprises a light chain variable region comprising the amino acid sequence of SEQ ID NO: 1. In certain embodiments, an isolated antibody that binds ILT5 or an ILT5-binding fragment of the antibody comprises a heavy chain variable region comprising the amino acid sequence of SEQ ID NO: 2 or SEQ ID NO: 3. In certain embodiments, an isolated antibody that binds ILT5 or an ILT5-binding fragment of the antibody comprises a light chain variable region comprising the amino acid sequence of SEQ ID NO: 1, and further comprises a heavy chain variable region comprising the amino acid sequence of SEQ ID NO: 2 or SEQ ID NO: 3.

In certain embodiments, an isolated antibody that binds ILT5 or an ILT5-binding fragment of the antibody comprises a polypeptide having 1-10 amino acid substitutions, deletions or insertions as compared to a polypeptide selected from the group consisting of a heavy chain comprising the amino acid sequence of SEQ ID NO: 29, SEQ ID NO: 30, SEQ ID NO: 31, or SEQ ID NO: 32, a heavy chain variable region comprising the amino acid sequence of SEQ ID NO: 2, SEQ ID NO: 3, SEQ ID NO: 10, SEQ ID NO: 11, SEQ ID NO: 12, SEQ ID NO: 13, SEQ ID NO: 14, SEQ ID NO: 15, SEQ ID NO: 16, or SEQ ID NO: 17, a heavy chain constant region comprising the amino acid sequence of SEQ ID NO: 25 or SEQ ID NO: 26, a light chain comprising the amino acid sequence of SEQ ID NO: 28, a light chain variable region comprising the amino acid sequence of SEQ ID NO: 1, SEQ ID NO: 18, SEQ ID NO: 19, SEQ ID NO: 20, SEQ ID NO: 21, SEQ ID NO: 22, SEQ ID NO: 23, or SEQ ID NO: 24, or a light chain constant region comprising the amino acid sequence of SEQ ID NO: 27. In certain embodiments, at least one substitution comprises a backmutation to a non-human framework residue.

In certain embodiments, an isolated antibody that binds ILT5 or an ILT5-binding fragment of the antibody binds human ILT5. In certain embodiments, an ILT5-binding fragment of an antibody that binds ILT5 comprises a Fab fragment, a F(ab')2 fragment, or a scFv fragment.

Unless otherwise defined, all technical and scientific terms used herein have the same meaning as commonly understood by one skilled in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF THE DRAWINGS

In FIG. 1A, plots depict ILT5 (TRX585) expression by gated $CD56^-CD3^+CD4^+$ or $CD56^-CD3^+CD8^+$ T cells. In FIG. 1B, PBMCs were stained as in (A) and subsequently stained for intracellular Foxp3. Plots show ILT5 expression by gated $CD56^-CD3^+CD4^+$ $Foxp3^+$ or $CD56^-CD3^+CD4^+Foxp3^-$ T cells. FIG. 1C shows ILT5 expression by $CD4^+$, $CD8^+$ or $CD4^-CD8^-$ NKT ($CD56^+$ $CD3^+$) cells. FIG. 1D shows ILT5 expression by myeloid ($CD11c^+HLA\text{-}DR^+$) and plasmacytoid ($CD123^+BDCA\text{-}2^+$) DC cells. FIG. 1E shows expression of ILT5 and CD11b by $CD33^{hi}CD34^-$, $CD33^{hi}CD34^{lo}$ and $CD33^{int}CD34^-$ monocyte subsets as well as by $CD33^{lo}CD34^+$ myeloid progenitors. FIG. 1F shows ILT5 expression by $CD33^{hi}CD34^{lo}CD11b^+$ $CD14^+$ myeloid derived suppressor cells (MDSCs). Percentages of gated cells and mean fluorescence intensity of the ILT5-staining of $ILT5^+$ cells are depicted inside and above plots, respectively. Specificity of the ILT5 staining was ascertained by staining all of the above cell subsets with a mIgG1 isotype control antibody. Data are representative of 4 independent experiments.

Figure 6:
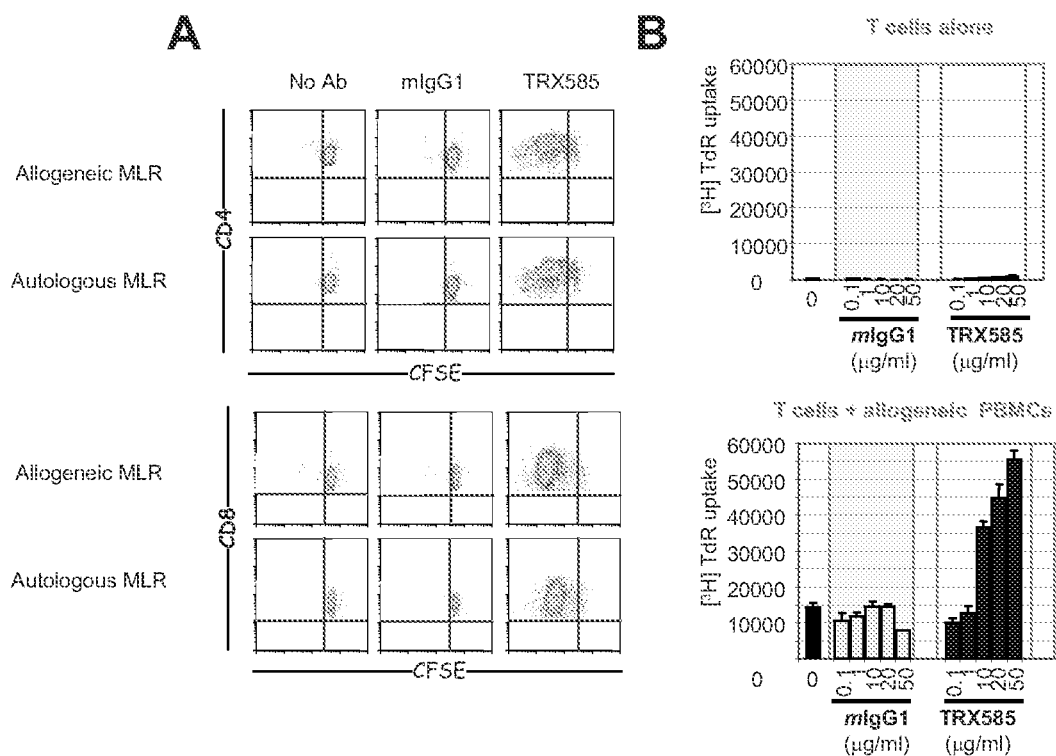
FIG. 6 is a series of two dimensional displays called color density plots (or pseudo-color plots) and bar graphs showing that TRX585 induces the proliferation of the majority of T cells and that this proliferation requires the presence of non-T cells. Color density plots provide the same information as quantile contour plots.

In FIG. 6A, $1\times10^7$ PBMCs per ml were stained with 1 µM CFSE (carboxyfluorescein succinimidyl ester) in PBS 0.1% BSA for 20 min at 37° C., followed by 2 washes in cold PBS. 2×10⁵ CFSE-labeled PBMCs (responder population)/well were cultured with 2×10⁵ mitomycin-treated, allogeneic or autologous PBMCs (stimulator population) in the presence or absence of mIgG1 or TRX585 antibodies (50 µg/ml). Three and a half days later, cells were stained with CD4 and CD8 antibodies as well as the viability dye, 7-amino-actinomycin D (7AAD). Dilution of the CFSE dye in viable CD4 and CD8 T cells, which is indicative of cell proliferation, was examined by flow cytometry. In the experiment shown in FIG. 6B, 1×10⁵ T cells purified from PBMCs were either cultured alone (upper graph) or mixed with 2×10⁵ mitomycin-treated PBMCs (bottom graph), in the presence or absence of the indicated amount of mIgG1 isotype control or TRX585 antibody. T cell proliferation was measured at day 3.5 by means of [$^3$H]TdR-incorporation as reported above. In the experiment shown in FIG. 6B, the X axes indicate the concentration of antibody, while the Y axes indicate [$^3$H]TdR uptake. Shown are the mean±standard error cpm of triplicate wells.

Figure 7:
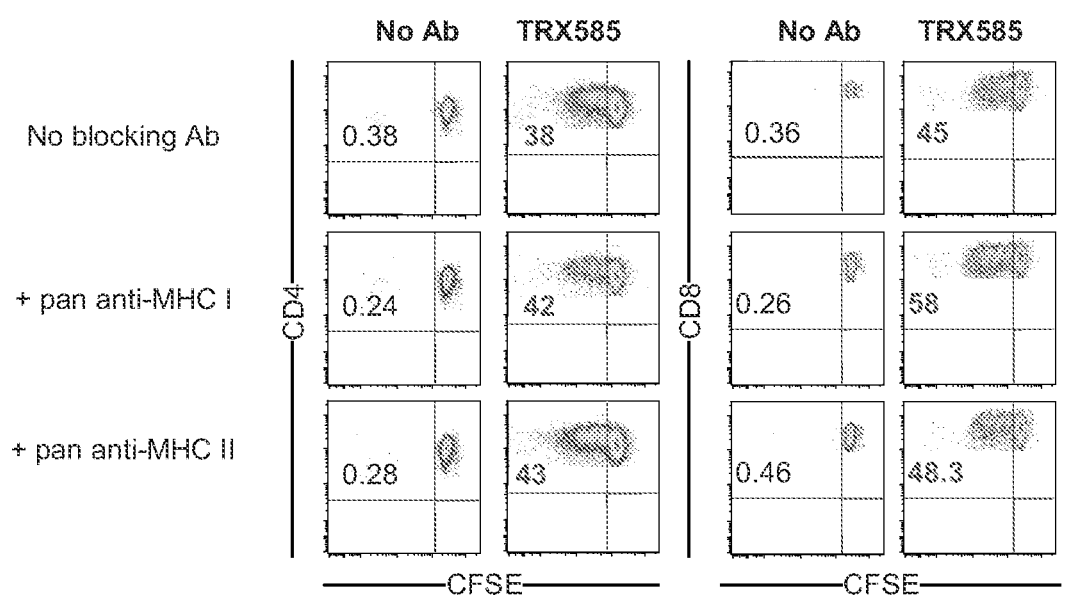

FIG. 7 is a series of FCM pseudo-color plots showing that TRX585 antibody-induced T cell proliferation is TCR-independent. Responder cells (CD4$^+$ and CD8$^+$ T cells) as well as stimulator cells (CD4$^-$ and CD8$^-$ cells) were isolated, using a fluorescence-activated cell sorter (FACSAria), from PBMCs that were stained with CD4 and CD8 antibodies as well as 7AAD (7-aminoactinomycin D). Stimulator cells were inactivated by mitomycin treatment and subsequently incubated with saturating amounts of W6/32 (anti-pan-HLA class I) or Tü39 (anti-pan-HLA class II) or no blocking antibody for 30 minutes at 37° C., followed by washes. Responder cells were CFSE-labeled as previously described. 2×10⁵ CFSE-labeled responder cells were mixed with 2×10⁵ mitomycin-treated stimulator cells in the presence or absence of TRX585 antibody (50 µg/ml). Three and an half days later, CD4 and CD8 T cell proliferation was examined by flow cytometry. Plots show the proliferation of CD4$^+$ T cells (left two columns of plots) and CD8$^+$ T cells (right two columns of plots) in the absence of blocking antibody (top row of plots), or in the presence of pan anti-MHC class I antibody (middle row of plots), and pan anti-MHC class II antibody (bottom row of plots). Percentage of proliferating cells is depicted inside the plots.

Figure 8:
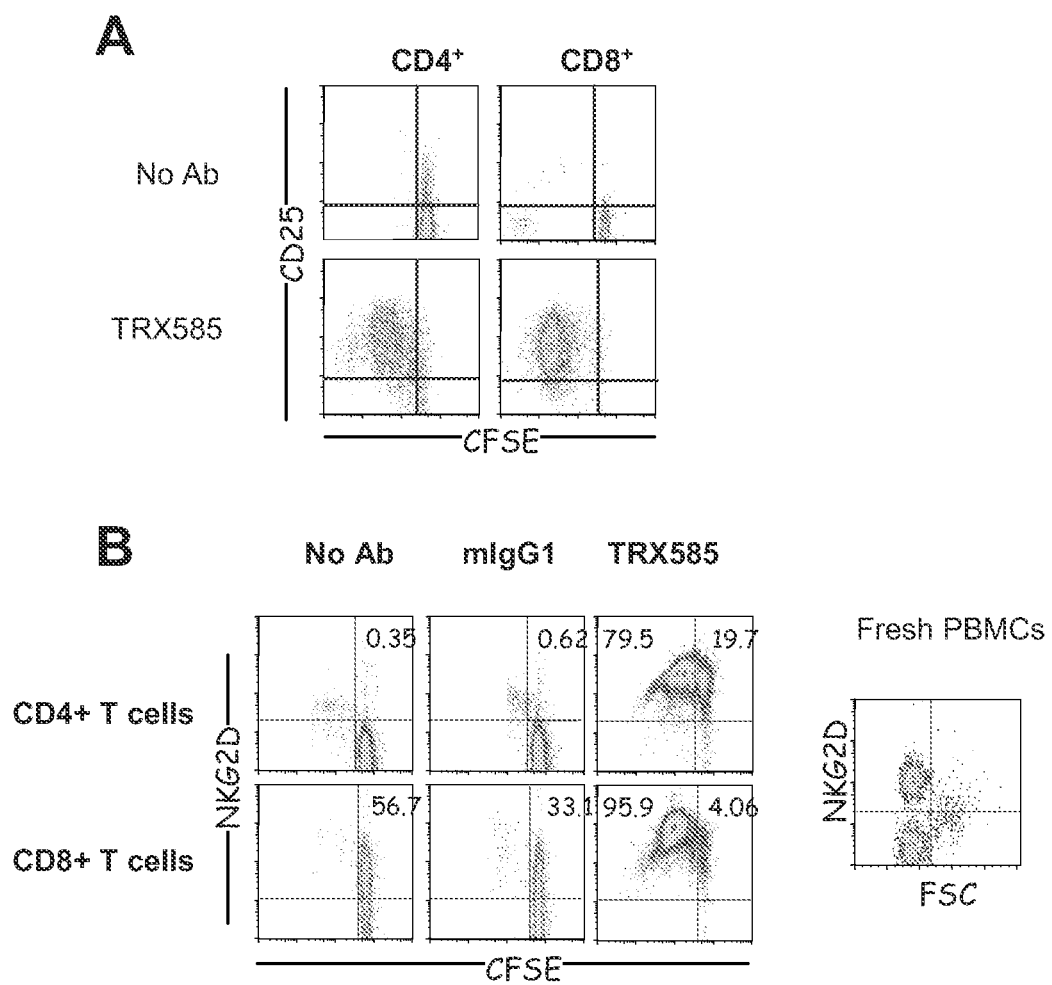

FIG. 8 is a series of FCM pseudo-color plots showing the phenotype of TRX585 antibody-activated T cells. FIG. 8A is a representation of a two-parameter flow cytometry analysis of CFSE-labeled PBMCs that were cultured for 3.5 days with or without TRX585 antibody (50 µg/ml) and subsequently stained with CD4, CD8 and CD25 antibodies. FIG. 8B shows NKG2D expression by PBMCs cultured as previously described and stained with CD4, CD8 and NKG2D antibodies. The plot on the right hand side depicts NKG2D expression by freshly isolated PBMCs. Numbers in plots indicate the proportion of cells within a given quadrant. Dead cells were systematically excluded from the flow cytometry analysis by means of 7AAD staining.

Figure 9:
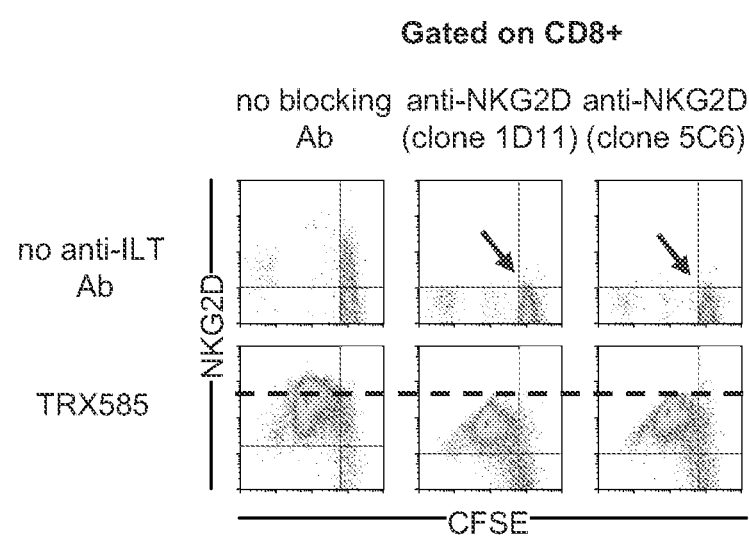

FIG. 9 is a series of FCM pseudo-color plots showing sustained expression of NKG2D by anti-ILT5-exposed T cells despite persistent NKG2D engagement. 2×10⁵ CFSE-labeled PBMCs (responder population)/well were cultured with 2×10⁵ mitomycin-treated, allogeneic PBMCs (stimulator population) in the presence or absence of mIgG1 or TRX585 antibodies (50 µg/ml). When indicated, blocking anti-NKG2D antibodies (clone 1D11 or 5C6) were added to the cultures. In the latter blocking experiments, responder cells were incubated with 20 µg/ml of anti-NKG2D antibodies for 30 min at 37° C. prior to being mixed with stimulator cells. Anti-NKG2D antibodies were present at 10 µg/ml in the final cultures. After three and a half days, cells were stained with NKG2D, CD4 and CD8 antibodies as well as 7AAD, and analyzed by flow cytometry.

Figure 10:
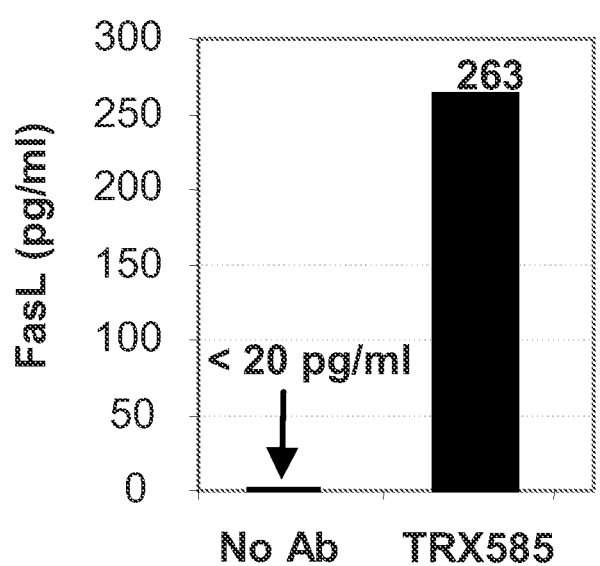

FIG. 10 is a bar graph showing Fas ligand (FasL) secretion by T cells contacted with APCs that have previously been contacted with TRX585 antibodies. 2×10⁵ PBMCs (responder population)/well were cultured with 2×10⁵ mitomycin-treated, allogeneic PBMCs (stimulator population) in the presence or absence of TRX585 antibody (50 µg/ml). Fas ligand was quantified in 24 hour culture supernatants using commercial human Fas ligand-specific ELISA.

Figure 4:
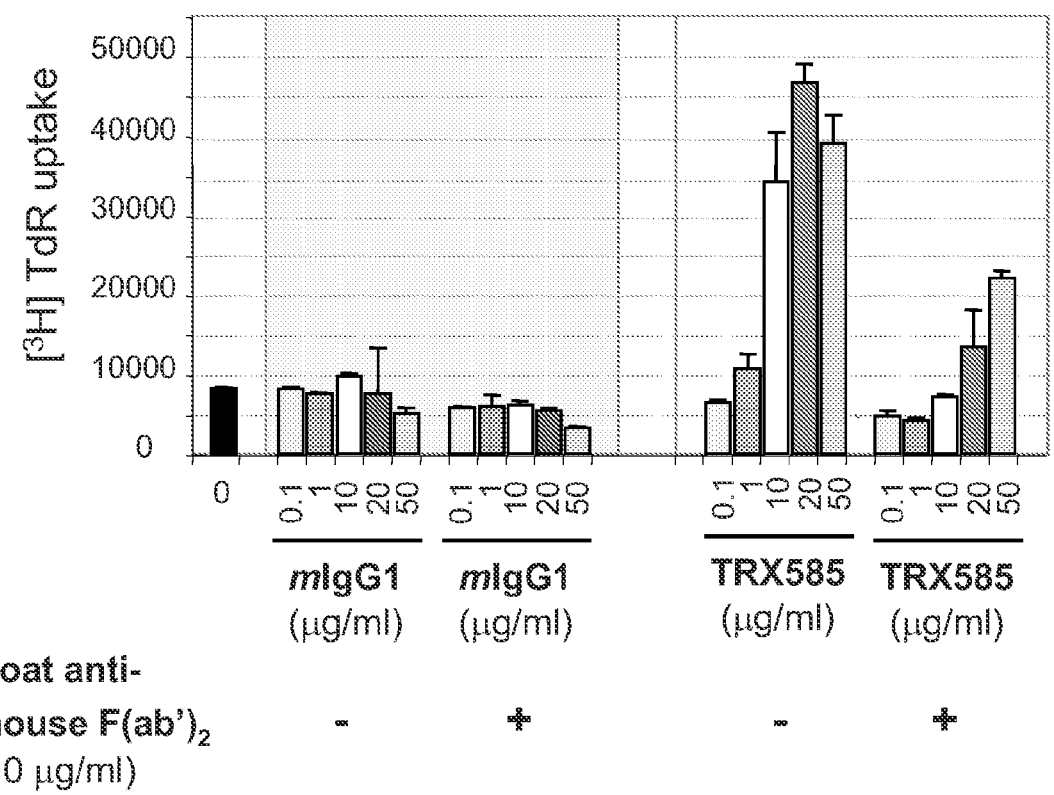
FIG. 4 is a pair of bar graphs showing that monovalent but not divalent TRX585 antibody is endowed with stimulatory potential. $2\times10^5$ PBMCs/well were cultured with $2\times10^5$ mitomycin-treated allogeneic PBMCs in the presence or absence of 10 µg/ml of goat anti-mouse F(ab')2 fragments and various concentrations of soluble TRX585 or mIgG1, as indicated on the figure. [$^3$H]TdR-incorporation (1 µCi/well) in the last 12-18 hours of the cultured was measured at day 3.5. Shown are the mean cpm of triplicate wells.
Figure 11:
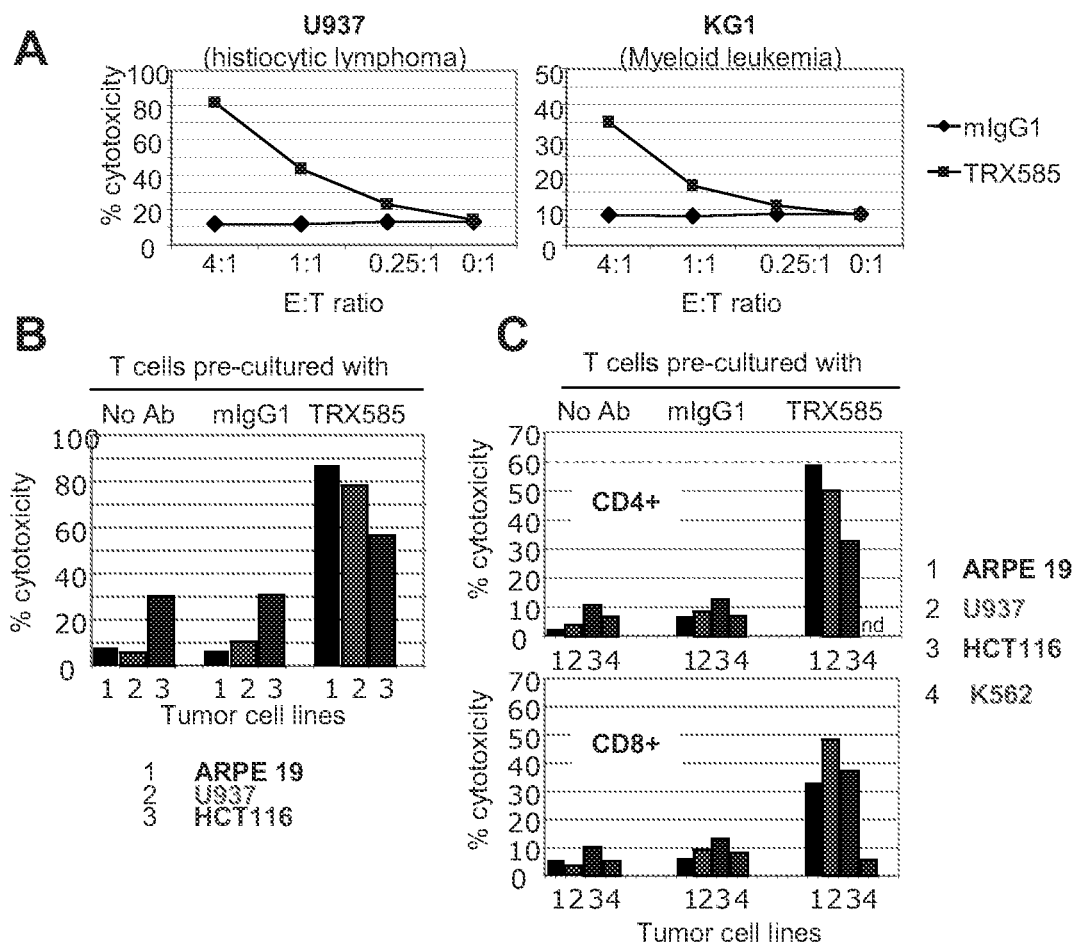

FIG. 11 is a series of line and bar graphs showing that T cells from TRX585 antibody-containing PBMC cultures are cytotoxic to a variety of human tumor cell lines. In the experiment shown in FIG. 11A, 4×10⁵ CFSE-labeled PBMCs were cultured with mIgG1 or TRX585 antibody (50 µg/ml). Three and a half days later, precultured T cells (effector cells) were purified using a FACSAria™, based on CD4 and CD8 expression. On the same day, 50,000 CFSE-labeled U937 and KG1 tumor cells (target cells) per well were mixed with effector cells at effector:target (E:T) ratios of 4:1, 1:1, 0.25:1 and 0:1 and cultured overnight. Cells were subsequently stained with CD3, 7AAD and Annexin V, and occurrence of apoptosis among target cells (CD3$^-$CFSE$^+$ cells) was examined by flow cytometry. The percentage of cytotoxicity was determined by summing the percentage of late apoptotic (7AAD$^+$ Annexin V$^+$) and early apoptotic (7AAD$^-$Annexin V$^+$) cells. The left and right graphs show the percentages of dead U937 and KG1 cells, respectively, when mixed with the indicated proportion of either mIgG1 isotype control (black diamond) or TRX585 (blue squares) antibody-precultured effector T cells. The X axes indicate effector:target ratios. The Y axes indicate percent cytotoxicity. In the experiment shown in FIG. 11B, effector T cells were obtained and assessed for cytotoxic function against ARPE 19, U937, and HCT116 tumor cell lines (E:T=4:1) as described for FIG. 11A. The X axes indicate which tumor cell line was used. The Y axes indicate percent cytotoxicity. In the experiment shown in FIG. 11C, CD4 and CD8 T cells were cell-sorted from 3.5 day-PBMC cultures, set up as described above, and assessed independently for cytotoxic function against ARPE 19, U937, HCT116 and K562 tumor cell lines (E:T=4:1). The X axes and the key to the right of the graphs indicate which tumor cell line was used. The Y axes indicate percent cytotoxicity.

Figure 12:
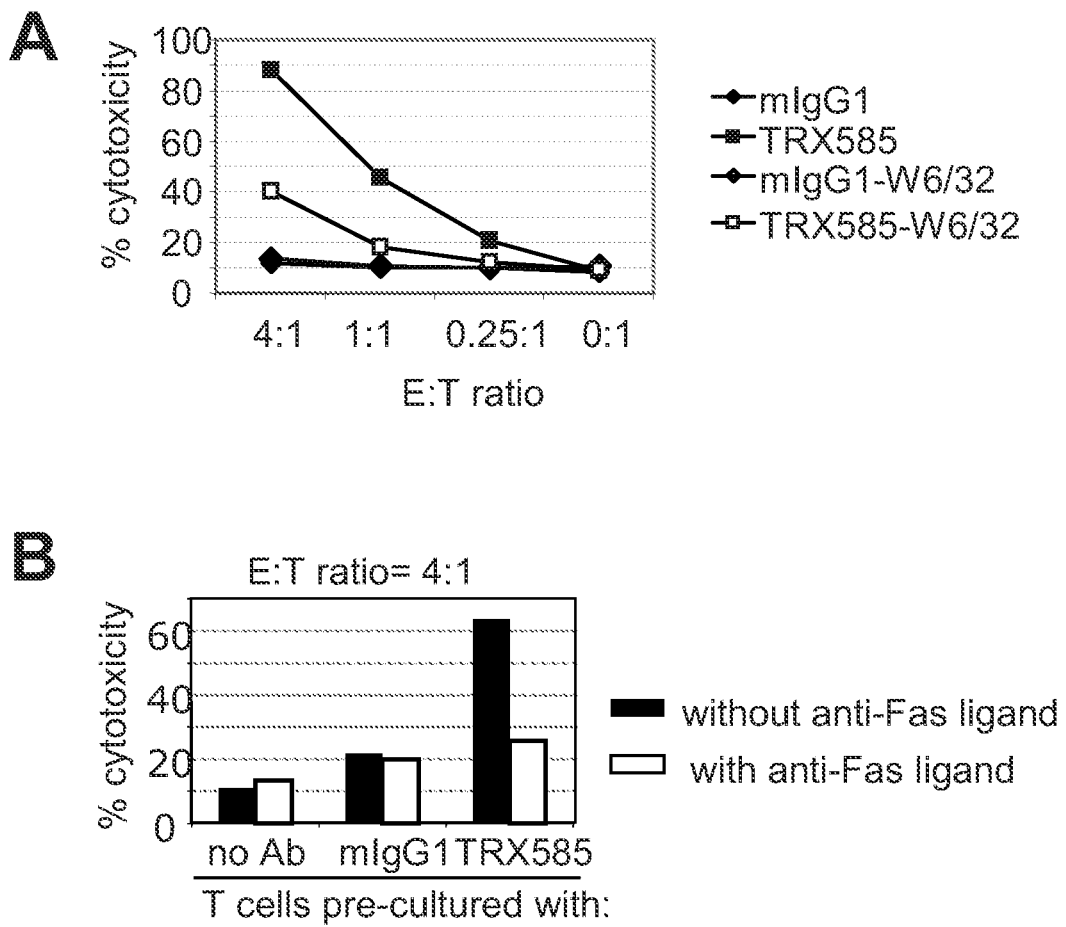

FIG. 12A is a line graph showing that the cytotoxicity of TRX585-preactivated T cells is MHC class I-dependent. FIG. 12B is a bar graph showing that the cytotoxicity of TRX585-preactivated T cells is Fas ligand-dependent. Effector T cells were purified from mIgG1- or TRX585-containing PBMC cultures as well as cultures that did not contain antibodies, and assessed for cytotoxicity against U937 tumor cells according to the experimental procedure described for FIG. 11A. For MHC class I blocking experiments, target cells were incubated with saturating amounts of anti-pan human MHC class I antibody (20 µg/ml; clone W6/32) for 30 min and washed to remove unbound W6/32 antibody before exposure to T cells. To neutralize Fas ligand, 10 µg/ml of blocking anti-human Fas ligand antibody (clone NOK-2) was added to the cocultures of effector and target cells. Data are representative of several experiments using a variety of tumor cell lines and could be recapitulated when using either CD4 or CD8 effector T cells.

Figure 13:
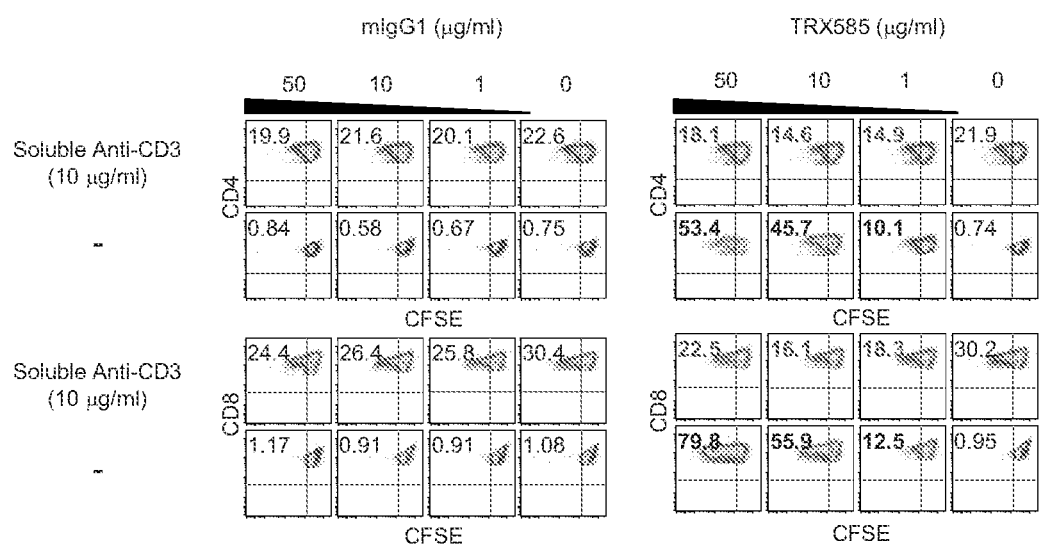

FIG. 13 is a series of FCM pseudo-color plots showing that, while CD4$^+$ and CD8$^+$ T cells from PBMC cultures containing only TRX585 antibodies divided actively, concomitant treatment of PBMCs with anti-CD3 and TRX585 antibodies resulted in the inhibition of T cell proliferation. Here, 4×10⁵

CFSE-labeled PBMCs were cultured with the indicated concentration of either mIgG1 isotype control or TRX585 antibody, in the presence or absence of soluble anti-CD3 antibody (10 μg/ml). Three and an half days later, dilution of the CFSE dye in CD4 and CD8 T cells was examined by flow cytometry. Numbers in plots indicate the proportion of dividing cells. Dead cells were systematically excluded from the flow cytometry analysis by means of 7AAD staining.

Figure 14:
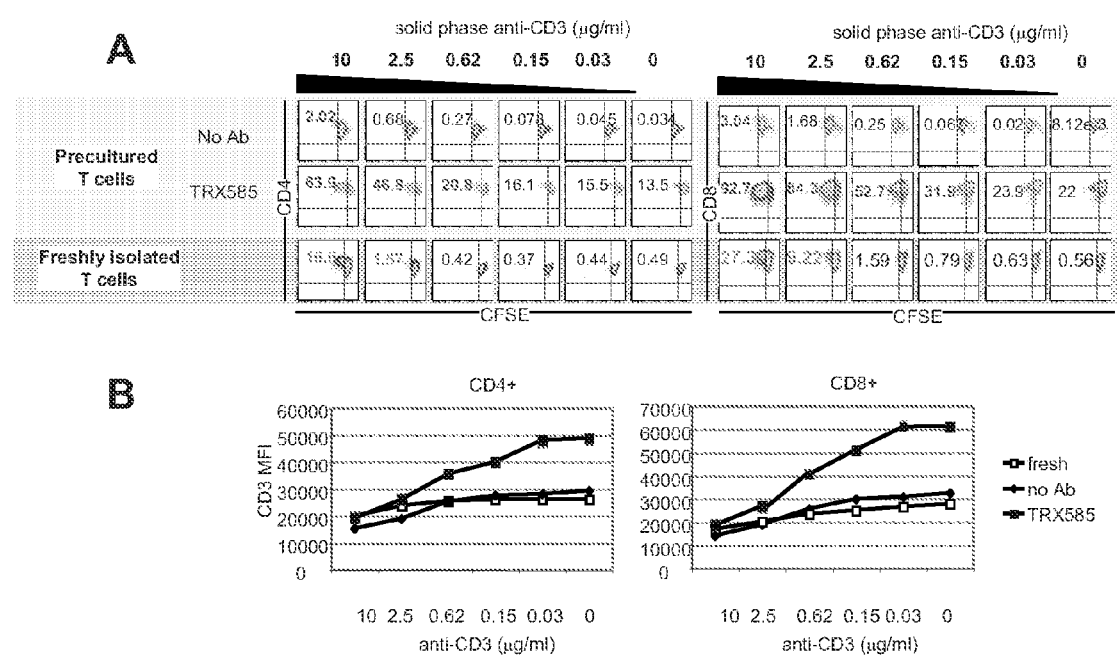

FIG. 14 is a series of FCM pseudo-color plots (FIG. 14A) and line graphs (FIG. 14B) showing that pre-exposure of CD4+ and CD8+ T cells to TRX585 antibodies increases their responsiveness to subsequent TCR stimulation as well as surface CD3 complexes. In the experiment shown in FIG. 14A, 4×10$^5$ CFSE-labeled PBMCs were cultured in the presence or absence of mIgG1 isotype control or TRX585 antibody (50 μg/ml). After 3.5 days, the precultured T cells as well as T cells from freshly isolated autologous PBMCs were cell-sorted using a FACSAria, CFSE-labeled and exposed to anti-CD3 antibody-mediated stimulation for another 2 days. The latter TCR stimulation used solid-phase anti-CD3 antibody at concentrations of 0.03-10 μg/ml. CD4+ and CD8+ T cell proliferation was examined by flow cytometry as described previously. Numbers in plots indicate the proportion of dividing cells. Dead cells were systematically excluded from flow cytometry analyses by means of 7AAD staining. FIG. 14B shows the amount of CD3 complexes at the surface of the same T cells, expressed as the mean fluorescence intensity of the cells when stained with a fluorescent anti-CD3 antibody.

DESCRIPTION OF CERTAIN EMBODIMENTS

Various aspects of the disclosure are described below.
Definitions

"Antibody" as the term is used herein refers to a protein that generally comprises heavy chain polypeptides and light chain polypeptides. Antigen recognition and binding occurs within the variable regions of the heavy and light chains. Single domain antibodies having one heavy chain and one light chain and heavy chain antibodies devoid of light chains are also known. A given antibody comprises one of five types of heavy chains, called alpha, delta, epsilon, gamma and mu, the categorization of which is based on the amino acid sequence of the heavy chain constant region. These different types of heavy chains give rise to five classes of antibodies, IgA (including IgA1 and IgA2), IgD, IgE, IgG (IgG1, IgG2, IgG3 and IgG4) and IgM, respectively. A given antibody also comprises one of two types of light chains, called kappa or lambda, the categorization of which is based on the amino acid sequence of the light chain constant domains. IgG, IgD, and IgE antibodies generally contain two identical heavy chains and two identical light chains and two antigen combining domains, each composed of a heavy chain variable region ($V_H$) and a light chain variable region ($V_L$). Generally IgA antibodies are composed of two monomers, each monomer composed of two heavy chains and two light chains (as for IgG, IgD, and IgE antibodies); in this way the IgA molecule has four antigen binding domains, each again composed of a $V_H$ and a $V_L$. Certain IgA antibodies are monomeric in that they are composed of two heavy chains and two light chains. Secreted IgM antibodies are generally composed of five monomers, each monomer composed of two heavy chains and two light chains (as for IgG and IgE antibodies); in this way the IgM molecule has ten antigen binding domains, each again composed of a $V_H$ and a $V_L$. A cell surface form of IgM also exists and this has two heavy chain/two light chain structure similar to IgG, IgD, and IgE antibodies.

"Chimeric antibody" as the term is used herein refers to an antibody that has been engineered to comprise at least one human constant region. For example, one or all the variable regions of the light chain(s) and/or one or all the variable regions the heavy chain(s) of a mouse antibody (e.g., a mouse monoclonal antibody) may each be joined to a human constant region, such as, without limitation an IgG1 human constant region. Chimeric antibodies are typically less immunogenic to humans, relative to non-chimeric antibodies, and thus offer therapeutic benefits in certain situations. Those skilled in the art will be aware of chimeric antibodies, and will also be aware of suitable techniques for their generation. See, for example, Cabilly et al., U.S. Pat. No. 4,816,567; Shoemaker et al., U.S. Pat. No. 4,978,775; Beavers et al., U.S. Pat. No. 4,975,369; and Boss et al., U.S. Pat. No. 4,816,397, each of which is incorporated herein by reference in its entirety.

"Complementarity determining region" or "CDR" as the terms are used herein refer to short polypeptide sequences within the variable region of both heavy and light chain polypeptides that are primarily responsible for mediating specific antigen recognition. CDRs have been described by Kabat, et al., J. Biol. Chem. 252, 6609-6616 1977; by Chothia, et al., J. Mol. Biol. 196:901-917, 1987; and by MacCallum, et al., J. Mol. Biol. 262:732-745, 1996, each of which is incorporated herein by reference in its entirety. There are three CDRs (termed CDR1, CDR2, and CDR3) within each $V_L$ and each $V_H$.

"Fragment" or "antibody fragment" as the terms are used herein in reference to an antibody refer to a polypeptide derived from an antibody polypeptide molecule (e.g., an antibody heavy or light chain polypeptide) that does not comprise a full length antibody polypeptide, but which still comprises at least a portion of a full length antibody polypeptide. Antibody fragments often comprise polypeptides that comprise a cleaved portion of a full length antibody polypeptide, although the term is not limited to such cleaved fragments. Since a fragment, as the term is used herein in reference to an antibody, encompasses fragments that comprise single polypeptide chains derived from antibody polypeptides (e.g. a heavy or light chain antibody polypeptides), it will be understood that an antibody fragment may not, on its own, bind an antigen. For example, an antibody fragment may comprise that portion of a heavy chain antibody polypeptide that would be contained in a Fab fragment; such an antibody fragment typically will not bind an antigen unless it associates with another antibody fragment derived from a light chain antibody polypeptide (e.g., that portion of a light chain antibody polypeptide that would be contained in a Fab fragment), such that the antigen-binding site is reconstituted. Antibody fragments can include, for example, polypeptides that would be contained in Fab fragments, F(ab')$_2$ fragments, scFv (single chain Fv) fragments, diabodies, linear antibodies, multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and V$_{HH}$ containing antibodies. It will be appreciated that "antibody fragments" or "antibody polypeptide fragments" include "antigen-binding antibody fragments" and "antigen-binding antibody polypeptide fragments." "Antigen-binding antibody fragments" and "antigen-binding antibody polypeptide fragments" include, for example, "ILT5-binding antibody fragments" and "ILT5-binding antibody polypeptide fragments" and "ILT5-binding fragments."

"Framework region" as the term is used herein refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Framework regions are sometimes referred to as "FR."

"Humanized antibody" as the term is used herein refers to an antibody that has been engineered to comprise one or more human framework regions in the variable region together with non-human (e.g., mouse, rat, or hamster) complementarity-determining regions (CDRs) of the heavy and/or light chain. In certain embodiments, a humanized antibody comprises sequences that are entirely human except for the CDR regions. Humanized antibodies are typically less immunogenic to humans, relative to non-humanized antibodies, and thus offer therapeutic benefits in certain situations. Those skilled in the art will be aware of humanized antibodies, and will also be aware of suitable techniques for their generation. See for example, Hwang, W. Y. K., et al., Methods 36:35, 2005; Queen et al., Proc. Natl. Acad. Sci. USA, 86:10029-10033, 1989; Jones et al., Nature, 321:522-25, 1986; Riechmann et al., Nature, 332:323-27, 1988; Verhoeyen et al., Science, 239:1534-36, 1988; Orlandi et al., Proc. Natl. Acad. Sci. USA, 86:3833-37, 1989; U.S. Pat. Nos. 5,225,539; 5,530,101; 5,585,089; 5,693,761; 5,693,762; 6,180,370; and Selick et al., WO 90/07861, each of which is incorporated herein by reference in its entirety.

"Treg" or "regulatory T cell" as the terms are used herein refer to a population of T cells that function to suppress activation of the immune system and thereby maintain immune system homeostasis and tolerance to self-antigens. While a majority of regulatory T cells develops in the thymus, peripheral non-Treg cells can be instructed to commit into the regulatory T cell lineage as well. Regulatory T cells are enriched among cells exhibiting a $CD4^+CD25^{hi}$ or a $CD8^+$ $CD28^-$ phenotype, and many express the forkhead family transcription factor (FOXP3). Regulatory T cells are involved in modulating immune responses in mammalian subjects after their immune systems have successfully responded to foreign antigens, and are also involved in regulating immune responses that may potentially attack the subjects' own tissues, thereby resulting in autoimmune diseases.

ILT5

Immunoglobulin-like transcripts (ILTs) are encoded by rapidly evolving genes found in human and non-human primates. Immunoglobulin-like transcript 5 ("ILT5") is a cell surface molecule that is a member of the immunoglobulin superfamily that includes ILT1, ILT2, ILT3, IL4, ILT5, ILT6, ILT7 and ILT8 (Colonna et al., J. of Exp. Med., Volume 186, Number 11, 1809-1818, 1997, incorporate herein by reference in its entirety). It has been established that the extracellular domain of ILT3, an ILT receptor with inhibitory function, has the capacity to induce T cell hyporesponsiveness (see e.g., US Patent Application Publication No. 2008/0038260, incorporated herein by reference in its entirety). This observation suggests that upon interaction with ILT3, ILT3 ligand expressed by T cells transduces an inhibitory signal.

ILT5 is also an inhibitory ILT receptor and is highly expressed on antigen-presenting cells (APCs), such as immature DCs and monocytes in humans. Human ILT5 gene has been cloned and characterized (see e.g., Colonna et al., J. of Exp. Med., Volume 186, Number 11, 1809-1818, 1997; Pfistershammer et al., Blood, September 10; 114(11):2323-32. Epub 2009 Jul. 17; U.S. Pat. No. 6,448,035, each of which is incorporated herein by reference in its entirety).

Effects of Anti-ILT5 Antibodies and ILT5-Binding Fragments Thereof on Immune Cells Anti-ILT5 antibodies and ILT5-binding fragments thereof for use in the presently disclosed methods induce T cell proliferation when the anti-ILT5 antibodies or ILT5-binding fragments are in monovalent form, but not when the anti-ILT5 antibodies or ILT5-binding fragments are in polyvalent (crosslinked) form. As used in reference to anti-ILT5 antibodies and ILT5-binding fragments described herein, "monovalent" refers to a single molecule of the anti-ILT5 antibody or ILT5-binding fragment that is not crosslinked. For example a soluble anti-ILT5 antibody comprising two antigen-binding sites is "monovalent" as the term is used herein. Without wishing to be bound by theory, we hypothesize that upon interaction of ILT5 ligand-expressing T cells with ILT5-expressing steady state APCs, engagement of the ILT5 ligand by ILT5 induces inhibitory signals that increase the activation threshold of T cells. Alternatively, ILT5:ILT5 ligand engagement may preclude the interaction of ILT5 ligand with an undefined receptor of lower affinity, which would be immunostimulatory. By occupying, as well as inducing some internalization of surface ILT5 molecules, monovalent anti-ILT5 antibodies and ILT5-binding fragments for use in the presently disclosed methods prevent the ILT5 ligand-ILT5 interaction, thereby either removing inhibitory signals or allowing activating signals to take place, either of which would lower the activation threshold of T cells. The fact that monovalent anti-ILT5 antibodies (rather than antibodies immobilized on the plastic bottom of tissue culture wells) can be stimulatory (see Example 3) strongly indicates that ILT5 molecules, which comprise functional inhibitory motifs in their cytoplasmic domain, do not function as inhibitory receptors if not hypercrosslinked. When ILT5 receptors are co-engaged by crosslinked anti-ILT5 antibodies or ILT5-binding fragments (e.g., those bound to Fc receptors on APC or to the bottom of plastic tissue culture wells), they become fully internalized, which precludes ILT5:ILT5 ligand interactions. Furthermore, crosslinked anti-ILT5 antibodies do not enhance T cell activation. This suggests that crosslinked anti-ILT5 antibodies can induce an inhibitory cascade in ILT5-expressing cells (e.g., APCs), which is strong enough to reprogram APCs such that these cells now display a function that counteracts the T cell-specific activation signals (i.e. a tolerogenic function) that occur in the absence of ILT5:ILT5 ligand interactions. Thus, we hypothesize that as a result of the integration of activating and inhibitory signals (due to blockade of ILT5:ILT5 ligand interactions and ILT5 signaling into the APC, respectively), unchanged (opposing signals of similar strength) or diminished immunity can be achieved.

As further described in more detail in the Examples section below, engagement of ILT5 on APCs with monovalent anti-ILT5 antibodies in autologous as well as allogeneic settings results in an upregulation of NKG2D in naïve T cells exposed to such APCs. NKG2D is an immune receptor with an important role in tumor and viral immunity. Moreover, T cells exposed to APCs that had previously been contacted with the anti-ILT5 antibody maintain elevated levels of NKG2D under conditions that normally trigger its internalization. Such conditions typically include contact of NKG2D with its ligand or with an agonist antibody or fragment that binds NKG2D. NKG2D internalization aids tumors and intracellular pathogens (e.g., viruses) in evading recognition by the immune system. Therefore, extending the time of NKG2D expression by appropriate cells of the immune system (e.g., CD4+ and CD8+ T cells) can be advantageous in treating cancer and/or infections with intracellular pathogens. In addition, T cells that proliferate as a result of having interacted with APCs that have been contacted with anti-ILT5 antibodies or ILT5-binding fragments thereof significantly upregulate surface TCR:CD3 complexes and present with markedly increased responsiveness to subsequent TCR stimulation. Upon interaction with APCs that have been or are contacted with the anti-ILT5 antibody, both CD4$^+$ and CD8$^+$ T cells secrete high levels of Fas-ligand and subsequently exert potent, MHC class I- as well as Fas-L-dependent, anti-tumor cytotoxic effects.

In certain embodiments, an anti-ILT5 antibody or an ILT5-binding antibody fragment for use in the presently disclosed methods induces a response in a T cell, e.g., a CD4$^+$ or CD8$^+$ T cell, either in vivo or in vitro, when contacted with an APC, which APC has been or is contacted with the anti-ILT5 antibody or ILT5-binding fragment. In certain embodiments, such a response is a proliferative response and/or a cytokine/chemokine producing response. In certain embodiments, a T cell response (e.g. a proliferative response) is proportional to the amount of anti-ILT5 antibody or ILT5-binding fragment contacted with the APC. In certain embodiments, a T cell response (e.g. a proliferative response) is induced in a T cell that has not been exposed to an antigen (e.g., a naïve T cell). In certain embodiments, the T cell response (e.g. a proliferative response) is induced in a memory T cell that has previously been exposed to an antigen. A T cell response induced by an anti-ILT5 antibody or an ILT5-binding antibody fragment for use in the presently disclosed methods, e.g. a proliferative response, occurs in the absence of TCR recognition of a MHC molecule. Thus, a T cell response mediated by such an anti-ILT5 antibody or ILT5-binding fragment occurs in a TCR-independent manner (e.g., the response does not require recognition of a MHC molecule by a TCR).

In certain embodiments, a T cell, e.g., a CD4$^+$ or CD8$^+$ T cell, either in vivo or in vitro, upregulates expression of NKG2D on its surface when the T cell is contacted with an APC, which APC has been previously contacted with an anti-ILT5 antibody or an ILT5-binding antibody fragment. As used in the present context, the term "upregulate" means that the T cell expresses a protein (e.g., NKG2D on the cell surface) at a higher level than a control T cell contacted with an APC that has not been contacted with the anti-ILT5 antibody or an ILT5-binding antibody fragment. "Upregulates" refers to the condition of expressing more of a given protein (e.g., NKG2D on the cell surface) when the control T cell expresses some level of that protein. "Upregulates" also refers to the condition of expressing any amount, e.g. any detectable amount, of a given protein (e.g., NKG2D on the cell surface) when the control T cell does not expresses that protein at all. In certain embodiments, a T cell maintains expression of NKG2D on its surface under one or more conditions in which the NKG2D is typically internalized from the cell surface. Non-limiting examples of such conditions include engagement of the NKG2D with an NKG2D ligand expressed on the surface of a cell, engagement of the NKG2D with a secreted NKG2D ligand, and engagement of the NKG2D with an antibody or fragment that binds NKG2D.

In certain embodiments, a T cell, e.g., a CD4$^+$ or CD8$^+$ T cell, either in vivo or in vitro, upregulates expression of a TCR and CD3 molecules (e.g., a TCR:CD3 complex) on its surface when the T cell is contacted with an APC, which APC has been previously contacted with an anti-ILT5 antibody or an ILT5-binding antibody fragment. In certain embodiments, a T cell secretes Fas ligand (FasL) at a higher level than a T cell contacted with an APC that has not been contacted with the anti-ILT5 antibody or the ILT5-binding fragment.

In certain embodiments, a T cell or its progeny, e.g., a CD4$^+$ or CD8$^+$ T cell, either in vivo or in vitro, contacted with an APC, which APC has been previously contacted with an anti-ILT5 antibody or an ILT5-binding antibody fragment, exhibits cytotoxic potential. "Cytotoxic potential" as the term is used herein, refers to the state of being able to acquire cytotoxic activity when exposed to an antigen. Thus, in certain embodiments, a T cell or its progeny that exhibits cytotoxic potential (e.g., as a result if having been contacted with an APC that was previously contacted with an anti-ILT5 antibody or an ILT5-binding antibody fragment) is induced to become cytotoxic when exposed to an antigen. A T cell exhibiting cytotoxic potential (e.g., a T cell or its progeny contacted with an APC, which APC has been previously contacted with an anti-ILT5 antibody or an ILT5-binding antibody fragment) may be induced to cytotoxicity upon exposure to any of a variety of antigens. For example, such a T cell may be exposed to a "cellular antigen". As used herein, the term "cellular antigen" refers to an antigen that can be expressed on or in a cell of a subject. The "cellular antigen" can be an exogenous antigen, an endogenous antigen or both. As used herein, the term "exogenous antigen" refers to an antigen that is administered to a subject. The term "exogenous antigen" includes foreign, non-endogenous antigens (see definition of "endogenous antigen" below), as well as antigens that are identical to antigens present in vivo in the body of a subject. As used herein, the term "endogenous antigen" refers to an antigen that is not administered to a subject, e.g., is present in the body of the subject. In certain embodiments, a "cellular antigen" is released upon administration of a therapy (e.g., radiation or a chemotherapeutic agent, as described more fully below). In certain embodiments, a "cellular antigen" comprises an antigen present on or in a tumor cell or an antigen-bearing APC. Alternatively, a "cellular antigen" can be cell-free, so long as it is capable of being expressed on or in a cell of a subject. In certain embodiments, the contact with antigen will generally have occurred at least one hour (e.g., at least two hours, three hours, five hours, ten hours, 15 hours, 24 hours, two days, fours days, one week, two weeks, or longer) after the contact with the anti-ILT5 antibody or ILT5-binding fragment-contacted APC. Contact with any of a variety of antigens will result in the transition from having cytotoxic potential to cytotoxicity. In certain embodiments, a T cell that exhibits cytotoxic potential may become cytotoxic when it binds to or recognizes a cell that is cancerous, or a cell that is infected with a bacterium, a virus, a fungus (including, e.g., a yeast), a protozoan, or a parasite. For example, a T cell that exhibits cytotoxic potential may become cytotoxic when it binds to a cell that is infected with a bacterium, a virus, a fungus, a protozoan, or a parasite. Exemplary antigens of interest include those derived from infectious agents and tumor antigens, wherein an immune response directed against the antigen serves to prevent or treat disease caused by the agent. Such antigens include, but are not limited to, proteins, glycoproteins, lipoproteins, glycolipids, and the like. Antigens of interest also include those which provide therapeutic benefit to a subject who is at risk of acquiring, or who is diagnosed as having, a tumor. In certain embodiments, such antigens are administered to a subject who is at risk of acquiring, or who is diagnosed as having, a tumor. Appropriate antigens include tumor vaccines, proteins, markers and the like that are associated with disease. In certain embodiments, a tumor vaccine introduces a costimulatory protein with the aim of breaking the tolerogenic tumor environment.

Non-limiting examples of tumor antigens include, for example, tumor-associated glycoprotein TAG-72, HER-2, high $M_r$ melanoma antigens that bind to the antibody 9.2.27, Lewis-Y-related carbohydrate (found on epithelial carcinomas), the IL-2 receptor p55 subunit (expressed on leukemia and lymphoma cells), the erbB2/p185 carcinoma-related proto-oncogene (overexpressed in breast cancer), gangliosides (e.g., GM2, GD2, and GD3), epithelial tumor mucin (i.e., MUC-1), carcinoembryonic antigen, ovarian carcinoma antigen MOv-18, squamous carcinoma antigen 17-1A, and malignant melanoma MAGE antigens (e.g., MAGE-1 and MAGE-3), and the like. Those skilled in the art will be aware of other suitable tumor antigens that render cytotoxic T cells or their progeny having cytotoxic potential as described herein.

Non-limiting examples of viral antigens include, but are not limited to, the nucleoprotein (NP) of influenza virus and the Gag proteins of HIV. Other antigens include, but are not limited to, HIV Env protein or its component parts, gp120 and gp41, HIV Nef protein, and the HIV Pol proteins, reverse transcriptase and protease. In addition, other viral antigens such as Ebola virus (EBOV) antigens, such as, for example, EBOV NP or glycoprotein (GP), either full-length or GP deleted in the mucin region of the molecule (Yang Z-Y, et al. (2000) Nat Med 6:886-9, 2000), small pox antigens, hepatitis A, B or C virus, human rhinovirus such as type 2 or type 14, Herpes simplex virus, poliovirus type 2 or 3, foot-and-mouth disease virus (FMDV), rabies virus, rotavirus, influenza virus, coxsackie virus, human papilloma virus (HPV), for example the type 16 papilloma virus, the E7 protein thereof, and fragments containing the E7 protein or its epitopes; and simian immunodeficiency virus (SIV) may be used. An antigen of interest need not be limited to antigens of viral origin. Parasitic antigens, such as, for example, malarial antigens are included, as are fungal antigens, bacterial antigens and tumor antigens. Non-limiting examples of bacterial antigens include: *Bordetella pertussis* (e.g., P69 protein and filamentous haemagglutinin (FHA) antigens), *Vibrio cholerae, Bacillus anthracis, E. coli* antigens such as *E. coli* heat Labile toxin B subunit (LT-B), *E. coli* K88 antigens, and enterotoxigenic *E. coli* antigens, the *Y. enterocolitica* heat shock protein 60 (Mertz et al., J. Immunol. 164(3):1529-1537, 2000) *M. tuberculosis* heat-shock proteins hsp60 and hsp70, *Chlamydia trachomatis* outer membrane protein (Ortiz et al., Infect. Immun. 68(3):1719-1723, 2000), *B. burgdorferi* outer surface protein (Chen et al., Arthritis Rheum. 42(9):1813-1823, 1999); *L. major* GP63 (White et al., Vaccine 17(17):2150-2161, 1999 (and published erratum in Vaccine 17(20-21):2755)), *N. meningitidis* meningococcal serotype 15 PorB protein (Delvig et al., Clin. Immunol. Immunopathol. 85(2); 134-142, 1997), *P. gingivalis* 381 fimbrial protein (Ogawa, J. Med. Microbiol. 41(5):349-358, 1994), *E. coli* outer membrane protein F (Williams et al., Infect. Immun. 68(5):2535-2545, 2000). Other examples of microbial antigens include *Schistosoma mansoni* P28 glutathione S-transferase antigens (P28 antigens) and antigens of flukes, mycoplasma, roundworms, tapeworms, *Chlamydia trachomatis*, and malaria parasites, e.g., parasites of the genus *plasmodium* or *babesia*, for example *Plasmodium falciparum*, and peptides encoding immunogenic epitopes from the aforementioned antigens. Each of the references disclosed above is incorporated herein by reference in its entirety.

Any of a variety of anti-ILT5 antibodies or ILT5-binding antibody fragments that mediate an indirect immunostimulatory effect and/or proliferative response on näive $CD4^+$ or näive $CD8^+$ T cells when such T cells are contacted with an APC that has previously been contacted with the anti-ILT5 antibody or ILT5-binding fragment (e.g., a monovalent form of the anti-ILT5 antibody or ILT5-binding fragment) can be used in the presently disclosed methods. Moreover, any of a variety of anti-ILT5 antibodies or ILT5-binding antibody fragments that results in upregulation of NKG2D or TCR: CD3 complexes in T cells (e.g., näive T cells) exposed to such APCs can be used in the presently disclosed methods. Moreover, any of a variety of anti-ILT5 antibodies or ILT5-binding antibody fragments that endow a T cell or its progeny with cytotoxic potential when the T cell is contacted with an APC that has previously been contacted with the anti-ILT5 antibody or ILT5-binding fragment (e.g., a monovalent form of the anti-ILT5 antibody or ILT5-binding fragment) can be used in the presently disclosed methods. Those of ordinary skill in the art will be able to choose suitable anti-ILT5 antibodies or ILT5-binding fragments thereof for use in the presently disclosed methods. For example, anti-IL5 antibodies and ILT5-binding fragments that can be used in the presently disclosed methods include, but are not limited to, the anti-IL5 antibodies and ILT5-binding fragments described below, e.g., those comprising one or more of SEQ ID NOs: 1-32.

Inhibition of T Cell Responses

In contrast to the immunoenhancing effects described above, APCs that have been previously contacted with crosslinked anti-ILT5 antibodies may be tolerogenic since T cells interacting with such APCs do not mount the T cell response that is observed when monovalent antibody is used. Thus, in certain embodiments, an anti-ILT5 antibody or ILT5-binding fragment thereof for use in the presently disclosed methods might inhibit a response in a T cell, e.g., a $CD4^+$ or $CD8^+$ T cell, either in vivo or in vitro, when contacted with an APC, which APC has been contacted with a crosslinked form of the ant-ILT5 antibody or ILT5-binding fragment, the T cell being contacted with antigen at the same time as or very close in time to the contact of the T cell with the APC previously contacted with the anti-ILT5 antibody or ILT5-binding fragment. As used in reference to inhibition of T cell responses, "very close in time" means within a timeframe where the pharmacodynamic effects of the anti-ILT5 antibodies on the APCs are still exerted. Without wishing to be bound by any particular theory, it is hypothesized that factors such as, but not limited to, the half-life of anti-ILT5 antibodies or ILT5-binding fragments thereof will be important in determining what such timeframe will be. In certain embodiments, such a response is a proliferative response. In certain embodiments, an inhibition of a T cell response (e.g. a proliferative response) is proportional to the amount of crosslinked anti-ILT5 antibody or ILT5-binding fragment contacted with the APC. In certain embodiments, a T cell response (e.g. a proliferative response) is inhibited when the anti-ILT5 antibody or ILT5-binding fragment crosslinks or hypercrosslinks ILT5. As described herein, such hypercrosslinking occurs when the ant-ILT5 antibody or ILT5-binding fragment is in polyvalent form (e.g., bound to a solid support or to Fc receptors (in vivo)), but not when the anti-ILT5 antibody or ILT5-binding fragment is monovalent form.

In certain embodiments, an anti-ILT5 antibody or ILT5-binding antibody fragment for use in the presently disclosed methods is used to induce tolerance in a subject (e.g., a human). For example, an anti-ILT5 antibody or ILT5-binding antibody fragment can be administered to a subject at the same time as or very close in time to an antigen of interest.

Treatment of Diseases and Infections

Treatment Via Induction or Enhancement of a T Cell Response

Monovalent anti-ILT5 antibodies and ILT5-binding antibody fragments such as those described in the section entitled "Effects of Anti-ILT5 Antibodies and ILT5-Binding Fragments Thereof on Immune Cells" indirectly activate both CD4+ and CD8+ T cells in a TCR-independent manner (e.g., activation does not require recognition of a MHC molecule by a TCR), when such T cells are contacted with an APC that has been or still is contacted with the anti-ILT5 antibody or ILT5-binding fragment. Such T cells or their progeny exhibit cytotoxic potential, which cytotoxic potential can be exploited in the treatment of certain conditions by exposing the T cells or their progeny to an antigen, thus rendering the cells cytotoxic. Thus, such anti-ILT5 antibodies and ILT5-binding fragments thereof may be used to treat any of a variety of conditions in a subject (e.g., a human), including but not limited to cancers and infections.

In certain embodiments, anti-ILT5 antibodies and ILT5-binding fragments thereof for use in the presently disclosed methods may be used to treat any of a variety of cancers in a subject. Cancers are characterized by uncontrolled, abnormal growth of cells, and include all types of hyperproliferative growth, hyperplastic growth, oncogenic processes, metastatic tissues or malignantly transformed cells, tissues, or organs, irrespective of histopathologic type or stage of invasiveness. Cancers that can be treated include, but are not limited to, pancreatic cancer, melanomas, breast cancer, lung cancer, bronchus cancer, colorectal cancer, prostate cancer, pancreas cancer, stomach cancer, ovarian cancer, urinary bladder cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, and cancers of hematological tissues.

In certain embodiments, an anti-ILT5 antibody or an ILT5-binding fragment thereof is used in combination with another therapy to treat cancer. For example, an anti-ILT5 antibody or ILT5-binding fragment thereof may be used in combination with radiation therapy. Additionally or alternatively, an anti-ILT5 antibody or ILT5-binding fragment may be used in combination with a chemotherapeutic agent. In certain embodiments, the therapy is administered, at least once, at the same time as or very close in time to administration of the anti-ILT5 antibody or the ILT5-binding fragment. As used in reference to a therapy administered in combination with an anti-ILT5 antibody or ILT5-binding fragment, "very close in time" means within a timeframe within which T cells display pharmacodynamic effects due to the anti-ILT5 antibodies or ILT5-binding fragments.

The timing of therapy administration relative to that of the anti-ILT5 antibody or ILT5-binding fragment administration will take into account several parameters: On one hand, factors that are known to influence the in vivo kinetics of antigen-specific T cell activation and responses, which are initiated in secondary lymphoid tissues (e.g. lymph nodes) through contacts between T cells and antigen-bearing DCs, will be considered. For instance, the abundance, immunogenicity and availability of an antigen are obviously important and dictate whether T cell responses will be initiated, as well as their overall strength and duration. The affinity of a single TCR for a peptide:MHC complex is another parameter. In this regard and without wishing to be bound by any particular theory, we hypothesize that by increasing TCR:CD3 complexes on the surface of T cells, anti-ILT5 antibodies or ILT5-binding fragments thereof increase the avidity of T cells for antigen-bearing DCs and thereby not only permit the recruitment of T cells with low affinity TCRs into a response in which these T cells would otherwise not have participated but also accelerate the overall kinetics of T cell activation. The kinetics of T cell activation also depend on whether DCs acquire the antigen of interest within or outside the lymph nodes (e.g., in the blood stream or a peripheral non-lymphoid tissue). In the latter case, the time required for antigen-bearing DCs to traffic to the lymph nodes increases the timing within which T cell activation occurs relative to the time of antigen exposure. On the other hand, in vitro data show that concomitant TCR stimulation and exposure of CD4+ and CD8+ T cells to anti-ILT5 antibody abrogates anti-ILT5 antibody-induced T cell responsiveness (see FIG. 13). Thus and without wishing to be bound by any particular theory, it is hypothesized that it is desirable to allow the anti-ILT5 antibodies or ILT5-binding fragments to exert their pharmacodynamic effects on T cells prior to the initiation of antigen-specific T cell activation, which activation is induced through antigen exposure by means of therapy administration. In addition, is it desirable to administer the anti-ILT5 antibody or ILT5-binding fragment closer in time to the antigen of interest when the anti-ILT5 antibody or ILT5-binding fragment has a relatively short half-life. Determining the half-life of administered antibodies or antigen-binding fragments is routine in the art, and can be accomplished by a variety of methods including, but not limited to, measuring the amount of antibody or fragment in serum levels (e.g., by ELISA) at various times post administration and fitting such measurements to a half-life curve. Other factors that can influence the length of time between administrations include, without limitation, a patient's physiological reaction or lack thereof to the anti-ILT5 antibody or ILT5-binding fragment, the nature of the therapy and practical considerations such as minimizing the number of clinic visits. Those skilled in the art are aware of the above factors and will be able to determine which timing of therapy administration is appropriate. In certain embodiments a therapy (e.g. radiation or a chemotherapeutic agent) is administered subsequent to administration of the anti-ILT5 antibody or ILT5-binding fragment. For example, a therapy can be administered several hours or days after the anti-ILT5 antibody or ILT5-binding fragment. In other embodiments, a therapy (e.g. radiation or a chemotherapeutic agent) is administered prior to or concomitantly with administration of the anti-ILT5 antibody or ILT5-binding fragment. For example, a therapy can be administered at the same time as, or several hours or days prior to the anti-ILT5 antibody or ILT5-binding fragment.

In certain embodiments, the therapy consists of a bone marrow/hematopoietic cell transplant (BMT/HCT) in a subject with a hematopoietic tumor. In such embodiments, anti-ILT5 antibodies or ILT5-binding fragments thereof may be administered in a subject showing signs of tumor recurrence, thus after to the therapy (BMT/HCT). In the latter case and without wishing to be bound by theory, it is hypothesized that anti-ILT5 antibodies or ILT5-binding fragments thereof will induce and/or enhance T cell responses including those targeting tumor cells. In such embodiments, anti-ILT5 antibodies or ILT5-binding fragments thereof are administered anytime after tumor relapse is diagnosed.

In certain embodiments, administration of a therapy (e.g., radiation or a chemotherapeutic agent) inhibits or prevents the function of cells and/or causes destruction of cells, e.g., acts to lyse or otherwise disrupt (e.g., by inducing apoptosis) cells that comprise an antigen of interest, thereby providing a source of antigen that will activate the cytotoxic potential of a T cell or its progeny that has interacted with an APC contacted with an anti-ILT5 antibody or an ILT5-binding fragment thereof. In certain embodiments, a therapy releases a cellular antigen from a cell (e.g., a tumor cell or a cell infected with a virus), thereby providing a source of antigen that will activate the cytotoxic potential of a T cell that has interacted with an APC contacted with an anti-ILT5 antibody or an ILT5-binding fragment thereof. In certain embodiments, a therapy (e.g. a tumor vaccine) introduces a substantial amount of a tumor antigen, wherein the antigen does not induce sufficient immunity to eradicate tumor cells when expressed endogenously in the tumor environment. In certain embodiments, the tumor vaccine can also introduce costimulatory molecules. When the therapy is administered prior to the antibody or ILT5-binding fragment, it will be understood that the kinetics of the antigen-mediated T cell response may be slower than the kinetics of anti-ILT5 antibody-mediated T cell responses, as described below, and thus cytotoxicity of the T cell towards such an antigen is induced or enhanced. In certain embodiments, anti-ILT5 antibodies and ILT5-binding antibody fragments thereof may be used to treat a subject suffering from a tumor. In certain embodiments, a tumor is poorly immunogenic or even tolerogenic. In such embodiments, an antigen of interest that may potentially trigger cytotoxicity of a T cell as described herein may also be poorly immunogenic or even tolerogenic, e.g., as a result of being in a tumor environment. In certain embodiments, administration of a therapy (e.g., a chemotherapeutic agent or radiation therapy) as described above releases one or more antigens from the tumor in a manner such that the antigen is no longer poorly immunogenic or tolerogenic. As a result, APCs that have previously been bound by and anti-ILT5 antibodies or an ILT5-binding antibody fragment may bind T cells, which T cells can be induced to become cytotoxic upon binding or recognizing an antigen released by the therapy. In certain embodiments, a tumor cell expresses ILT5 receptors, which bind to ILT5 ligands on a T cell that recognizes an antigen on the tumor cell. In such embodiments, ILT5:ILT5 ligand interactions prohibit the activation of the T cell that is bound to the tumor cell. Thus in certain embodiments, administration of anti-ILT5 antibodies or ILT5-binding fragments thereof, with or without therapy, prevents ILT5:ILT5 ligand interactions between the T cell and the tumor cell, which permits the activation of the T cell that is bound to the tumor cell.

In certain embodiments, a therapy is administered until a desired endpoint is reached. For example, a therapy may be administered until a desired level of inhibition of tumor growth, reduction in tumor size, reduction in the number of tumors, decrease in tumor burden, and/or prolonging of survival time is reached. Those skilled in the art will be aware of these and other desired endpoints, and will be able to determine when such an endpoint is reached using standard methods.

A variety of radiation therapies are known in the art, including for example, external beam radiotherapy (EBRT or XBRT) or teletherapy which is applied from outside the body, brachytherapy or sealed source radiotherapy in which sealed radioactive sources are placed in the area under treatment, and systemic radioisotope therapy or unsealed source radiotherapy which is administered by infusion or oral ingestion. A variety of external beam radiotherapies are known, including but not limited to, conventional 2D external beam radiotherapy (2DXRT), stereotactic radiation, 3-dimensional conformal radiotherapy (3DCRT), and intensity-modulated radiation therapy (IMRT). Brachytherapy can employ temporary or permanent placement of radioactive sources. Those skilled in the art will be aware of these and other radiation therapies and will be able to appropriately administer them.

A variety of chemotherapeutic agents are known in the art. In certain embodiments, a chemotherapeutic agent used in combination with an anti-ILT5 antibody or ILT5-binding antibody fragment is an antimetabolite. Non-limiting examples of anti-metabolites include Aminopterin, Methotrexate, Pemetrexed, Raltitrexed, Cladribine, Clofarabine, Fludarabine, Mercaptopurine, Pentostatin, Thioguanine, Capecitabine, Cytarabine, Fluorouracil, Floxuridine, and Gemcitabine. In certain embodiments, an antimetabolite is a nucleoside analogue such as, without limitation, gemcitabine or fluorouracil. In certain embodiments, a chemotherapeutic agent used in combination with an anti-ILT5 antibody or an ILT5-binding fragment thereof is an agent that affects microtubule formation. Non-limiting examples of agents that affects microtubule formation include paclitaxel, docetaxel, vincristine, vinblastine, vindesine, vinorelbin, taxotere, etoposide, and teniposide. In certain embodiments, the chemotherapeutic agent used in combination with an anti-ILT5 antibody or an ILT5-binding fragment thereof is an alkylating agent such as, e.g., cyclophosphamide. In certain embodiments, a chemotherapeutic agent used in combination with an anti-ILT5 antibody or an ILT5-binding fragment thereof is a cytotoxic antibiotic, e.g., a topoisomerase II inhibitor such as doxorubicin. In certain embodiments, a chemotherapeutic agent comprises a toxin such as a small-molecule toxin or an enzymatically active toxin of bacterial, fungal, plant, or animal origin, or fragments thereof. In certain embodiments. a chemotherapeutic agent used in combination with an anti-ILT5 antibody or ILT5-binding fragment is an anti-angiogenic agent such as e.g. avastin. In certain embodiments. a chemotherapeutic agent used in combination with an anti-ILT5 antibody or ILT5-binding fragment thereof is a biologic agent such as e.g. herceptin.

In certain embodiments, anti-ILT5 antibodies and ILT5-binding fragments thereof for use in the presently disclosed methods may be used to treat or prevent (e.g. in combination with vaccination) any of a variety of infections in a subject. Exemplary infections include any of a variety of bacterial (e.g., an intracellular bacterium), viral, fungal, protozoan, or parasitic (e.g., an intracellular parasitic) infections. Viral infections that can be treated include, but are not limited to, infections caused by HIV (e.g., HIV-1 and HIV-2), human herpes viruses, cytomegalovirus (esp. human), rotavirus, epstein-barr virus, varicella zoster virus, hepatitis viruses, such as hepatitis B virus, hepatitis A virus, hepatitis C virus and hepatitis E virus, paramyxoviruses: respiratory syncytial virus, parainfluenza virus, measles virus, mumps virus, human papilloma viruses (for example HPV6, 11, 16, 18 and the like), flaviviruses (e.g. yellow fever virus, dengue virus, tick-borne encephalitis virus, Japanese encephalitis virus), and influenza virus.

Bacterial infections include, but are not limited to, infections caused by *Neisseria* spp, including *N. gonorrhea* and *N. meningitidis*, *Streptococcus* spp, including *S. pneumoniae, S. pyogenes, S. agalactiae, S. mutans; Haemophilus* spp, including *H. influenzae* type B, non typeable *H. influenzae, H. ducreyi; Moraxella* spp, including *M. catarrhalis*, also known as *Branhamella catarrhalis; Bordetella* spp, including *B. pertussis, B. parapertussis* and *B. bronchiseptica; Mycobacterium* spp., including *M. tuberculosis, M. bovis, M. leprae, M. avium, M. paratuberculosis, M. smegmatis; Legionella* spp, including *L. pneumophila; Escherichia* spp, including enterotoxic *E. coli*, enterohemorragic *E. coli*, enteropathogenic *E. coli; Vibrio* spp, including *V. cholera, Shigella* spp, including *S. sonnei, S. dysenteriae, S. flexnerii; Yersinia* spp, including *Y. enterocolitica, Y. pestis, Y. pseudotuberculosis, Campylobacter* spp, including *C. jejuni* and *C. coli; Salmonella* spp, including *S. typhi, S. paratyphi, S. choleraesuis, S. enteritidis; Listeria* spp., including *L. monocytogenes; Helicobacter* spp, including *Hpylori; Pseudomonas* spp, including *P. aeruginosa, Staphylococcus* spp., including *S. aureus, S. epidermidis; Enterococcus* spp., including *E. faecalis, E. faecium; Clostridium* spp., including *C. tetani, C. botulinum, C. difficile; Bacillus* spp., including *B. anthracis; Corynebacterium* spp., including *C. diphtheriae; Borrelia* spp., including *B. burgdorferi, B. garinii, B. afzelii, B. andersonii, B. hermsii; Ehrlichia* spp., including *E. equi* and the agent of the Human Granulocytic Ehrlichiosis; *Rickettsia* spp, including *R. rickettsii; Chlamydia* spp., including *C. trachomatis, C. neumoniae, C. psittaci; Leptsira* spp., including *L. interrogans; Treponema* spp., including *T. pallidum, T. denticola,* and *T. hyodysenteriae.*

In certain embodiments, an anti-ILT5 antibody or an ILT5-binding fragment thereof for use in the presently disclosed methods can be used to induce and/or enhance an immune response in a subject. In such embodiments, the anti-ILT5 antibody or ILT5-binding fragment acts as an adjuvant by inducing or enhancing an immune response (e.g., a cytotoxic cell immune response) against an antigen of interest. For example, a subject may first be administered an anti-ILT5 antibody or an ILT5-binding fragment thereof without concomitant administration of an antigen of interest. Without wishing to be bound by theory, it is hypothesized that such administration endows certain naïve T cells in the subject with cytotoxic potential. Subsequently, a subject may be administered an antigen of interest. Again without wishing to be bound by theory, it is hypothesized that certain T cells exhibiting cytotoxic potential are rendered cytotoxic to cells expressing that antigen of interest upon exposure to the antigen. Thus, in certain embodiments, cytotoxicity of at least one T cell in the subject towards a cell that comprises the antigen is induced or enhanced. In certain embodiments, one or more additional antigens are provided by direct administration of the antigen to the subject. In certain embodiments, an antigen provided by direct administration is the same antigen as is released from a lysed or disrupted cell upon administration of a therapy.

As discussed previously, a suitable length of time between administration of the anti-ILT5 antibody or ILT5-binding fragment and the antigen of interest will depend on various factors, each of which can be determined by those skilled in the art. In certain embodiments, the anti-ILT5 antibody or ILT5-binding fragment can be administered 1-14 days (e.g., 3 days) before administration of the antigen of interest. In certain embodiments, an antigen is administered prior to or concomitantly with administration of the anti-ILT5 antibody or ILT5-binding fragment. For example, a therapy can be administered as the same time as, or several hours or days prior to the anti-ILT5 antibody or ILT5-binding fragment.

In certain embodiments, a subject may be administered an anti-ILT5 antibody or an ILT5-binding antibody fragment at or about the same time as an antigen of interest to induce or enhance an immune response in a subject. As described in more detail herein, a proliferative T cell response is induced in vitro in allogeneic mixed lymphocyte cultures that simultaneously contain both an anti-ILT5 antibody and a foreign antigen present on a foreign lymphocyte. In contrast, anti-ILT5 antibody-induced proliferation of a T cell simultaneously exposed an anti-CD3 antibody-mediated stimulation and an APC that has been affected by an anti-ILT5 antibody is inhibited. Without wishing to be bound by theory, it is possible to reconcile these results by the differential kinetics of the antigen-mediated and anti-ILT5 antibody-mediated T cell responses. T cell proliferation in allogeneic mixed lymphocyte reactions typically occurs at day 5-9 due to the fact that it takes some time for the T cells to establish stable contacts with APCs, which is an essential component of the T cell activation process. In contrast, anti-ILT5 mediated T cell proliferation is detected as soon as 24 hours, and peaks at day 3-3.5, similar to stimulation of T cell proliferation observed with anti-CD3 antibodies. Thus, the kinetics of the antigen-mediated T cell responses are slower than the kinetics of anti-ILT5 antibody-mediated T cell responses. Another possibility, again without wishing to be bound by theory, is that one or more ILT5 ligands and TCR complexes in the mixed lymphocyte culture compete for a molecule that is involved in the observed T cell proliferation.

In certain embodiments, the subject is also administered an adjuvant (e.g., administered with the antigen of interest) to bolster the subject's immune response against the antigen. Suitable adjuvants include, without limitation, CpG, alum, oil-in-water emulsions (e.g., MF59™ (a sub-micron oil-in-water emulsion of a squalene, polyoxyethylene sorbitan monooleate, and sorbitan trioleate), Montanide (Seppic), Adjuvant 65, Lipovant), immune stimulating complexes or ISCOMs (honeycomb-like structures composed of typically *Quillaja* saponins, cholesterol, and phospholipids), QS-21 (a natural product of the bark of the *Quillaja saponaria* tree species), and inulin-based adjuvants.

In certain embodiments, an anti-ILT5 antibody or ILT5-binding antibody fragment is used to induce or enhance an immunostimulatory response in a T cell in vitro, which T cell is then administered to a subject, either alone or in combination with one or more therapeutic agents. For example, PBMCs from a given subject can be cultured with an anti-ILT5 antibody or an ILT5-binding fragment thereof. In these cultures, T cells (e.g., a CD4$^+$ or CD8$^+$ T cell) will interact with APCs that have been contacted with an anti-ILT5 antibody or ILT5-binding fragment thereof and they or their progeny will acquire a cytotoxic potential. The T cell can then be contacted with an antigen of interest, rendering the T cell cytotoxic to cells having the antigen of interest on their surface. This contacting with antigen can be in vitro prior to the administration of the cells to the subject or it can be in vivo after the administration of the cells to the subject. The cytotoxicity of T cells generated by such methods can be evaluated by those skilled in the art according to routine methods. T cells that exhibit suitable cytotoxicity can be be infused in the subject they came from to treat a disease or condition associated with the antigen of interest. Alternatively, a T cell having cytotoxic potential as a result of having been contacted with an APC previously contacted with an anti-ILT5 antibody or ILT5-binding fragment thereof described herein in an autologous setting, or its progeny having such cytotoxic potential, may be infused in the subject it came from, wherein the T cell become cytotoxic upon exposure to an antigen in vivo. In certain embodiments, only CD4$^+$ T cells are made cytotoxic and infused in a subject. In certain embodiments, only CD8$^+$ T cells are made cytotoxic and infused in a subject. In certain embodiments, a population of T cells comprising both CD4$^+$ and CD8$^+$ T cells is made cytotoxic and infused in a subject.

In certain embodiments, a cell is obtained from a subject and a nucleic acid molecule encoding an anti-ILT5 antibody or ILT5-binding antibody fragment is introduced into the cell. For example, the nucleic acid molecule may be operatively linked to a promoter or other sequence that mediates expression of the anti-ILT5 antibody or the ILT5-binding fragment in that cell. In certain embodiments, the nucleic acid molecule may also comprise one or more sequences encoding a polypeptide moiety that mediates secretion, which sequences are operatively linked (e.g., in frame) to the sequences encoding the ant-ILT5 antibody or the ILT5-binding fragment, such that the anti-ILT5 antibody or ILT5-binding fragment is secreted from the cell. Such cells obtained from a subject and containing the introduced nucleic acid molecule, or the progeny of such cells, can then be introduced back into the subject, such that the cell secretes the anti-ILT5 antibody or ILT5-binding antibody fragment in vivo. Naturally, where the progeny of the cells obtained from the subject are used, they also should contain and express the nucleic acid molecule. The cells to be administered back to the subject can optionally be treated so as to prevent or inhibit their proliferation after administration. They can be treated with, for example, an appropriate dose of ionizing radiation (e.g., x- or gamma-irradiation) or a drug such as mitomycin-C.

As will be appreciated by those skilled in the art upon reading the present disclosure, an anti-ILT5 antibody or ILT5-binding antibody fragment produced by cells as described above (e.g., produced by ex vivo methods) will be useful in inducing T cell proliferation, and in inducing T cells to exhibit cytotoxic potential and/or cytotoxicity.

Treatment Via Inhibition of a T Cell Response

In certain embodiments, an anti-ILT5 antibody or an ILT5-binding antibody fragment for use in the presently disclosed methods is used to induce tolerance as described above in order to treat an immune-related disease. "Immune-related disease" as the term is used herein refers to a disease that is associated with at least one abnormal immune phenomenon. For example, one class of immune-related diseases comprises autoimmune diseases. An autoimmune disease typically results when the subject's immune system is activated against one or more components (cells, tissues, or cell/tissue-free molecules) of the subject and attacks that subject's own organs, tissues or cells, instead of attacking, for example, foreign bacteria, viruses and other infectious agents or cancer cells. Every mammalian subject exhibits autoimmunity to some extent, but such autoimmunity normally does not result in a disease state since the immune system regulates and suppresses normal autoimmunity. Autoimmune diseases develop when there is a disruption in the immune system's regulation. Autoimmune diseases can also result when there is a molecular alteration in a subject's cell that is recognized by the immune system, such that the immune system recognizes the altered cell as "foreign."

Another example of an immune-related disease is a disease associated with the effects of organ, tissue, or cell transplantation. Transplanted cells rarely exhibit that same antigens on their surfaces as the recipient subject's endogenous cells. Thus, a transplant subject's immune system often attacks and rejects transplanted solid tissues, which can lead to organ failure or other serious systemic complications. Certain immunosuppressive drugs are typically used to mediate or prevent these immune attacks, but such drugs often cause undesirable side effects, including for example, the risk of developing opportunistic infections as a result of decreased immune responses. Exemplary immune-related diseases include, but are not limited to, adrenergic drug resistance, alopecia greata, ankylosing spondylitis, antiphospholipid syndrome, autoimmune Addison's disease, autoimmune diseases of the adrenal gland, allergic encephalomyelitis, autoimmune hemolytic anemia, autoimmune hepatitis, autoimmune inflammatory eye disease, autoimmune neonatal thrombocytopenia, autoimmune neutropenia, autoimmune oophoritis and orchitis, autoimmune thrombocytopenia, autoimmune thyroiditis, Behcet's disease, bullous pemphigoid, cardiomyopathy, cardiotomy syndrome, celiac sprue-dermatitis, chronic active hepatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, dense deposit disease, diseases associated with effects from organ transplantation, discoid lupus, essential mixed cryoglobulinemia, fibromyalgia-fibromyositis, glomerulonephritis (e.g., IgA nephrophathy), gluten-sensitive enteropathy, Goodpasture's syndrome, GVHD, Graves' disease (including e.g., Graves thyroiditis and Graves ophthalmopathy), Guillain-Barre, hyperthyroidism (i.e., Hashimoto's thyroiditis), idiopathic pulmonary fibrosis, idiopathic Addison's disease, idiopathic thrombocytopenia purpura (ITP), IgA neuropathy, Insulin Resistance Syndrome, juvenile arthritis, lichen planus, lupus erythematosus, Meniere's disease, Metabolic Syndrome, mixed connective tissue disease, multiple sclerosis, Myasthenia Gravis, myocarditis, diabetes (e.g., Type I diabetes or Type II diabetes), neuritis, other endocrine gland failure, pemphigus vulgaris, pernicious anemia, polyarteritis nodosa, polychrondritis, Polyendocrinopathies, polyglandular syndromes, polymyalgia rheumatica, polymyositis and dermatomyositis, post-MI, primary agammaglobulinemia, primary biliary cirrhosis, psoriasis, psoriatic arthritis, Raynauld's phenomenon, relapsing polychondritis, Reiter's syndrome, rheumatic heart disease, rheumatoid arthritis, sarcoidosis, scleroderma, Sjogren's syndrome, stiff-man syndrome, systemic lupus erythematosus, takayasu arteritis, temporal arteritis/giant cell arteritis, ulcerative colitis, urticaria, uveitis, Uveitis Ophthalmia, vasculitides such as dermatitis herpetiformis vasculitis, vitiligo, and Wegener's granulomatosis.

In certain embodiments, a crosslinked anti-ILT5 antibody or an ILT5-binding antibody fragment is administered in combination with another therapeutic agent that induced tolerance. A non-limiting example of such a tolerance-inducing therapeutic agent is an antibody or antigen-binding fragment thereof that binds CD3, e.g., otelixizumab (Keymeulen B, et al. N Engl J. Med.; 352:2598-2608, 2005 incorporated herein by reference in its entirety. Other anti-CD3 antibodies include, without limitation, hOKT3 (humanized (IgG1 or IgG4) anti-human CD3), HUM291 (humanized (IgG2) anti-human CD3; visilizumab; NUVION™), UCHT1 (mouse (IgG1) anti-human CD3), Leu4 (mouse (IgG1) anti-human CD3), 500A2 (hamster (IgG) anti-mouse CD3), CLB-T3/3 (mouse (IgG2a) anti-human CD3), BMA030 (mouse (IgG2a) anti-human CD3), YTH 12.5 (rat (IgG2b) anti-human CD3), and NI-0401 (fully human anti-human CD3). Those skilled in the art will be aware of other anti-CD3 antibodies and fragments that can be used in combination with anti-ILT5 antibodies and ILT5-binding fragments thereof disclosed herein.

In certain embodiments, an anti-ILT5 antibody or an ILT5-binding antibody fragment that is administered to a subject is crosslinked or otherwise aggregated. As indicated above, without wishing to be bound by any particular theory, it is hypothesized that co-engagement of ILT5 receptors by crosslinked anti-ILT5 antibodies and ILT5-binding fragments described herein, initiates an inhibitory cascade in ILT5-expressing APCs, which renders them tolerogenic.

Treatment Generally

In certain embodiments, an anti-ILT5 antibody or ILT5-binding antibody fragment is administered to a subject directly. Routes of administration are described in more detail in the section entitled "Pharmaceutical Compositions." A therapeutically active amount of an anti-ILT5 antibody or ILT5-binding fragment can be administered in an amount effective, at dosages and for periods of time necessary to achieve the desired result. For example, a therapeutically active amount of anti-ILT5 antibody or ILT5-binding fragment thereof may vary according to factors such as the disease state, age, sex, and weight of the subject, and the ability of the anti-ILT5 antibody or ILT5-binding fragment to elicit a desired response in the subject. Dosage regimens can be adjusted to provide the optimum therapeutic response. For example, several divided doses can be administered daily or the dose can be proportionally reduced as indicated by the exigencies of the therapeutic situation. Those skilled in the art will be aware of dosages and dosing regimens suitable for administration of an anti-ILT5 antibody or ILT5-binding fragment to a subject. See e.g., Physicians' Desk Reference, 63rd edition, Thomson Reuters, Nov. 30, 2008, incorporated herein by reference in its entirety.

Those skilled in the art will be aware of other diseases and conditions that can be treated using any of a variety of anti-ILT5 antibodies and ILT5-binding fragments.

Pharmaceutical Formulations

Anti-ILT5 antibodies or ILT5-binding antibody fragments described herein may be formulated for delivery by any available route including, but not limited to parenteral (e.g., intravenous), intradermal, subcutaneous, oral, nasal, bronchial, ophthalmic, transdermal (topical), transmucosal, rectal, and vaginal routes. Anti-ILT5 antibodies or ILT5-binding fragments thereof may include a delivery agent (e.g., a cationic polymer, peptide molecular transporter, surfactant, etc., as described above) in combination with a pharmaceutically acceptable carrier. As used herein the term "pharmaceutically acceptable carrier" includes solvents, dispersion media, coatings, antibacterial and antifugal agents, isotonic and absorption delaying agents, and the like, compatible with pharmaceutical administration. Supplementary active compounds can also be incorporated into pharmaceutical formulations comprising an anti-ILT5 antibody or an ILT5-binding fragment thereof as described herein.

A pharmaceutical composition is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. Pharmaceutical formulations are ideally stable under the conditions of manufacture and storage and should be preserved against the contaminating action of microorganisms such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be advantageous to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the anti-ILT5 antibody or ILT5-binding fragment in the required amount in an appropriate solvent with one or a combination of ingredients enumerated above, as required, followed by filtered sterilization. Generally, dispersions are prepared by incorporating the purified anti-ILT5 antibody or ILT5-binding fragment into a sterile vehicle which contains a basic dispersion medium and the required other ingredients from those enumerated above. In the case of sterile powders for the preparation of sterile injectable solutions, exemplary methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, an anti-ILT5 antibody or an ILT5-binding antibody fragment can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, an anti-ILT5 antibody or an ILT5-binding antibody fragment and a delivery agent are preferably delivered in the form of an aerosol spray from a pressured container or dispenser which contains a suitable propellant, e.g., a gas such as carbon dioxide, or a nebulizer. The present disclosure particularly contemplates delivery of the compositions using a nasal spray, inhaler, or other direct delivery to the upper and/or lower airway. Intranasal administration of DNA vaccines directed against influenza viruses has been shown to induce CD8 T cell responses, indicating that at least some cells in the respiratory tract can take up DNA when delivered by this route, and the delivery agents of the invention will enhance cellular uptake. According to certain embodiments, an anti-ILT5 antibody or ILT5-binding fragment thereof and a delivery agent are formulated as large porous particles for aerosol administration.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the purified polypeptide or protein and delivery agents are formulated into ointments, salves, gels, or creams as generally known in the art.

In certain embodiments, compositions are prepared with carriers that will protect an anti-ILT5 antibody or an ILT5-binding antibody fragment against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, incorporated herein by reference in its entirety.

It is advantageous to formulate oral or parenteral compositions in dosage unit form for ease of administration and uniformity of dosage. "Dosage unit form" as used herein refers to physically discrete units suited as unitary dosages for the subject to be treated; each unit containing a predetermined quantity of active anti-ILT5 antibody or ILT5-binding fragment thereof calculated to produce the desired therapeutic effect in association with the required pharmaceutical carrier.

An anti-ILT5 antibody or an ILT5-binding antibody fragment can be administered at various intervals and over different periods of time as required, e.g., one time per week for between about 1 to 10 weeks, between 2 to 8 weeks, between about 3 to 7 weeks, about 4, 5, or 6 weeks, etc. Those skilled in the art will appreciate that certain factors can influence the dosage and timing required to effectively treat a subject, including but not limited to the severity of the disease or disorder, previous treatments, the general health and/or age of the subject, and other diseases present. Generally, treatment of a subject with an anti-ILT5 antibody or an ILT5-binding antibody fragment as described herein can include a single treatment or, in many cases, can include a series of treatments. It is furthermore understood that appropriate doses may depend upon the potency of the anti-ILT5 antibody or ILT5-binding fragment and may optionally be tailored to the particular recipient, for example, through administration of increasing doses until a preselected desired response is achieved. It is understood that the specific dose level for any particular animal subject may depend upon a variety of factors including the activity of the specific polypeptide or protein employed, the age, body weight, general health, gender, and diet of the subject, the time of administration, the route of administration, the rate of excretion, any drug combination, and the degree of expression or activity to be modulated.

Pharmaceutical formulations as described herein can be included in a container, pack, or dispenser together with instructions for administration.

Detection and Diagnostic Assays

Given their ability to bind to ILT5, anti-ILT5 antibodies and ILT5-binding antibody fragments can be used to detect ILT5 (e.g., in a biological sample, such as serum or plasma), using any of a variety of immunoassays including, but not limited to, enzyme linked immunosorbent assays (ELISAs), radioimmunoassays (RIAs), cell sorting assays (e.g. fluorescent activation cell sorting, or FACS), FCM or tissue immunohistochemistry assays. In certain embodiments, methods for detecting ILT5 (e.g., human ILT5) in a biological sample are provided, certain of such methods comprising contacting a biological sample (e.g. a cell or tissue such as blood) with an anti-ILT5 antibody or ILT5-binding fragment thereof, and detecting either the anti-ILT5 antibody or ILT5-binding fragment bound to ILT5 or unbound antibody or fragment, to thereby detect ILT5 in the biological sample. The anti-ILT5 antibody or ILT5-binding fragment thereof may be directly or indirectly labeled with a detectable label to facilitate detection of the bound or unbound anti-ILT5 antibody or ILT5-binding fragment. Suitable detectable labels include various enzymes, prosthetic labels, fluorescent labels, luminescent labels and radioactive labels. Non-limiting examples of suitable enzymes include horseradish peroxidase, alkaline phosphatase, beta-galactosidase, and acetylcholinesterase. Non-limiting examples of suitable prosthetic labels include streptavidin/biotin and avidin/biotin. Non-limiting examples of suitable fluorescent labels include umbelliferone, fluorescein, fluorescein isothiocyanate, rhodamine, dichlorotriazinylamine fluorescein, dansyl chloride or phycoerythrin. A non-limiting example of a luminescent label includes luminal. Non-limiting examples of suitable radioactive labels include $^{125}I$, $^{131}I$, $^{35}S$ and $^{3}H$.

In certain embodiments, ILT5 can be assayed in a biological sample by a competition immunoassay utilizing ILT5 standards labeled with a detectable substance and an unlabeled anti-ILT5 antibody or ILT5-binding fragment thereof. In such an assay, the biological sample, the labeled ILT5 standards and the anti-ILT5 antibody or ILT5-binding fragment are combined and the amount of labeled ILT5 standard bound to the anti-ILT5 unlabeled antibody or ILT5-binding fragment is determined. The amount of ILT5 in the biological sample is inversely proportional to the amount of labeled ILT5 standard bound to the anti-ILT5 antibody or ILT5-binding.

Other detection assays that utilize antibodies or fragments will be known to those skilled in the art. Any of the antibodies or fragments described herein may be used in accordance with such assays.

Cells

As described in the Examples below, culturing of human PBMCs and anti-ILT5 antibody resulted in the production in the cultures of distinct CD4+ and CD8+ T cells populations. Based on these findings, this disclosure provides the isolated or cultured cells described below in this section.

In certain embodiments, a cell of the present disclosure is a human $CD4^+$ T cell that expresses CD25 and NKG2D (a $CD4^+CD25^+NKG2D^+$ T cell). In certain embodiments, a cell of the present disclosure is a human $CD8^+$ T cell that expresses CD25, and also expresses NKG2D at a level higher than the level of NKG2D observed on steady state natural killer cells ($CD8^+CD25^+$ $NKG2D^{hi}$ T cell). In certain embodiments, such human T cells proliferate in a manner that does not require recognition of a MHC molecule by the T cell, e.g., in a TCR-independent manner (e.g., proliferation does not require recognition of a MHC molecule by a TCR). In certain embodiments, such human T cells secrete Fas ligand (FasL) at a higher level than a naïve T cell. In certain embodiments, such T cells express a TCR:CD3 complex at a higher level than would be observed on a naïve T cell. In certain embodiments, such human T cells express MHC Class II (DR) at a higher level than would be observed on a naïve T cell.

In certain embodiments, a $CD4^+CD25^+NKG2D^+$ or $CD8^+CD25+NKG2D^{hi}$ T cell maintains NKG2D on its cell surface under a condition in which the NKG2D is typically internalized from the cell surface. Non-limiting examples of such conditions include engagement of the NKG2D with an NKG2D ligand expressed on the surface of a cell, engagement of the NKG2D with a secreted NKG2D ligand, and engagement of the NKG2D with an antibody or fragment that binds NKG2D.

In certain embodiments, a CD4+CD25+NKG2D+ or CD8+CD25+ NKG2D$^{hi}$ T cell is produced by a method comprising contacting a naïve T cell with an antigen presenting cell (APC) that has previously been contacted with an anti-ILT5 antibody or an ILT5-binding antibody fragment. In certain embodiments, a CD4+CD25+NKG2D+ or CD8+CD25+ NKG2D$^{hi}$ T cell is produced by a method comprising contacting a memory T cell with an antigen presenting cell (APC) that has previously been contacted with an anti-ILT5 antibody or an ILT5-binding fragment of the antibody in the absence of TCR stimulation.

In certain embodiments, such a CD4+CD25+NKG2D+ or CD8+CD25+NKG2D$^{hi}$ T cell, or its progeny, is endowed with cytotoxic potential, as described herein. In certain embodiments, a CD4+CD25+NKG2D+ or CD8+CD25+ NKG2D$^{hi}$ T cell is induced to become cytotoxic when it binds to or recognizes an antigen. Binding or recognition with any of a variety of antigens will result in the transition from having cytotoxic potential to cytotoxicity. For example, a CD4+CD25+NKG2D+ or CD8+CD25+NKG2D$^{hi}$ T cell that exhibits cytotoxic potential may become cytotoxic when it binds to or recognizes a purified or isolated antigen. Similarly, a CD4+CD25+NKG2D+ or CD8+CD25+NKG2D$^{hi}$ T cell that exhibits cytotoxic potential may become cytotoxic when it binds to or recognizes an unpurified or non-isolated antigen such as, for example, an antigen derived from a cellular lysate, or an antigen present in a blood or serum sample. In certain embodiments, a CD4+CD25+NKG2D+ or CD8+CD25+ NKG2D$^{hi}$ T cell having cytotoxic potential is induced to become cytotoxic when the cell binds to or recognizes a cancerous cell, or a cell that is infected with a bacterium, a virus, a fungus, a protozoan, or a parasite. In certain embodiments, a CD4+CD25+NKG2D+ or CD8+CD25+ NKG2D$^{hi}$ T cell having cytotoxic potential is induced to become cytotoxic when the cell binds to or recognizes an antigen present on a cancerous cell, or a cell that is infected with a bacterium, a virus, a fungus, a protozoan, or a parasite.

In certain embodiments, in cell cultures comprising a CD4+CD25+NKG2D+ or CD8+CD25+ NKG2D$^{hi}$ T cell the cytokines TNF-alpha (tumor necrosis factor alpha) and IL5, and/or the chemokines, Rantes, IP-10 (interferon-inducible protein 10), or MIP-1 (macrophage inflammatory protein 1) are produced. In certain embodiments, a CD4+CD25+ NKG2D+ or CD8+CD25+ NKG2D$^{hi}$ T cell present in such a cell culture produces one or more of Rantes, IP-10, TNF-alpha, IL5, or MIP-1 itself. In certain embodiments, a CD4+CD25+NKG2D+ or CD8+CD25+ NKG2D$^{hi}$ T cell in a cell culture induces another type of cell in the culture to produce one or more of Rantes, IP-10, TNF-alpha, IL5, or MIP-1. For example, a CD4+CD25+NKG2D+ or CD8+CD25+ NKG2D$^{hi}$ T cell can induce one or more of a monocyte, a macrophage, a T cell other than CD4+CD25+NKG2D+ or CD8+CD25+ NKG2D$^{hi}$ T cell, a B cell, a mast cell, an endothelial cell, and/or a fibroblast to produce one or more of Rantes, IP-10, TNF-alpha, IL5, or MIP-1. Thus, methods of using CD4+CD25+NKG2D+ or CD8+CD25+ NKG2D$^{hi}$ cells for inducing the production of these soluble mediators (cytokine and chemokines) by these cell types (monocytes, macrophages, T cells other than CD4+CD25+NKG2D+ or CD8+CD25+NKG2D$^{hi}$ T cells, or B cells) are provided.

CD4+CD25+NKG2D+ or CD8+CD25+ NKG2D$^{hi}$ T cells as described in this section may be used in any of a variety of applications, including any of the applications described in the section entitled "Treatment of Diseases and Infections" above.

Anti-ILT5 Antibodies and ILT5-Binding Fragments Thereof

Disclosed herein are a variety of anti-ILT5 antibodies and ILT5-binding antibody fragments thereof. In certain embodiments, an anti-ILT5 antibody or an ILT5-binding antibody fragment thereof can be used for one or more applications described herein (e.g., inducing an immunostimulatory response in T cells, thereby causing them to proliferate or display a cytotoxic function). In certain embodiments, such T cells produce cytokines and/or induce other cells to produce cytokines and/or chemokines. In certain embodiments, such T cells may be used in the treatment of various diseases or infections. In certain embodiments, the antibody is monoclonal. In certain embodiments, an anti-ILT5 antibody or an ILT5-binding antibody fragment is chimeric in that it contains human heavy and/or light chain constant regions. See, for example, Cabilly et al., U.S. Pat. No. 4,816,567; Shoemaker et al., U.S. Pat. No. 4,978,775; Beavers et al., U.S. Pat. No. 4,975,369; and Boss et al., U.S. Pat. No. 4,816,397, each of which is incorporated herein by reference in its entirety. In certain embodiments, an anti-ILT5 antibody or ILT5-binding fragment thereof is humanized in that it contains one or more human framework regions in the variable region together with non-human (e.g., mouse, rat, or hamster) complementarity-determining regions (CDRs) of the heavy and/or light chain. Humanized antibodies can be produced using recombinant DNA techniques well known to those skilled in the art. See for example, Hwang, W. Y. K., et al., Methods 36:35, 2005; Queen et al., Proc. Natl. Acad. Sci. USA, 86:10029-10033, 1989; Jones et al., Nature, 321:522-25, 1986; Riechmann et al., Nature, 332:323-27, 1988; Verhoeyen et al., Science, 239: 1534-36, 1988; Orlandi et al., Proc. Natl. Acad. Sci. USA, 86:3833-37, 1989; U.S. Pat. Nos. 5,225,539; 5,530,101; 5,585,089; 5,693,761; 5,693,762; 6,180,370; and Selick et al., WO 90/07861, each of which is incorporated herein by reference in its entirety.

In certain embodiments, a fragment (e.g., an antigen-binding fragment) is derived from a whole antibody molecule, such as a monoclonal or a polyclonal antibody. The antibody can be, e.g., cleaved on the carboxy terminal side of its hinge region (e.g., with pepsin) to generate a F(ab')$_2$ fragment, or on the amino terminal side of its hinge region (e.g., with papain) to generate Fab fragments. In certain embodiments, an anti-ILT5 antibody or an ILT5-binding antibody fragment binds human ILT5.

In certain embodiments, an anti-ILT5 antibody fragment is a Fab fragment, a F(ab')$_2$ fragment, a scFv fragment, a diabody, a linear antibody, a multispecific antibody fragment such as a bispecific, a trispecific, or a multispecific antibody (e.g., a diabody, a triabody, a tetrabody), a minibody, a chelating recombinant antibody, a tribody or bibody, an intrabody, a nanobody, a small modular immunopharmaceutical (SMIP), a binding-domain immunoglobulin fusion protein, a camelid antibody, or a V$_{HH}$ containing antibody. Those skilled in the art will be aware of how to engineer or construct such antibodies or fragments without undue experimentation.

In certain embodiments, an anti-ILT5 antibody or an ILT5-binding antibody fragment thereof comprises a light chain variable region comprising the amino acid sequence of SEQ ID NO: 1 [DIQMTQSPASLSVSVGETVTITCRAS-ENIYSNLAWYQQKQGKSPQVLVYAATNLADGV PSRFSGSGSGTQFSLKINSLQSEDFGNY-FCQHFWRIPWTFGGGTKLEIK]. In certain embodiments, an anti-ILT5 antibody or an ILT5-binding antibody fragment comprises a heavy chain variable region comprising the amino acid sequence of SEQ ID NO: 2 [DVQLQESGPGLVKPSQSLFLTCSVTGYSISSSYYWNWIRQFPGNKLEWMGYISFDGSNN YNPSLKNRISITRDTSKNQFFLKLNSVTTEDTATYYCAREKENYYGSSFYYFDYWGLGT SLTVSS]. In certain embodiments, an anti-ILT5 antibody or an ILT5-binding antibody fragment comprises a heavy chain variable region comprising the amino acid sequence of SEQ ID NO: 3 [EVQLQESGPGLVKPSQSLFLTCSVTGYSISSSYYWNWIRQFPGNKLEWMGYISFDGSNN YNPSLKNRISITRDTSKNQFFLKLNSVTTEDTATYYCAREKENYYGSSFYYFDYWGLGT SLTVSS].

In certain embodiments, an anti-ILT5 antibody or ILT5-binding fragment thereof comprises a light chain variable region comprising the amino acid sequence of SEQ ID NO: 1 and a heavy chain variable region comprising the amino acid sequence of SEQ ID NO: 2. In certain embodiments, an anti-ILT5 antibody or ILT5-binding fragment thereof comprises a light chain variable region comprising the amino acid sequence of SEQ ID NO: 1 and a heavy chain variable region comprising the amino acid sequence of SEQ ID NO: 3.

In certain embodiments, an anti-ILT5 antibody or an ILT5-binding antibody fragment, e.g., a humanized or chimeric antibody or fragment, comprises one or more of the following CDRs: SEQ ID NO: 4 [SSYYWN](VH CDR1), SEQ ID NO: 5 [YISFDGSNNYNPSLKN](VH CDR2), SEQ ID NO: 6 [EKENYYGSSFYYFDY](VH CDR3), SEQ ID NO: 7 [RASENIYSNLA](VL CDR1), SEQ ID NO: 8 [AATNLAD](VL CDR2), and SEQ ID NO: 9 [QHFWRIPWT](VL CDR3).

In certain embodiments, an anti-ILT5 antibody or an ILT5-binding antibody fragment, e.g., a humanized or chimeric antibody or fragment, comprises a heavy chain variable region (VH) comprising: a VH CDR1 comprising the amino acid sequence of SEQ ID NO: 4, a VH CDR2 comprising the amino acid sequence of SEQ ID NO: 5, and a VH CDR3 comprising the amino acid sequence of SEQ ID NO: 6. In certain embodiments, an anti-ILT5 antibody or ILT5-binding fragment thereof, e.g., a humanized or chimeric antibody or fragment, comprises a light chain variable region (VL) comprising: a VL CDR1 comprising the amino acid sequence of SEQ ID NO: 7, a VL CDR2 comprising the amino acid sequence of SEQ ID NO: 8, and a VL CDR3 comprising the amino acid sequence of SEQ ID NO: 9. In certain embodiments, an anti-ILT5 antibody or an ILT5-binding antibody fragment, e.g., a humanized or chimeric antibody or fragment, comprises a heavy chain variable region comprising: a VH CDR1 comprising the amino acid sequence of SEQ ID NO: 4, a VH CDR2 comprising the amino acid sequence of SEQ ID NO: 5, a VH CDR3 comprising the amino acid sequence of SEQ ID NO: 6, a VL CDR1 comprising the amino acid sequence of SEQ ID NO: 7, a VL CDR2 comprising the amino acid sequence of SEQ ID NO: 8, and a VL CDR3 comprising the amino acid sequence of SEQ ID NO: 9.

In certain embodiments, an anti-ILT5 antibody or an ILT5-binding antibody fragment comprises a heavy chain variable region comprising: a VH CDR1 consisting of the amino acid sequence of SEQ ID NO: 4, a VH CDR2 consisting of the amino acid sequence of SEQ ID NO: 5, and a VH CDR3 consisting of the amino acid sequence of SEQ ID NO: 6. In certain embodiments, an anti-ILT5 antibody or an ILT5-binding antibody fragment comprises a light chain variable region comprising: a VL CDR1 consisting of the amino acid sequence of SEQ ID NO: 7, a VL CDR2 consisting of the amino acid sequence of SEQ ID NO: 8, and a VL CDR3 consisting of the amino acid sequence of SEQ ID NO: 9.

In certain embodiments, an anti-ILT5 antibody or an ILT5-binding antibody fragment comprises a heavy chain variable region comprising: a VH CDR1 comprising the amino acid sequence of SEQ ID NO: 4, a VH CDR2 comprising the amino acid sequence of SEQ ID NO: 5, a VH CDR3 comprising the amino acid sequence of SEQ ID NO: 6, a VL CDR1 consisting of the amino acid sequence of SEQ ID NO: 7, a VL CDR2 consisting of the amino acid sequence of SEQ ID NO: 8, and a VL CDR3 consisting of the amino acid sequence of SEQ ID NO: 9. In certain embodiments, an anti-ILT5 antibody or an ILT5-binding antibody fragment comprises a heavy chain variable region comprising: a VH CDR1 consisting of the amino acid sequence of SEQ ID NO: 4, a VH CDR2 consisting of the amino acid sequence of SEQ ID NO: 5, a VH CDR3 consisting of the amino acid sequence of SEQ ID NO: 6, a VL CDR1 comprising the amino acid sequence of SEQ ID NO: 7, a VL CDR2 comprising the amino acid sequence of SEQ ID NO: 8, and a VL CDR3 comprising the amino acid sequence of SEQ ID NO: 9. In certain embodiments, an anti-ILT5 antibody or an ILT5-binding antibody fragment thereof comprises a heavy chain variable region comprising: a VH CDR1 consisting of the amino acid sequence of SEQ ID NO: 4, a VH CDR2 consisting of the amino acid sequence of SEQ ID NO: 5, a VH CDR3 consisting of the amino acid sequence of SEQ ID NO: 6, a VL CDR1 consisting of the amino acid sequence of SEQ ID NO: 7, a VL CDR2 consisting of the amino acid sequence of SEQ ID NO: 8, and a VL CDR3 consisting of the amino acid sequence of SEQ ID NO: 9.

In certain embodiments, an anti-ILT5 antibody or an ILT5-binding antibody fragment thereof is humanized in that it comprises one or more human framework regions, e.g. a human heavy chain framework region and/or a human light chain framework region. In certain embodiments, an anti-ILT5 antibody or an ILT5-binding antibody fragment comprises one or more human framework regions from a heavy chain variable region comprising an amino acid sequence selected from the group consisting of the amino acid sequence of SEQ ID NO: 10 [QVQLQESGPGLVKPPGTLSLTCAVSGGSISSSYYWNWVRQPPGKGLEWIGYISFDGSNNYNPSLKNRVTISVDKSKNQFSLKLSSVTAADTAVYCCAREKENYYGSSFYYFDYWGQG TLVTVSS], SEQ ID NO: 11 [QVQLQESGPGLVKPSGTLSLTCAVSGGSISSSYYWNWVRQPPGKGLEWIGYISFDGSNNYNPSLKNRVTISVDKSKNQFSLKLSSVTAADTAVYCCAREKENYYGSSFYYFDYWGQG TLVTVSS], SEQ ID NO: 12 [QVQLQESGPGLVKPPGTLSLTCAVSGGSISSSYYWNWVRQPPGKGLEWIGYISFDGSNNYNPSLKNRVTISVDKSKNQFSLKLSSVTAADTAVYYCAREKENYYGSSFYYFDYWGQG TLVTVSS], SEQ ID NO: 13 [QVQLQESGPGLVKPSDTLSLTCAVSGYSISSSYYWNWIRQPPGKGLEWIGYISFDGSNNYNPSLKNRVTMSVDTSKNQFSLKLSSVTAVDTAVYYCAREKENYYGSSFYYFDYWGQ GTLVTVSS], SEQ ID NO: 14 [QLQLQESGPGLVKPSETLSLTCTVSGGSIS SSYYWNWIRQPPGKGLEWIG YISFDGSNNYNPSLKNRVTISVDTSKNQFSLKLSSVTA ADTAVYYCAREKENYYGSSFYYFDYWGQGT LVTVSS], SEQ ID NO: 15 [QVQLQESGPGLVKPSETLSLTCTVSGGSIS SSYYWNWIRQPPGKGLEWIG YISFDGSNNYNPSLKNRVTISVDTSKNQFSLKLSSVTA ADTAVYYCAREKENYYGSSFYYFDYWGQGT LVTVSS], SEQ ID NO: 16 [QVQLQESGPGLVKPSETLSLTCTVSGGSVS SSYYWNWIRQPPGKGLEWIG YISFDGSNNYNPSLKNRVTISVDTSKNQFSLKLSSVTA ADTAVYYCAREKENYYGSSFYYFDYWGQG TLVTVSS], and SEQ ID NO: 17 [QVQLQESG-PGLVKPSETLSLTCAVSGYSIS SSYYWNWIRQPPGKGLEWIG YISFDGSNNYNPSLKNRVTISVDTSKNQFSLKLSSVTA ADTAVYYCAREKENYYGSSFYYFDYWGQG TLVTVSS](CDR sequences are underlined in SEQ ID NOs: 10-17, while framework regions lack underlining. The four framework regions in each sequence are numbered 1-4 (FW1, FW2, FW3, and FW4) starting from the N-terminal ends of the sequences). In certain embodiments, an anti-ILT5 antibody or an ILT5-binding antibody fragment comprises one or more human framework regions from a heavy chain variable region comprising an amino acid sequence selected from the group consisting of the amino acid sequence of SEQ ID NO: 10.

In certain embodiments, an anti-ILT5 antibody or an ILT5-binding antibody fragment comprises one or more human framework regions from a light chain variable region comprising an amino acid sequence selected from the group consisting of the amino acid sequence of SEQ ID NO: 18 [AIRMTQSPSSFSASTGDRVTITC RASENIYSNLAWYQQKPGKAPKLLIYAATNLADGVP SRFSGSGSGTDFTLTISCLQSEDFATYYFATYYC QHFWRIPWTFGQGTKVEIK], SEQ ID NO: 19 [DIQLTQSPSFLSASVGDRVTITC RASENIYSNLAWYQQKPGKAPKLLIY AATNLADGVPS RFSGSGSGTEFTLTISSLQPEDFA-TYYCQHFWRIPWTFGQGTKVEIK], SEQ ID NO: 20 [DIQMTQSPSSVSASVGDRVTITC RASENIYSNLAWYQQKPGKAPKLLIYAATNLADGVP SRFSGSGSGTDFTLTISSLQPEDFATYYC QHFWRIPWTFGQGTKVEIK], SEQ ID NO: 21 [DIQMTQSPSSVSASVGDRVTITC RASENIYSNLAWYQQKPGKAPKLLIYAATNLADGVP SRFSGSGSGTDFTLTISSLQPEDFATYYC QHFWRIPWTFGQGTKVEIK], SEQ ID NO: 22 [AIQLTQSPSSLSASVGDRVTITC RASENIYSNLAWYQQKPGKAPKLLIY AATNLADGVPS RFSGSGSGTDFTLTISSLQPEDFA-TYYCQHFWRIPWTFGQGTKVEIK], SEQ ID NO: 23 [AIQLTQSPSSLSASVGDRVTITC RASENIYSNLAWYQQKPGKAPKLLIY AATNLADGVPS RFSGSGSGTDFTLTISSLQPEDFA-TYYCQHFWRIPWTFGQGTKVEIK], and SEQ ID NO: 24 [DIQMTQSPSSLSASVGDRVTITC RASENIYSNLAWYQQKPEKAPKSLIYAATNLADGVP SRFSGSGSGTDFTLTISSLQPEDFATYYC QHFWRIPWTFGQGTKVEIK](CDR sequences are underlined in SEQ ID NOs: 18-24, while framework regions lack underlining. The four framework regions in each sequence are numbered 1-4 (FW1, FW2, FW3, and FW4) starting from the N-terminal ends of the sequences). In certain embodiments, an anti-ILT5 antibody or an ILT5-binding antibody fragment thereof comprises one or more human framework regions from a light chain variable region comprising an amino acid sequence selected from the group consisting of the amino acid sequence of SEQ ID NO: 18.

In certain embodiments, an anti-ILT5 antibody or an ILT5-binding antibody fragment comprises one or more human framework regions from a heavy chain variable region comprising an amino acid sequence selected from the group consisting of the amino acid sequence of SEQ ID NO: 10-17, and a light chain variable region comprising an amino acid sequence selected from the group consisting of the amino acid sequence of SEQ ID NOs: 18-24.

In certain embodiments, a CDR homology based method is used for humanization (see, e.g., Hwang, W. Y. K., et al., Methods 36:35, 2005). This method generally involves substitution of non-human CDRs into a human framework based on similarly structured non-human and human CDRs, rather than similarly structured non-human and human frameworks. The similarity of the non-human and human CDRs is generally determined by identifying human genes of the same chain type (light or heavy) that have the same combination of canonical CDR structures as the mouse binding molecules and thus retain three-dimensional conformation of CDR peptide backbones. Secondly, for each of the candidate variable region gene segments with matching canonical structures, residue to residue homology between the non-human and candidate human CDRs is evaluated. Finally, to generate a humanized binding molecule, CDR residues of the chosen human candidate CDR not already identical to the non-human CDR are converted to the non-human sequence. In certain embodiments, no mutations of the human framework are introduced into the humanized binding molecule.

In certain embodiments, the substitution of non-human CDRs into a human framework is based on the retention of the correct spatial orientation of the non-human framework by identifying human frameworks which will retain the same conformation as the non-human frameworks from which the CDRs were derived. In certain embodiments, this is achieved by obtaining the human variable regions from human antibodies whose framework sequences exhibit a high degree of sequence identity with the non-human framework regions from which the CDRs were derived. See Kettleborough et al., Protein Engineering 4:773, 1991; Kolbinger et al., Protein Engineering 6:971, 1993; and Carter et al., WO 92/22653, each of which is incorporated herein by reference in its entirety.

In certain embodiments, one or more human framework residues can be changed or substituted to residues at the corresponding positions in the original non-human (e.g. murine) antibody so as to preserve the binding affinity of the humanized antibody to the antigen. Such a change is sometimes called "backmutation". Certain amino acids from the human framework residues are selected for backmutation based on their possible influence on CDR conformation and/or binding to antigen. For example, residues immediately surrounding one or more CDRs can be backmutated to ensure proper spatial positioning of the CDRs. The placement of non-human (e.g. murine) CDR regions within human framework regions can result in conformational restraints, which, unless corrected by substitution of certain amino acid residues, lead to loss of binding affinity. Thus, in certain embodiments, backmutations can be made in residues that affect proper conformation of the anti-ILT5 antibody or ILT5-binding fragment to ensure adequate affinity to ILT5.

In certain embodiments, the selection of amino acid residues for backmutation can be determined, in part, by computer modeling, using art recognized techniques. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

The selection of amino acid residues for substitution can also be determined, in part, by examination of the characteristics of the amino acids at particular locations, or empirical observation of the effects of substitution or mutagenesis of particular amino acids. For example, when an amino acid differs between a non-human (e.g. murine) framework residue and a selected human framework residue, the human framework amino acid may be substituted by the equivalent framework amino acid from the non-human binding molecule when it is reasonably expected that the amino acid: (1) noncovalently binds antigen directly, (2) is adjacent to a CDR region, (3) otherwise interacts with a CDR region (e.g., is within about 3-6 angstroms of a CDR region as determined by computer modeling), or (4) participates in the VL-VH interface.

In certain embodiments, an anti-ILT5 antibody or an ILT5-binding antibody fragment comprises a human heavy chain constant region. For example, an anti-ILT5 antibody or an ILT5-binding antibody fragment may comprise an IgG (γ) heavy chain constant region such as a IgG1 (γ1) heavy chain constant region, an IgG2 (γ2) heavy chain constant region, an IgG3 (γ3) heavy chain constant region, or an IgG4 (γ4) heavy chain constant region. Moreover, they can comprise an IgA (α) heavy chain constant region, an IgE (ε) heavy chain constant region, an IgM (μ) heavy chain constant region, or an IgD (δ) heavy chain constant region. In certain embodiments, an anti-ILT5 antibody or an ILT5-binding antibody fragment comprises a heavy chain constant region comprising the amino acid sequence of SEQ ID NO: 25 [ASTKGPSVF-PLAPSSKSTSGGTAALGCLVKDYFPEP-VTVSWNSGALTSGVHTFPAVLQS SGLYSLSSV-VTVPSSSLGTQTYICNVNHKPSNTKVDKKVEPKSCD KTHTCPPCPAPELLG GPSVFLFPPKPKDTLMISRTPE-VTCVVVDVSHEDPEVKFNWYVDGVEVH-NAKTKPREEQ Y NSTYRVVSVLTVLHQDWLNGKEYKCKVSNKALPAPI EKTISKAKGQPREPQVYTLPPS RDELTKNQVSLT-CLVKGFYPSDIAVEWESNGQPENNYKT-TPPVLDSDGSFFLYSKLTVD KSRWQQGNVFSCSVM-HEALHNHYTQKSLSLSPGK]. In certain embodiments, an anti-ILT5 antibody or an ILT5-binding antibody fragment comprises a heavy chain constant region comprising the amino acid sequence of SEQ ID NO: 26 [ASTKGPSVF-PLAPSSKSTSGGTAALGCLVKDYFPEP-VTVSWNSGALTSGVHTFPAVLQS SGLYSLSSV-VTVPSSSLGTQTYICNVNHKPSNTKVDKKVEPKSCD KTHTCPPCPAPELLG GPSVFLFPPKPKDTLMISRTPE-VTCVVVDVSHEDPEVKFNWYVDGVEVH-NAKTKPREEQ Y ASTYRVVSVLTVLHQDWLNGKEYKCKVSNKALPAP IEKTISKAKGQPREPQVYTLPPS RDELTKNQVSLT-CLVKGFYPSDIAVEWESNGQPENNYKT-TPPVLDSDGSFFLYSKLTVD KSRWQQGNVFSCSVM-HEALHNHYTQKSLSLSPGK]. SEQ ID NO: 26 differs from SEQ ID NO: 25 in that an asparagine has been altered to an alanine (the relevant amino acid is underlined in each sequence), which alteration results in elimination of N-linked in vivo glycosylation of anti-ILT5 antibodies and ILT5-binding fragments thereof comprising SEQ ID NO: 26. Absence of N-linked glycosylation at the relevant residue results in drastically decreased binding of the Fc region of the relevant anti-ILT5 antibody or ILT5-binding fragment to a Fc receptor.

Any of a variety of other modifications may be made that result in reduced binding of an anti-ILT5 antibody or an ILT5-binding fragment to a Fc receptor. For example, a humanized OTK3-derived antibody in which two amino acid residues at positions 234 and 235 of the Fc domain have been modified to alanine residues (referred to as hOKT3-gamma-1 (ala-ala)) is disclosed in United States Patent Publication numbers 2007/0077246 and 2008/0095766, the disclosures of which are incorporated herein by reference in their entirety. The hOKT3-gamma-1 (ala-ala) antibody is described as exhibiting reduced binding to Fc (gamma) receptors, even though its Fc domain comprises residues that are N-linked glycosylated. In certain embodiments, an ant-ILT5 antibody or an ILT5-binding fragment thereof that exhibits reduced binding to at least one Fc (gamma) receptor is modified in that it lacks some or all of an Fc domain. For example, Fab fragments and F(ab')₂ fragments lack some or all of an Fc domain. In certain embodiments, an antibody or antigen-binding fragment thereof is modified in some other way such that it exhibits reduced binding to at least one Fc (gamma) receptor. For example, the anti-ILT5 antibody or ILT5-binding fragment may be modified by covalent linkage of a chemical moiety that prevents the anti-ILT5 antibody or ILT5-binding fragmen from binding, or decreases its ability to bind, to least one Fc (gamma) receptor. As another example, the anti-ILT5 antibody or ILT5-binding fragment may be modified by non-covalent linkage of a chemical moiety that prevents the anti-ILT5 antibody or ILT5-binding fragment from binding, or decreases its ability to bind, to least one Fc (gamma) receptor. Any of a variety of moieties may be covalently or non-covalently linked to the anti-ILT5 antibody or ILT5-binding fragment thereof to prevent or decrease binding to at least one Fc (gamma) receptor. Those skilled in the art will be aware of suitable moieties that can be linked to an antibody or fragment, and will be able to employ such moieties in accordance with the teachings herein.

In certain embodiments, any of a variety of modifications may be made to an anti-ILT5 antibody or an ILT5-binding antibody fragment, which modification results in alteration of the a physical or in vivo property of the anti-ILT5 antibody or ILT5-binding fragment. For example, any of a variety of modifications may be made that affect the stability of the anti-ILT5 antibody or ILT5-binding fragment (e.g., in vivo). Additionally and/or alternatively, any of a variety of modifications may be made that affect the halflife of an anti-ILT5 antibody or ILT5-binding fragment thereof in vivo. As is known in the art, FcRn protects IgG-type antibodies from degradation, resulting in longer half-life of this class of antibody in the serum (see Roopenian and Akilesh, Nature Reviews Immunology 7, 715-725, 2007, incorporated herein by reference in its entirety). Thus, in certain embodiments, an IgG-type antiI-ILT5 antibody or fragment thereof is modified by altering amino acid residues in its Fc region such that it bind differently to FcRn. Alterations that result in improved binding to FcRn will result in the anti-ILT5 antibody or ILT5-binding fragment having a longer halflife in vivo. Alterations that result in decreased binding to FcRn will result in the anti-ILT5 antibody or ILT5-binding fragment having a shorter halflife in vivo. Those skilled in the art will be aware of suitable alterations that can be made, such as pegylation and/or amino acid substitutions, and will be able to make such corresponding alterations in anti-ILT5 antibodies and ILT5-binding fragments thereof disclosed herein without undue experimentation.

In certain embodiments, an anti-ILT5 antibody or an ILT5-binding antibody fragment comprises a human light chain constant region. For example, an anti-ILT5 antibody or an ILT5-binding antibody fragment may comprise a human kappa or human lambda light chain constant region. In certain embodiments, an anti-ILT5 antibody or an ILT5-binding antibody fragment comprises a light chain constant region comprising the amino acid sequence of SEQ ID NO: 27 [RTVAAPSVFIFPSDEQLKSGTASV-VCLLNNFYPREAKVQWKVDNALQSGNSQESVTEQ DSKDSTYSLSSTLTLSKADYEKHKVY-ACEVTHQGLSSPVTKSFNRGEC].

In certain embodiments, an anti-ILT5 antibody or an ILT5-binding antibody fragment comprises a light chain comprising or consisting of the amino acid sequence of SEQ ID NO: 28 [DIQMTQSPASLSVSVGETVTITCRAS-ENIYSNLAWYQQKQGKSPQVLVYAATNLADGV PSRFSGSGSGTQFSLKINSLQSEDFGNY-FCQHFWRIPWTFGAGTKLEIKRTVAAPSVFIFPP SDEQLKSGTASVVCLLNN-FYPREAKVQWKVDNALQSGNSQESVTE-QDSKDSTYSLSST LTLSKADYEKHKVY-ACEVTHQGLSSPVTKSFNRGEC].

In certain embodiments, an anti-ILT5 antibody or an ILT5-binding antibody fragment comprises a heavy chain comprising or consisting of the amino acid sequence of SEQ ID NO: 29 [DVQLQESGPGLVKPSQSLFLTCSVTGY-SISSSYYWNWIRQFPGNKLEWMGYISFDGSNN YNPSLKNRISITRDTSKNQFFLKLNSVT-TEDTATYYCAREKENYYGS SFYYFDYWGAGT LVTVSSASTKGPSVFPLAPSSKSTSGG-TAALGCLVKDYFPEPVTVSWNSGALTSGVHTFP AVLQSSGLYSLSSVVTVPSSSLGTQTY-ICNVNHKPSNTKVDKKVEPKSCDKTHTCPPCPA PELLGGPSVFLFPPKPKDTLMISRTPE-VTCVVVDVSHEDPEVKFNWYVDGVEVHNAKTK PREEQY NSTYRVVSVLTVLHQDWLNGKEYKCKVSNKALPAP IEKTISKAKGQPREPQV YTLPPSRDELTKNQVSLT-CLVKGFYPSDIAVEWESNGQPENNYKT-TPPVLDSDGSFFLYS KLTVDKSRWQQGNVFSCSVM-HEALHNHYTQKSLSLSPGK] or SEQ ID NO: 30: [EVQLQESGPGLVKPSQSLFLTCSVTGY-SISSSYYWNWIRQFPGNKLEWMGYISFDGSNN YNPSLKNRISITRDTSKNQFFLKLNSVT-TEDTATYYCAREKENYYGSSFYYFDYWGAGT LVTVSSASTKGPSVFPLAPSSKSTSGG-TAALGCLVKDYFPEPVTVSWNSGALTSGVHTFP AVLQSSGLYSLSSVVTVPSSSLGTQTY-ICNVNHKPSNTKVDKKVEPKSCDKTHTCPPCPA PELLGGPSVFLFPPKPKDTLMISRTPE-VTCVVVDVSHEDPEVKFNWYVDGVEVHNAKTK PREEQYNSTYRVVSVLTVLHQDWL-NGKEYKCKVSNKALPAPIEKTISKAKGQPREPQV YTLPPSRDELTKNQVSLTCLVKGFYPS-DIAVEWESNGQPENNYKTTPPVLDSDGSFFLYS KLTVDKSRWQQGNVFSCSVMHEALH-NHYTQKSLSLSPGK]. In certain embodiments, an anti-ILT5 antibody or an ILT5-binding antibody fragment comprises a heavy chain comprising or consisting of the amino acid sequence of SEQ ID NO: 31 [DVQLQESG-PGLVKPSQSLFLTCSVTGYSISSSYYWN-WIRQFPGNKLEWMGYISFDGSNN YNPSLKN-RISITRDTSKNQFFLKLNSVTTEDTATYYCAREKENY YGSSFYYFDYWGAGT LVTVSSASTKGPSVF-PLAPSSKSTSGGTAALGCLVKDYFPEP-VTVSWNSGALTSGVHTFP AVLQSSGLYSLSSV-VTVPSSSLGTQTYICNVNHKPSNTKVDKKVEPKSCD KTHTCPPCPA PELLGGPSVFLFPPKPKDTLMISRTPE-VTCVVVDVSHEDPEVKFNWYVDGVEVHNAKTK PREEQY ASTYRVVSVLTVLHQDWLNGKEYKCKVSNKALPAP IEKTISKAKGQPREPQV YTLPPSRDELTKNQVSLT-CLVKGFYPSDIAVEWESNGQPENNYKT-TPPVLDSDGSFFLYS KLTVDKSRWQQGNVFSCSVM-HEALHNHYTQKSLSLSPGK] or SEQ ID NO: 32 [EVQLQESGPGLVKPSQSLFLTCSVTGY-SISSSYYWNWIRQFPGNKLEWMGYISFDGSNN YNPSLKNRISITRDTSKNQFFLKLNSVT-TEDTATYYCAREKENYYGSSFYYFDYWGAGT LVTVSSASTKGPSVFPLAPSSKSTSGG-TAALGCLVKDYFPEPVTVSWNSGALTSGVHTFP AVLQSSGLYSLSSVVTVPSSSLGTQTY-ICNVNHKPSNTKVDKKVEPKSCDKTHTCPPCPA PELLGGPSVFLFPPKPKDTLMISRTPE-VTCVVVDVSHEDPEVKFNWYVDGVEVHNAKTK PREEQY ASTYRVVSVLTVLHQDWLNGKEYKCKVSNKALPAP IEKTISKAKGQPREPQV YTLPPSRDELTKNQVSLT-CLVKGFYPSDIAVEWESNGQPENNYKT-TPPVLDSDGSFFLYS KLTVDKSRWQQGNVFSCSVM-HEALHNHYTQKSLSLSPGK]. SEQ ID NOs: 29 and 30 differs from SEQ ID NOs: 31 and 32 in that an asparagine has been altered to an alanine (the relevant amino acid is underlined in each sequence), which alteration results in decreased in vivo glycosylation of anti-ILT5 antibodies and ILT5-binding fragments thereof comprising SEQ ID NOs: 31 and 32.

In certain embodiments, an anti-ILT5 antibody or an ILT5-binding antibody fragment comprises a light chain comprising or consisting of the amino acid sequence of SEQ ID NO: 28, and a heavy chain comprising or consisting of the amino acid sequence of SEQ ID NO: 29, SEQ ID NO: 30, SEQ ID NO: 31, or SEQ ID NO: 32.

In certain embodiments, an anti-ILT5 antibody or an ILT5-binding antibody fragment comprises an amino acid sequence that is at least 75% identical to one or more of SEQ ID NOs: 1-32, e.g., at least 80% identical, at least 85% identical, at least 90% identical, at least 95% identical, at least 96% identical, at least 97% identical, at least 98% identical, or at least 99% identical to one or more of SEQ ID NOs: 1-32. In certain embodiments, an anti-ILT5 antibody or ILT5-binding fragment thereof comprises an amino acid sequence comprising at least 5 contiguous amino acid residues of one or more of SEQ ID NOs: 1-32, e.g., at least 6, at least 7, at least 8, at least 9, at least 10, at least 11, at least 12, at least 13, at least 14, at least 15, at least 20, at least 25, at least 30, at least 40, at least 50, or more contiguous amino acid residues.

In certain embodiments, an anti-ILT5 antibody or an ILT5-binding antibody fragment comprises a polypeptide having one or more amino acid substitutions, deletions or insertions as compared to a polypeptide having an amino acid sequence of one or more of SEQ ID NOs: 1-32. For example, an anti-ILT5 antibody or an ILT5-binding antibody fragment may have 1, 2, 3, 4, 5, 6, 7, 8, 9, 10, or more amino acid substitutions, deletions or insertions. Substitutions, deletions or insertions may be introduced by standard techniques, such as site-directed mutagenesis or PCR-mediated mutagenesis of a nucleic acid molecule encoding a polypeptide of an anti-ILT5 antibody or an ILT5-binding antibody fragment. In certain embodiments, conservative amino acid substitutions are made at one or more positions. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan; histidine). Thus, an amino acid residue in a polypeptide of an anti-ILT5 antibody or an ILT5-binding antibody fragment may be replaced with another amino acid residue from the same side chain family. In certain embodiments, a string of amino acids can be replaced with a structurally similar string that differs in order and/or composition of side chain family members. Those skilled in the art will be able to evaluate whether an anti-ILT5 antibody or an ILT5-binding antibody fragment comprising a polypeptide having one or more amino acid substitutions, deletions or insertions as compared to a polypeptide having an amino acid sequence of one or more of SEQ ID NOs: 1-32 binds ILT5 by utilizing routine, art-recognized methods including, but not limited to, ELISAs, Western blots, phage display, etc.

Anti-ILT5 antibodies and ILT5-binding fragments thereof can be produced by any of a variety of methods known to those skilled in the art. In certain embodiments, anti-ILT5 antibodies and ILT5-binding antibody fragments can be produced recombinantly. For example, nucleic acid sequences encoding one or more of SEQ ID NOs: 1-32, or portions thereof, may be introduced into a bacterial cell (e.g., *E. coli, B. subtilis*) or a eukaryotic cell (e.g., a yeast such as *S. cerevisiae*, or a mammalian cell such as a CHO cell line, various Cos cell lines, a HeLa cell, various myeloma cell lines, or a transformed B-cell or hybridoma), or into an in vitro translation system, and the translated polypeptide may be isolated. One of ordinary skill in the art will recognize that antibody light chain proteins and heavy chain proteins are produced in the cell with a leader sequence that is removed upon production of a mature anti-ILT5 antibody or ILT5-binding fragment thereof.

Anti-ILT5 antibodies and ILT5-binding antibody fragments can be prepared by recombinant expression of immunoglobulin light and heavy chain genes in a host cell. For example, a host cell is transfected with one or more recombinant expression vectors carrying DNA fragments encoding the light and heavy chains of the anti-ILT5 antibody or ILT5-binding fragment such that the light and heavy chains are expressed in the host cell and, preferably, secreted into the medium in which the host cells are cultured, from which medium the anti-ILT5 antibody or ILT5-binding fragment can be recovered. Standard recombinant DNA methodologies are used to obtain antibody heavy and light chain genes, incorporate these genes into recombinant expression vectors, and introduce the vectors into host cells (e.g., methodologies such as those described in Sambrook, Fritsch and Maniatis (eds), Molecular Cloning; A Laboratory Manual, Second Edition, Cold Spring Harbor, N.Y., 1989; Ausubel, F. M. et al. (eds.) Current Protocols in Molecular Biology, Greene Publishing Associates, 1989; and in U.S. Pat. No. 4,816,397, each of which is incorporated herein by reference in its entirety.

As is understood in the art, an expression vector comprises sequences that mediate replication and often comprises one or more selectable markers. An expression vector is transfected into a host cell by standard techniques. Non-limiting examples include electroporation, calcium-phosphate precipitation, DEAE-dextran transfection and the like.

To express an anti-ILT5 antibody or an ILT5-binding antibody fragment, DNA (e.g., cDNA) molecules encoding partial or full-length light and heavy chains (e.g., human or humanized heavy and light chains) may be inserted into expression vectors such that the genes are operatively linked to transcriptional and translational control sequences. In this context, the term "operatively linked" means that a nucleic acid sequence encoding the anti-ILT5 antibody or ILT5-binding fragment is inserted into a vector such that transcriptional and translational control sequences within the vector serve their intended function of regulating the transcription and translation of the nucleic acid sequence. In certain embodiments, the expression vector and expression control sequences are chosen to be compatible with the expression host cell used. Nucleic acid sequences encoding the light and heavy chains may be inserted into separate vectors or both genes may be inserted into the same expression vector. The nucleic acid sequences may be inserted into the expression vector by standard methods (e.g., ligation of complementary restriction sites on the binding molecule gene fragment and vector, or blunt end ligation if no restriction sites are present). Prior to insertion of light and/or heavy chain-encoding sequences, the expression vector may already comprise a nucleic acid sequence encoding a constant region. For example, one approach to converting VH and VL sequences to full-length antibody-encoding sequences is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide fused in frame to the heavy and/or light chain that facilitates secretion of the binding molecule chain from a host cell. The signal peptide can be an immunoglobulin signal peptide or a heterologous signal peptide (i.e., a signal peptide from a non-immunoglobulin protein).

Those skilled in the art will be able to determine whether an antibody or fragment comprising a given polypeptide sequence binds to ILT5 without undue experimentation using standard methodologies such as, without limitation, Western blots, ELISA assays, and the like.

Certain embodiments of methods and compositions provided herein are further illustrated by the following examples. The examples are provided for illustrative purposes only. They are not to be construed as limiting the scope or content of the invention in any way.

EXAMPLES

Example 1

Preparation of Anti-ILT5 Antibodies

A human ILT5-mouse Ig fusion construct was generated using standard molecular biology techniques. Soluble ILT5-Ig fusion protein was purified from the cell culture supernatant of transiently transfected 293 cells by Protein A/G-Sepharose chromatography. Expression plasmid DNA (100 µg) encoding the ILT5-Ig fusion protein was coated onto gold beads (1 µM) according to instructions from the manufacturer (Bio-Rad, Hercules, Calif.). Mice were immunized with hILT5-Ig expression plasmid-coated gold beads every other day for 10 days using a Helios® Gene Gun. Sera from immunized mice were tested for reactivity by ELISA against purified hILT5-Ig protein. Mice with demonstrated serum immunoreactivity were boosted with recombinant hILT5-Ig fusion protein (20 µg/200 µl) three days prior to fusion. Hybridoma supernatants were screened by ELISA for immunoreactivity against purified hILT5-Ig and an irrelevant Ig fusion protein. Hybridomas producing antibody reactive with hILT5-Ig but not the irrelevant fusion protein were cloned by limiting dilution and soft agar. The 8G6 mAb (IgG1,κ, hereafter referred to as "TRX585") was purified from hybridoma culture supernatant by Protein G Sepharose column chromatography and dialyzed against Dulbecco's Phosphate Buffered Saline overnight at 2–8° C. The purified TRX585 mAb was stored at –80° C. until use.

Example 2

Expression of ILT5 Receptor

Surface Expression of ILT5:
Peripheral blood mononuclear cells (PBMCs) from healthy human blood donors were stained with a murine monoclonal antibody (TRX585) comprising a heavy chain variable region comprising the amino acid sequence of SEQ ID NO: 2 or SEQ ID NO: 3, and a light chain variable region comprising the amino acid sequence of SEQ ID NO: 1. Sequencing analysis of the heavy chain variable region was inconclusive as to whether the first amino acid residue was D or E. As the two amino acids are very similar and the first residue is not in a CDR, it is highly likely that VH with D or E at the first position would have very similar if not the same ILT5-binding properties. PBMCs were also stained with antibodies specific for defined hematopoietic cell lineages and analyzed for ILT5 expression by flow cytometry.

ILT5 Expression by CD4+ and CD8+ T Cells:
The surface expression of ILT5 was observed on about 1% of CD56$^-$CD4$^+$CD3$^+$ T cells but not on CD56$^-$CD8$^+$CD3$^+$ T cells (FIG. 1A). Experimental details can be found in FIG. 1A and the description thereof.

Figure 1:
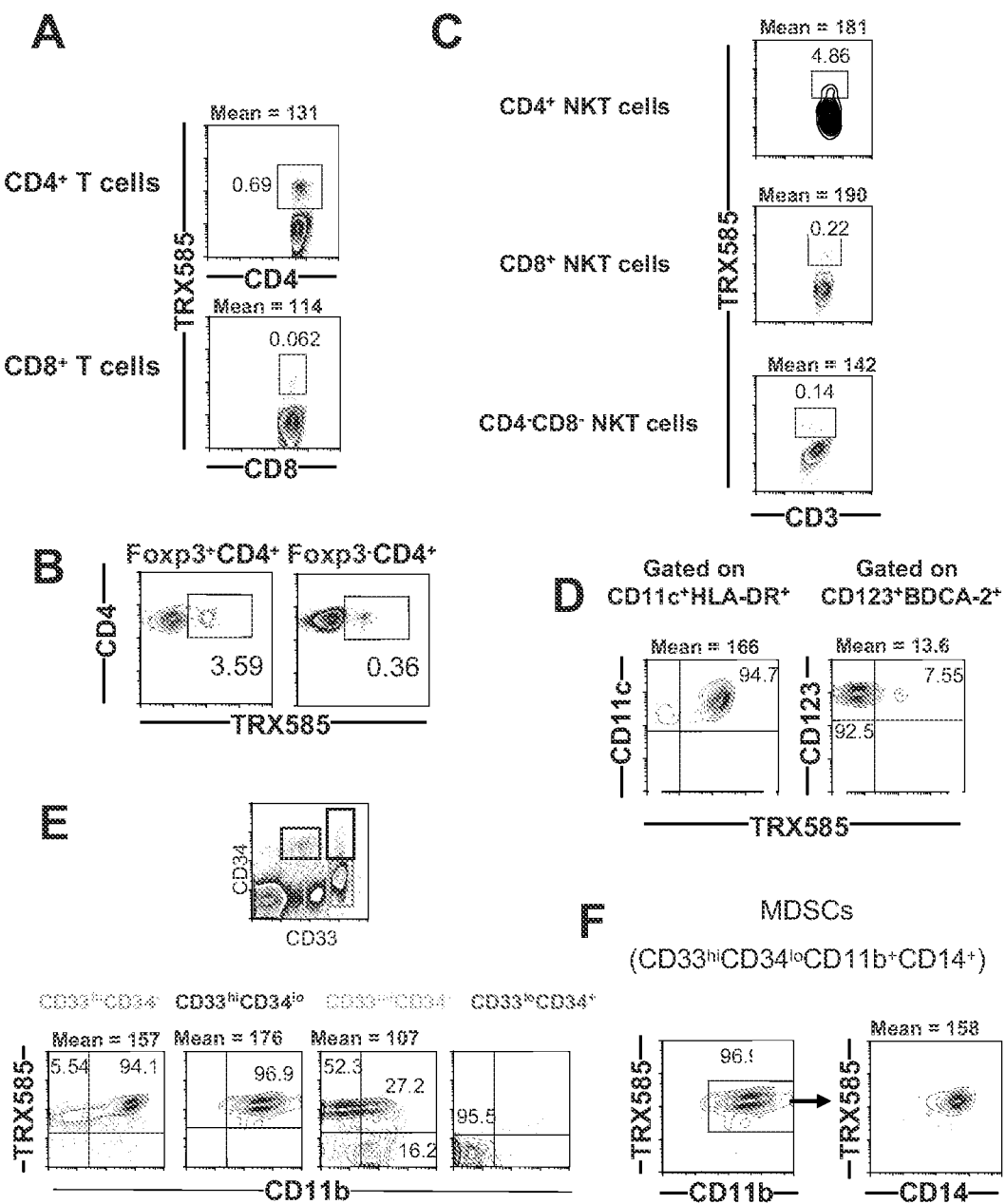
FIG. 1 shows the expression of ILT5 by various hematopoietic subsets in the form of two-dimensional flow cytometry (FCM) representations called quantile contour plots (or probability plots). The latter plots show the levels of two fluorescent parameters (i.e., fluorescent antibodies) on various cell subpopulations, quantitate the proportions of cells displaying these parameters, and indicate the frequency of cells present at each point in the plot. Here, peripheral blood mononuclear cells (PBMCs) from a healthy human donor were stained with the TRX585 antibody as well as antibodies specific for the indicated cell subset.

ILT5 Expression by Tregs:
ILT5 expression by regulatory T cells (Tregs) was examined by staining with the TRX585 antibody. Naïve Foxp3$^+$CD4$^+$CD3$^+$ cells were found to display about 10 fold more ILT5 than their Foxp3– counterpart (see FIG. 1B). Furthermore, 5% of CD4$^+$ natural killer T (NKT) cells, another immunomodulatory T cell subset that is restricted by the non-classical MHC class I molecule, CD1d, also exhibited surface expression of ILT5 (FIG. 1C). Experimental procedures can be found in FIG. 1 (panels B and C) and the description thereof.

ILT5 Expression by APCs:
ILT5 expression was measured on APCs by staining with the TRX585 antibody. Steady state myeloid dendritic cells (DCs) (CD11c$^+$HLA$^-$DR$^+$ cells) showed ILT5 expression whereas plasmacytoid DCs did not express surface ILT5 (see FIG. 1D). In contrast, the majority of monocytic subsets were found to express ILT5, albeit at varying levels (FIG. 1E). Further experimental details can be found in FIG. 1 (panels D, E) and the description thereof.

ILT5 Expression by MDSCs:
Cancer patients often show an increase in myeloid-derived suppressor cells (MDSCs), which can suppress T cell responses in peripheral blood, as well as within the tumors. Increasing evidence suggests that MDSCs contribute to the induction of tolerance in cancer and some other pathologies. ILT5 expression on steady state peripheral blood MDSCs, defined as CD33$^{hi}$CD34$^{lo}$CD11b$^+$CD14$^+$ cells, was detected by staining with the TRX585 antibody. These cells were found to express high levels of surface ILT5 (FIG. 1F). Experimental procedures are detailed in FIG. 1F and the description thereof.

Example 3

Characteristics and Biological Activity of the TRX585 Anti-ILT5 Antibody

Figure 2:
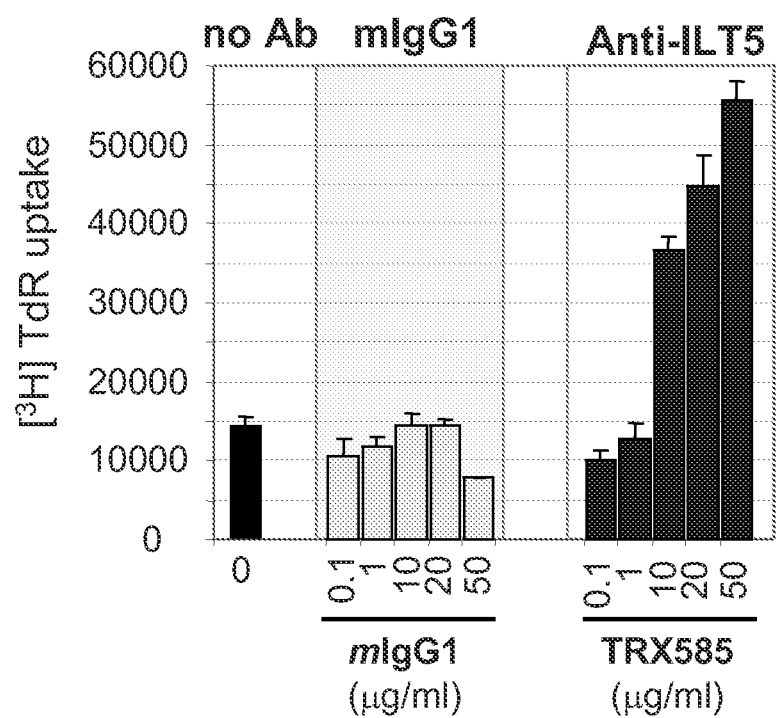
FIG. 2 is a series of bar graphs showing TRX585 antibody-mediated hyperresponsiveness of allogeneic responder lymphocytes in primary MLRs (mixed lymphocyte reactions). $2\times10^5$ PBMCs (responder population)/well were cultured with $2\times10^5$ mitomycin-treated PBMCs (stimulator population) from an unrelated blood donor in the presence or absence of the indicated amounts of mIgG1 or TRX585 antibodies. Proliferative activity in the MLR was measured at day 3.5 by the incorporation of 1 µCi [$^3$H]TdR (tritiated thymidine) per well to the DNA of replicating cells during the last 12-18 hours of the culture. The X axes indicate the concentration of antibody. The Y axes indicate [$^3$H]TdR uptake. Data shown are representative of several experiments utilizing different responder/stimulator pairs and are reported as the mean cpm±standard error of triplicate wells.

Immunoregulatory Properties of TRX585 Antibody:
Stimulation of peripheral blood mononuclear cells (PBMC) with mitomycin C-treated allogeneic PBMCs is an established in vitro model for T cell responsiveness. Because ILT molecules are thought to be immunomodulatory, it was tested whether crosslinking of ILT5 by means of the mouse anti-human ILT5 TRX585 antibody would modulate a mixed lymphocyte response (MLR). To this end, the proliferation of allogeneic PBMCs in primary MLRs performed in the presence or absence of increasing doses of soluble TRX585 antibody or a mouse IgG1 isotype control antibody (mIgG1) was compared. There was no change in the intensity of the MLR responses for varying concentrations of control mIgG1 (see FIG. 2). In contrast, TRX585 antibody-mediated a dose-dependent enhancement of cell proliferation (FIG. 2). Further detail can be found in FIG. 2 and the description thereof.

Figure 3:
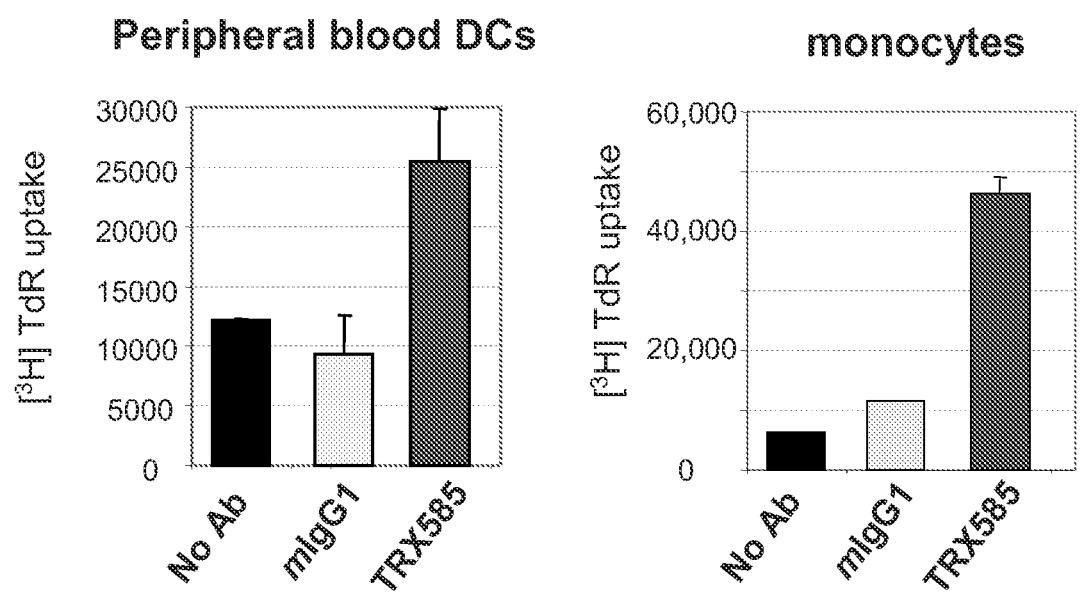
FIG. 3 is a pair of bar graphs showing that pretreatment of peripheral blood monocytes or DCs with soluble TRX585 antibody prior to their use in MLR assays resulted in antibody-mediated enhancement of cell proliferation. DCs or monocytes that were purified from PBMCs were incubated in the presence or absence of 50 µg/ml mIgG1 isotype control or TRX585 antibody. Twenty four hours later, precultured DCs and monocytes were washed to remove unbound antibodies, seeded at 1000 and 120,000 cells per well, respectively, and cocultured with $1\times10^5$ T cells freshly isolated from PBMCs. [$^3$H]thymidine incorporation was measured as described above. Data shown are representative of several experiments utilizing different responder/stimulator pairs and are reported as the mean cpm of triplicate wells. The X axes indicate which antibody was used. The Y axes indicate [$^3$H]TdR uptake.

These observations were established under conditions in which TRX585 antibody was left in the culture for the entire duration of the assay. To examine whether the TRX585 antibody-mediated increase of T cell proliferation was dependent on the level of antibodies present in the culture, ILT-expressing antigen-presenting cells (APCs) were pretreated with soluble (50 µg/ml) TRX585 antibody for 24-48 hours, washed, and utilized as stimulators in allogeneic MLRs. Pretreatment of monocytes or peripheral blood DCs with soluble TRX585 antibody prior to its use in MLR assays recapitulated the antibody-mediated enhancement of cell proliferation that was observed in initial experiments (FIG. 3). Further detail can be found in FIG. 3 and the description thereof.

Myeloid/monocytic cells express both activation and inhibitory Fc receptors, the engagement of which by antibodies can either enhance or downregulate immunity and, thus, either increase or decrease the potency of antibodies with immunoregulatory properties. To test whether the biological effect of TRX585 antibody could be enhanced by Fc crosslinking, primary MLR assays were conducted as described above in the presence or absence of 10 µg/ml F(ab')$_2$ goat anti-mouse IgG antibody. At subsaturating concentrations (<10 µg/ml), monovalent (i.e., in the absence of F(ab')$_2$ goat anti-mouse IgG antibody) but not divalent TRX585 antibody (i.e., in the presence of F(ab')$_2$ goat anti-mouse IgG antibody) induced cell proliferation (see FIG. 4). However, addition of TRX585 antibody at concentrations higher than that of F(ab')$_2$ fragments restored hyperresponsiveness, albeit at levels much lower than that observed with identical concentrations of monovalent TRX585 antibody (i.e., in the absence of F(ab')$_2$ goat anti-mouse IgG antibody) (see FIG. 4). Experimental procedures are detailed in FIG. 4 and the description thereof.

Figure 5:
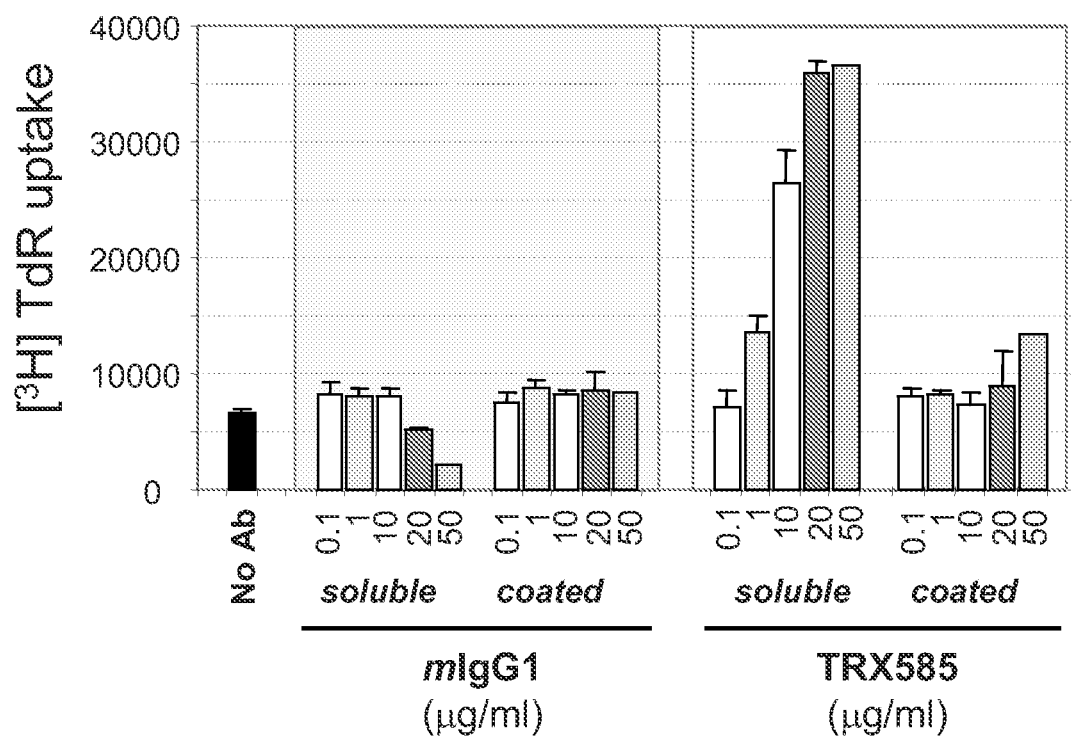
FIG. 5 is a pair of bar graphs showing that immobilization of TRX585 antibody on plastic abolishes its immunostimulatory potential. $2\times10^5$ PBMCs/well were cultured with $2\times10^5$ mitomycin-treated allogeneic PBMCs with either soluble or tissue culture plate-bound TRX585, which was coated onto the tissue culture plate well bottoms at the indicated concentrations. [$^3$H]TdR-incorporation (1 µCi/well) in the last 12-18 hours of the culture was measured at day 3.5. The X axes indicate the concentration of antibody. The Y axes indicate [$^3$H]TdR uptake. Shown is the mean cpm of triplicate wells.

To determine whether the above observations could be extended to antibodies of higher valency, allogeneic PBMCs were seeded either with soluble or solid phase TRX585 antibody. Antibody-induced proliferation was observed with soluble but not TRX585 antibody immobilized on plastic (see FIG. 5 and the description thereof). In accordance with these observations, pretreatment of APCs with solid phase antibody did not lead to an enhancement of T cell responses (data not shown). Addition of soluble TRX585 antibody to APCs resulted in occupancy and partial internalization of surface ILT5, whereas addition of solid phase TRX585 antibody to APCs induced complete internalization of ILT5 (data not shown).

Overall, these observations indicate that monovalent and polyvalent TRX585 antibodies have a differential effect on APCs and APC-mediated regulation of T cell responses. Furthermore, the above findings suggest that in vivo hyper-crosslinking of ILT5 antigens on APCs by TRX585 antibody may decrease the effectiveness of the latter reagents. Crosslinking can be reduced by modification of the antibody to reduce or eliminate binding via the Fc receptors.

Closer examination of proliferating cells in MLR assays revealed that TRX585 antibodies induced the proliferation of the vast majority of $CD4^+$ and $CD8^+$ T cells in allogeneic as well as autologous settings. This was determined by examining cell content CFSE dye by flow cytometry since this fluorescent dye gets diluted as cells divide (see FIG. 6A and the description thereof). In another experiment, purified T cells were cultured with the TRX585 or mIgG1, with or without allogeneic stimulator cells. The lack of proliferation of the purified T cells, which was observed, ruled out the possibility that TRX585 antibody was directly mitogenic to T cells, and demonstrated that TRX585 antibody-induced T cell proliferation required the presence of non-T cells (see FIG. 6B and the description thereof).

Because not all T cells can undergo simultaneous proliferation as a consequence of self and/or non-self recognition, the previous observations suggested that TRX585 antibody-induced T cell proliferation was achieved in a TCR-independent manner (e.g., proliferation does not require recognition of a MHC molecule by a TCR). Indeed, blocking TCR:MHC/peptide complex interactions by means of pan anti-MHC antibodies did not abrogate TRX585 antibody-induced T cell proliferation (see FIG. 7). Further detail can be found in FIG. 7 and the description thereof.

Generation of T Cells with Altered Phenotype:

Upon culturing PBMCs with the TRX585 antibody as described above, proliferating $CD4^+$ and $CD8^+$ T cells acquired a unique phenotype. In addition to upregulating CD25, T cells also upregulated expression of NKG2D, a major innate activating immune receptor that plays an important role in anti-tumor and anti-viral immunity (see FIGS. 8A and 8B and the description thereof).

Ligands for NKG2D are rarely detected on healthy tissues and cells, but are often expressed by tumor cells as well as virus-infected cells. In humans and mice, local as well as systemic (through shedding of NKG2D ligands) down-regulation of NKG2D as a consequence of persistent expression of NKG2D ligands is one mechanism by which tumors and viruses escape immune surveillance. We thus examined NKG2D expression on T cells that were subjected to both TRX585 antibodies and signals mimicking NKG2D persistent engagement by NKG2D ligands. Remarkably, TRX585 antibody-exposed T cells not only upregulated NKG2D at levels higher than that observed on steady state natural killer (NK) cells (see FIG. 8B and the description thereof for further detail), but presented with a sustained expression of NKG2D under conditions that normally trigger its internalization and subsequent degradation (e.g., via NKG2D engagement by either soluble MICA antigen (a NKG2D ligand) or anti-NKG2D mAbs, clones 1D11 and 5C6) (see FIG. 9 and the description thereof for further detail).

The tight control of NKG2D-mediated effector functions by microenvironmental factors, such as NKG2D ligands and cytokines, should provide an additional safeguard mechanism to prevent the development of unwanted immune responses.

Production of Cytokines and Chemokines:

Supernatants from MLR assay cultures conducted in the presence of soluble TRX585 antibody contained increased amounts of TNF-alpha and IL5 as compared to control cultures (data not shown). Addition of TRX585 antibody did not result in overproduction of other major cytokines such as IL2, IFN-gamma, IL17, IL6, and IL12. In contrast, TRX585 antibody-containing cultures contained increased amounts of Rantes, IP-10 and MIP-1 chemokines, which play an active role in recruiting leukocytes into inflammatory sites and can elicit powerful antitumor effect in vivo (data not shown). In cultures containing TRX585 antibody, T cells also overproduced soluble Fas ligand, a factor that participates in essential effector functions of the immune system and is, for example, a potent mediator of cytotoxicity. Further detail can be found in FIG. 10 and the description thereof. The above observation prompted investigation into whether TRX585 antibody-activated T cells were endowed with cytotoxic activity. To this end, PBMCs were cultured in the presence of TRX585 or mIgG1 antibodies for 3.5 days. Proliferating T cells (effector cells) were subsequently cell-sorted and mixed with a variety of tumor cells (target cells) at different effector:target (E:T) ratios for 12-18 hours. Examination of tumor cell viability after the incubation showed that T cells from TRX585 antibody-containing but not mIgG1-containing precultures exerted a potent anti-tumor cytotoxic effect (see FIGS. 11A and B). Although the presence of human cytotoxic T cells has been reported in a number of viral infections and rheumatoid arthritis, acquisition of lytic activity by $CD4^+$ T cells is a rare event. Yet, preactivation of PBMCs with TRX585 antibodies was found to confer a cytotoxic activity to both $CD4^+$ and $CD8^+$ T cell subsets (see FIG. 11C and the description thereof for experimental procedures). Of note, the cytotoxic activity of $CD4^+$ and $CD8^+$ T cells appeared to be specific to tumor cells but not healthy cells since the same T cells did not kill autologous or allogeneic PBMCs using the same killing assay (not shown).

TRX585 antibody-induced cytotoxic $CD4^+$ and $CD8^+$ T cells did not express perforin or granzyme A (data not shown), ruling out these molecules as possible mediators of the observed cytotoxicity. In contrast, blocking MHC class I molecules or Fas ligand by means of a pan anti-MHC class I antibody or a neutralizing anti-Fas ligand antibody, respectively, markedly diminished the anti-tumor cytotoxic effect of T cells from TRX585 antibody-containing cultures. Further detail can be found in FIG. 12 and the description thereof. In addition, both $CD4^+$ and $CD8^+$ T cells from TRX585 antibody-containing cultures were found to express high levels of granzyme B.

Overall, these data demonstrate that while T cells that have been cultured with APC and TRX585 antibody are able to exert a potent cytotoxic effect, such cells do not exhibit cytotoxic function in the absence of an appropriate trigger.

To determine whether the sequence of administration of TRX585 antibody impacted the modulation of immune responses, we conducted a series of in vitro experiments in which either TRX585 antibody and TCR stimulation were given simultaneously, or TRX585 antibody was added prior to the delivery of TCR stimulus. FIG. 13 shows that, while $CD4^+$ and $CD8^+$ T cells from PBMC cultures containing TRX585 antibody divided actively, concomitant treatment of PBMCs with anti-CD3 and TRX585 antibodies resulted in the inhibition of TRX585-induced T cell proliferation. In contrast, when T cells that were induced to proliferate in TRX585 antibody-containing PBMC cultures were subsequently purified and subjected to anti-CD3 stimulation, such T cells showed markedly increased responsiveness to TCR stimulation and upregulated TCR:CD3 complexes on the cell surface (see FIGS. 14A and 14B and the description thereof for additional detail).

Overall, these results indicate that TRX585 antibody may be used to overcome tumor-specific tolerance, enhance immune responses and/or induce tumor cell killing. Such effects may result from acquisition of anti-tumor cytotoxic function by the T cells resulting from administration of TRX585 antibodies followed by another therapeutic agent or antigen.

Example 4

Use of Anti-ILT5 Antibodies and Fragments as Immunostimulatory Adjuvants

An anti-ILT5 antibody or an ILT5-binding antibody fragment is used as an immunostimulatory agent to enhance an immune response to an antigen of interest. To stimulate an antibody or cellular immune response to an antigen of interest in vivo (e.g., for vaccination purposes), the antigen and an anti-ILT5 antibody or an ILT5-binding antibody fragment are administered to a human subject such that an enhanced immune response occurs in the subject. The antigen of interest and the anti-ILT5 antibody or ILT5-binding fragment are formulated appropriately, e.g., in separate pharmaceutical compositions. In certain situations, it may be desirable to administer the antibody at or about the same time as the antigen. In certain situations, it may be desirable to administer the antibody first, followed by the antigen, wherein a priming dose of the antibody is administered prior to administration of the antigen of interest to allow pharmacodynamic effect on the T-cells. For example, the anti-ILT5 antibody or ILT5-binding fragment can be administered 1-14 days (e.g., 3 days) before administration of the antigen of interest. It is expected that upon administration of the antigen of interest, a robust immune response against the antigen will be induced.

Example 5

Use of Anti-ILT5 Antibodies and Fragments to Increase a Specific Immune Response to Tumor Cells An anti-ILT5 antibody or an ILT5-binding antibody fragment is administered to a subject having tumor cells to overcome tumor-specific tolerance in the subject and to upmodulate an immune response to inhibit tumor growth, metastasis or to trigger tumor eradication. The tumor may be, for example, of the hematopoietic system, such as, a leukemia, lymphoma, or other malignancy of blood cells, or of a solid tumor, such as, a melanoma, gastric, lung, breast, and prostate cancers. In certain embodiments, such anti-ILT5 antibodies or ILT5-binding fragments are used as part of a combination therapy with another therapeutic treatment in a subject as adjuvants used to enhance an immune response such as in combination with chemotherapeutic agents. It is expected that upon administration of the anti-ILT5 antibody or ILT5-binding fragment thereof, tumor-specific tolerance will be reduced, resulting in diminished tumor growth or metastasis, and tumors will be eradicated or reduced in size or number. Following administration of the anti-ILT5 antibody, one or more appropriate tumor antigens (see above) or vaccines may also be administered.

Example 6

Use of Anti-ILT5 Antibodies and Fragments to Increase a Specific Immune Response to Cells Infected with a Virus An anti-ILT5 antibody or an ILT5-binding antibody fragment is administered to a subject suffering from a viral infection to upmodulate an immune response against cells infected with the virus. In certain embodiments, such anti-ILT5 antibodies or ILT5-binding fragments are used as part of a combination therapy with another therapeutic treatment in a subject as adjuvants used to enhance an immune response. It is expected that upon administration of the anti-ILT5 antibody or ILT5-binding fragment thereof, cells infected with the virus are eliminated or reduced in number. Following administration of the anti-ILT5 antibody, one or more appropriate viral antigens (see above) or vaccines may also be administered.

Example 7

Use of Crosslinked or Aggregated Anti-ILT5 Antibodies and Fragments to Induce Tolerance A crosslinked or otherwise aggregated anti-ILT5 antibody or an ILT5-binding antibody fragment is administered to a subject to inhibit a cellular immune response to an antigen of interest in vivo. Without wishing to be bound by theory, it is hypothesized that co-engagement of ILT5 receptors by such crosslinked, but not monovalent, anti-ILT5 antibodies and ILT5-binding fragments, initiates an inhibitory cascade in ILT-expressing APCs, which decreases their stimulatory potential or might render them tolerogenic. In certain embodiments, a crosslinked or otherwise aggregated anti-ILT5 antibody or ILT5-binding fragment may be administered at the same time as administration of another therapeutic agent or antigen to inhibit immune response to the antigen. It will be appreciated that the effects of concomitant removal of ILT ligand-transduced inhibitory signals in T cells and decreased DC-immunostimulatory capacities counterbalance each other and lead to diminished immunity. It is expected that upon administration of the anti-ILT5 antibody or ILT5-binding fragment thereof, tolerance will be induced.

Procedures such as those described in Example 6 would be useful as treatments of, for example, autoimmune diseases and immunological rejection of allogeneic and xenogeneic organ, tissue, or cell transplants.

What is claimed is:

1. An isolated antibody or an antigen binding fragment thereof that binds human immunoglobulin-like transcript 5 (ILT5) comprising:
   a heavy chain complementarity determining region 1 (VH CDR1) comprising the amino acid sequence of SEQ ID NO: 4;
   a heavy chain complementarity determining region 2 (VH CDR2) comprising the amino acid sequence of SEQ ID NO: 5;
   a heavy chain complementarity determining region 3 (VH CDR3) comprising the amino acid sequence of SEQ ID NO: 6;
   a light chain complementarity determining region 1 (VL CDR1) comprising the amino acid sequence of SEQ ID NO: 7;
   a light chain complementarity determining region 2 (VL CDR2) comprising the amino acid sequence of SEQ ID NO: 8; and
   a light chain complementarity determining region 3 (VL CDR3) comprising the amino acid sequence of SEQ ID NO: 9.

2. The isolated antibody or fragment of claim 1, further comprising at least one human framework region.

3. The isolated antibody or fragment of claim 2, wherein the human framework region is a human heavy chain framework region.

4. The isolated antibody or fragment of claim 3, comprising one or more human heavy chain framework regions from a heavy chain variable region comprising an amino acid sequence selected from the group consisting of the amino acid sequence of SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17.

5. The isolated antibody or fragment of claim 2, wherein the human framework region is a human light chain framework region.

6. The isolated antibody or fragment of claim 5, comprising one or more human light chain framework regions from a light chain variable region comprising an amino acid sequence selected from the group consisting of the amino acid sequence of SEQ ID NO: 18, SEQ ID NO: 19, SEQ ID NO: 20, SEQ ID NO: 21, SEQ ID NO: 22, SEQ ID NO: 23, and SEQ ID NO: 24.

7. The isolated antibody or fragment of claim 6, comprising one or more human heavy chain framework regions from a heavy chain variable region comprising an amino acid sequence selected from the group consisting of the amino acid sequence of SEQ ID NO: 10, SEQ ID NO: 11, SEQ ID NO: 12, SEQ ID NO: 13, SEQ ID NO: 14, SEQ ID NO: 15, SEQ ID NO: 16, and SEQ ID NO: 17.

8. The isolated antibody or fragment of claim 1, comprising a heavy chain constant region.

9. The isolated antibody or fragment of claim 8, wherein the heavy chain constant region is selected from the group consisting of: an IgG1 constant region, an IgG2 constant region, an IgG3 constant region, an IgG4 constant region, an IgA constant region, an IgE constant region, an IgM constant region, and an IgD constant region.

10. The isolated antibody or fragment of claim 8, wherein the heavy chain constant region is an IgG1 constant region.

11. The isolated antibody or fragment claim 8, wherein the heavy chain constant region comprises the amino acid sequence of SEQ ID NO: 25 or SEQ ID NO: 26.

12. The isolated antibody or fragment of claim 1, comprising a light chain constant region.

13. The isolated antibody or fragment of claim 12, wherein the light chain constant region is a kappa light chain constant region.

14. The isolated antibody or fragment of claim 12, wherein the light chain constant region is a lambda light chain constant region.

15. The isolated antibody or fragment claim 12, wherein the light chain constant region comprises the amino acid sequence of SEQ ID NO: 27.

16. The isolated antibody or fragment of claim 1, comprising a light chain comprising the amino acid sequence of SEQ ID NO: 28.

17. The isolated antibody or fragment of claim 16, further comprising a heavy chain comprising the amino acid sequence of SEQ ID NO: 29, SEQ ID NO: 30, SEQ ID NO: 31, or SEQ ID NO: 32.

18. The isolated antibody or fragment of claim claim 1, comprising a heavy chain comprising the amino acid sequence of SEQ ID NO: 29, SEQ ID NO: 30, SEQ ID NO: 31, or SEQ ID NO: 32.

19. The isolated antibody or fragment of claim 1, comprising a light chain variable region comprising the amino acid sequence of SEQ ID NO: 1.

20. The isolated antibody or fragment of claim 1, comprising a heavy chain variable region comprising the amino acid sequence of SEQ ID NO: 2 or SEQ ID NO: 3.

21. The isolated antibody or fragment of claim 1, comprising a light chain variable region comprising the amino acid sequence of SEQ ID NO: 1, and further comprising a heavy chain variable region comprising the amino acid sequence of SEQ ID NO: 2 or SEQ ID NO: 3.

22. An antigen binding fragment of claim 1, wherein the fragment comprises a Fab fragment, a F(ab')2 fragment, or a scFv fragment.

* * * * *